US012790402B2

(12) United States Patent
Liang et al.

(10) Patent No.: US 12,790,402 B2
(45) Date of Patent: Nov. 10, 2026

(54) DEVELOPMENT AND APPLICATION OF IMMUNE CELL ACTIVATOR

(71) Applicant: Bio-Thera Solutions, Ltd., Guangzhou (CN)

(72) Inventors: Shizhong Liang, Guangzhou (CN); Dandan Zheng, Guangzhou (CN); Jin-Chen Yu, Guangzhou (CN); Shengfeng Li, Guangzhou (CN)

(73) Assignee: BIO-THERA SOLUTIONS, LTD., Guangzhou (CN)

( * ) Notice: Subject to any disclaimer, the term of this patent is extended or adjusted under 35 U.S.C. 154(b) by 1007 days.

(21) Appl. No.: 17/913,429

(22) PCT Filed: Mar. 22, 2021

(86) PCT No.: PCT/CN2021/081993
§ 371 (c)(1),
(2) Date: Sep. 21, 2022

(87) PCT Pub. No.: WO2021/190431
PCT Pub. Date: Sep. 30, 2021

(65) Prior Publication Data
US 2023/0139700 A1 May 4, 2023

(30) Foreign Application Priority Data
Mar. 23, 2020 (CN) ......................... 202010208900.0

(51) Int. Cl.
*C07K 16/28* (2006.01)
*A61K 39/00* (2006.01)
*A61P 35/00* (2006.01)
*A61P 35/02* (2006.01)

(52) U.S. Cl.
CPC .......... *C07K 16/2878* (2013.01); *A61P 35/00* (2018.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,790,938 | B1 * | 9/2004 | Berchtold | A61P 43/00 424/130.1 |
| 10,442,866 | B1 | 10/2019 | Hu et al. | |
| 2016/0347849 | A1 * | 12/2016 | Cai | A61P 35/00 |
| 2018/0171023 | A1 * | 6/2018 | Harding | C07K 16/3023 |
| 2018/0237534 | A1 | 8/2018 | Cai et al. | |
| 2023/0416386 | A1 * | 12/2023 | Liang | C07K 16/2878 |

FOREIGN PATENT DOCUMENTS

| | | | | |
|---|---|---|---|---|
| CN | 108137687 A | | 6/2018 | |
| CN | 110467674 A | | 11/2019 | |
| CN | 110536903 A | | 12/2019 | |
| EP | 3126394 A1 | | 2/2017 | |
| WO | 2015153513 A1 | | 10/2015 | |
| WO | WO-2018112346 A1 | * | 6/2018 | A61P 35/00 |
| WO | WO-2018177220 A1 | * | 10/2018 | C07K 16/2878 |
| WO | WO-2021238932 A1 | * | 12/2021 | A61P 35/00 |
| WO | WO-2022007807 A1 | * | 1/2022 | A61K 39/395 |

OTHER PUBLICATIONS

Rudikoff et al. PNAS. 79: 1979-1983; Published: Mar. 15, 1982 (Year: 1982).*
Murphy et al. Journal of Immunological Methods. 463: 127-133; Published: Oct. 12, 2018 (Year: 2018).*
Casset et al. BBRC 2003, 307(1): 198-205; Published: Jul. 18, 2003 (Year: 2003).*
Padlan et al. PNAS. 86: 5938-5942; Published: Aug. 1, 1989 (Year: 1989).*
Lamminmaki et al. Journal of Biological Chemistry. 276(39): 36687-36694; Published: Sep. 28, 2001 (Year: 2001).*
Compaan et al, "The Crystal Structure of the Costimulatory OX40-OX40L Complex," Structure, vol. 14, pp. 1321-1330 (2006).
Estep et al, "High throughput solution-based measurement of antibody-antigen affinity and epitope binning," mAbs, vol. 5, No. 2, pp. 270-278 (2013).
Gramaglia et al, "The OX40 Costimulatory Receptor Determines the Development of CD4 Memory by Regulating Primary Clonal Expansion," The Journal of Immunology, vol. 165, pp. 3043-3050 (2000).
Griseri et al, "OX40 is required for regulatory T cell-mediated control of colitis," The Journal of Experimental Medicine, vol. 207, pp. 699-709 (2010).
Murata et al, "Constitutive OX40/OX40 Ligand Interaction Induces Autoimmune-Like Diseases," The Journal of Immunology, vol. 169, pp. 4628-4636 (2002).
Paterson et al, "Antigens of Activated Rat T Lymphocytes Including a Molecule of 50,000 Mr Detected Only on CD4 Positive T Blasts," Molecular Immunology, vol. 24, No. 12, pp. 1281-1290 (1987).
Piconese et al, "A non-redundant role for OX40 in the competitive fitness of Treg in response to IL-2," European Journal of Immunology, vol. 40, pp. 2902-2913 (2010).
Piconese et al, "OX40 triggering blocks suppression by regulatory T cells and facilitates tumor rejection," The Journal of Experimental Medicine, vol. 205, No. 4, pp. 825-839 (2008).
Ruby et al, "Cutting Edge: OX40 Agonists Can Drive Regulatory T Cell Expansion if the Cytokine Milieu Is Right," The Journal of Immunology, vol. 183, pp. 4853-4857 (2009).

(Continued)

*Primary Examiner* — Juliet C Switzer
*Assistant Examiner* — Katherine Ann Holtzman
(74) *Attorney, Agent, or Firm* — Panitch Schwarze Belidario & Nadel LLP

(57) ABSTRACT

The development and use of an anti-OX40 antibody and immune cell activation is disclosed. The anti-OX40 antibody or a fragment of the anti-OX40 antibody retains strong binding to human OX40 or Rhesus Monkey OX40. The anti-OX40 antibody or a fragment of the anti-OX40 antibody more effectively activates T cells, generates stronger immune responses, and improves anti-tumor activity.

18 Claims, 8 Drawing Sheets

Specification includes a Sequence Listing.

(56) References Cited

OTHER PUBLICATIONS

So et al, "Signals from OX40 regulate nuclear factor of activated T cells c1 and T cell helper 2 lineage commitment," Proceedings of the National Academy of Sciences of the United States of America, vol. 103, pp. 3740-3745 (2006).
Song et al, "Activation of NF-kB1 by OX40 Contributes to Antigen-Driven T Cell Expansion and Survival," The Journal of Immunology, vol. 180, pp. 7240-7248 (2008).
Song et al, "The costimulation-regulated duration of PKB activation controls T cell longevity," Nature Immunology, vol. 5, pp. 150-158 (2004).
Voo et al, "Antibodies Targeting Human OX40 Expand Effector T Cells and Block Inducible and Natural Regulatory T Cell Function," The Journal of Immunology, vol. 191, pp. 3641-3650 (2013).
Vu et al, "OX40 costimulation turns off Foxp3+ Tregs," Blood, vol. 110, pp. 2501-2510 (2007).
Wajant et al, "Principles of antibody-mediated TNF receptor activation," Cell Death and Differentiation, vol. 22, pp. 1727-1741 (2015).
Ward-Kavanagh et al, "The TNF Receptor Superfamily in Co-stimulating and Co-inhibitory Responses," Immunity Review, vol. 44, No. 5, pp. 1005-1009 (2016).
Willoughby et al, "OX40: Structure and function—What questions remain?," Molecular Immunology, vol. 83, pp. 13-22 (2017).
Int'l Search Report issued Jul. 7, 2021 in Int'l Application No. PCT/CN2021/081993.
Kuang, et al., Development and characterization of a novel anti-OX40 antibody for potent immune activation, Cancer Immunology Immunotherapy (2020) 69; 939-950, Feb. 20, 2020.
Cebada, et al., OX40 agonists for cancer treatment: a patent review, Expert Opinion on Therapeutic Patents, (2021), vol. 31, No. 1: 81-90, Oct. 6, 2020.
Rudikoff, et al., Single amino acid substitution altering antigen-binding specificity, Pro. Natl. Acad. Sci. USA, Immunology, vol. 79, pp. 1979-1983, Mar. 1982.
Winkler, et al., Changing the Antigen Binding Specificity by Single Point Mutations of an Anti-p24 (HIV-1) Antibody, Journal of Immunology, 2000, 165: 4505-4514.
Tabasinezhad et al., Trends in therapeutic antibody affinity maturation: From in-vitro towards next-generation sequencing approaches, 212 Immunology Letters 106-113 (2019).
Warszawski et al., Optimizing antibody affinity and stability by the automated design of the variable lightheavy chain interfaces, 15(8) PLoS Comput. Biol. 1-24 (2019).
European Communication issued on Jun. 27, 2024, in counterpart EP Application No. 21775350.8.

* cited by examiner

| | Antibody-F23-32k | 11D4 |
|---|---|---|
| EC50 | 0.1405 | 0.2261 |

| Sample group | Antibody-F23-32k | Antibody-F23-32k + protein A | 32k-RY | 32k-R |
|---|---|---|---|---|
| Jurkat-hOX40- $NF_kB$ (RLU) | 350 | 3700 | 2600 | 1523 |
| Jurkat-hOX40- $NF_kB$-2 (RLU) | 4300 | $6.0\times10^4$ | $5.2\times10^4$ | $4.4\times10^4$ |

| Sample group | IgG + raji | Antibody-F23-32k + raji | 32k-RY + raji | 32k-R + raji | OX40L |
|---|---|---|---|---|---|
| Jurkat-hOX40- $NF_kB$ (RLU) | 900 | N.D | 6045 | 7600 | N.D |
| Jurkat-hOX40- $NF_kB$-2 (RLU) | $1.6\times10^4$ | $1.5\times10^5$ | $1.4\times10^5$ | $1.5\times10^5$ | $5.9\times10^4$ |

| | Antibody-F23-4k | Antibody-F23-32k | 4k-RY | 32k-RY | OX40mAb24 |
|---|---|---|---|---|---|
| TGI% | 65.4% | 74.6% | 66.1% | 48.1% | 48.1% |

| | 11D4 | Antibody M | Antibody M-KF |
|---|---|---|---|
| EC50 | 1.172 | 1.203 | 1.342 |

| | Antibody M | Antibody M-KF |
|---|---|---|
| EC50 | 67.01 | 23.90 |

| | Antibody M-KF | Antibody M | 11D4 |
|---|---|---|---|
| EC50(ug/ml) | 0.0722 | 0.06020 | 0.0810 |

SEQUENCE LISTING

```
<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: VH CDR1

<400> SEQUENCE: 1

Gly Phe Thr Phe Ser Ser Tyr Ala
1               5


<210> SEQ ID NO 2
<211> LENGTH: 8
<212> TYPE: PRT
<213> ORGANISM: Artificial Sequence
<220> FEATURE:
<223> OTHER INFORMATION: VH CDR2

<400> SEQUENCE: 2

Ile Ser Tyr Asp Gly Ser Asn Lys
1               5
```

<210> SEQ ID NO 3
<211> LENGTH: 16
<212> TYPE: PRT
<213> ORGANISM: Artificial Sequence
<220> FEATURE:
<223> OTHER INFORMATION: VH CDR3

<400> SEQUENCE: 3

Ala Arg Glu Leu Gly Val Tyr Ser Gly Tyr Asp Thr Pro Phe Asp Tyr
1 5 10 15

<210> SEQ ID NO 4
<211> LENGTH: 8
<212> TYPE: PRT
<213> ORGANISM: Artificial Sequence
<220> FEATURE:
<223> OTHER INFORMATION: VH CDR1

<400> SEQUENCE: 4

Gly Phe Thr Phe Asp Asp Tyr Ala
1 5

<210> SEQ ID NO 5
<211> LENGTH: 8
<212> TYPE: PRT
<213> ORGANISM: Artificial Sequence
<220> FEATURE:
<223> OTHER INFORMATION: VH CDR2

<400> SEQUENCE: 5

Ile Gly Gly Ser Gly Gly Ser Thr
1 5

<210> SEQ ID NO 6
<211> LENGTH: 15
<212> TYPE: PRT
<213> ORGANISM: Artificial Sequence
<220> FEATURE:
<223> OTHER INFORMATION: VH CDR3

<400> SEQUENCE: 6

Ala Lys Asp Arg Gly Tyr Gly Asp Tyr Tyr Trp Tyr Phe Asp Leu
1 5 10 15

<210> SEQ ID NO 7
<211> LENGTH: 17
<212> TYPE: PRT
<213> ORGANISM: Artificial Sequence
<220> FEATURE:
<223> OTHER INFORMATION: VH CDR2

<400> SEQUENCE: 7

Val Ile Ser Glu Asp Gly Ser Asn Gln Tyr Tyr Ala Asp Ser Val Lys
1 5 10 15

Gly

<210> SEQ ID NO 8
<211> LENGTH: 8
<212> TYPE: PRT
<213> ORGANISM: Artificial Sequence
<220> FEATURE:
<223> OTHER INFORMATION: VH CDR2

<400> SEQUENCE: 8

Ile Ser Gly Ser Gly Gly Asn Thr
1 5

<210> SEQ ID NO 9
<211> LENGTH: 15
<212> TYPE: PRT
<213> ORGANISM: Artificial Sequence
<220> FEATURE:
<223> OTHER INFORMATION: VH CDR3

<400> SEQUENCE: 9

```
Ala Lys Asp Pro Leu Gly Ser Ser Trp Phe Glu Tyr Phe Gln His
1               5                   10                  15
```

<210> SEQ ID NO 10
<211> LENGTH: 5
<212> TYPE: PRT
<213> ORGANISM: Artificial Sequence
<220> FEATURE:
<223> OTHER INFORMATION: VH CDR1

<400> SEQUENCE: 10

```
Ser Tyr Gly Met His
1               5
```

<210> SEQ ID NO 11
<211> LENGTH: 17
<212> TYPE: PRT
<213> ORGANISM: Artificial Sequence
<220> FEATURE:
<223> OTHER INFORMATION: VH CDR2

<400> SEQUENCE: 11

```
Val Ile Ser Tyr Asp Gly Ser Asn Gln Tyr Tyr Ala Asp Ser Val Lys
1               5                   10                  15

Gly
```

<210> SEQ ID NO 12
<211> LENGTH: 13
<212> TYPE: PRT
<213> ORGANISM: Artificial Sequence
<220> FEATURE:
<223> OTHER INFORMATION: VH CDR3

<400> SEQUENCE: 12

```
Asp Asn Gln Asp Ser Ser Pro Asp Val Gly Ile Asp Tyr
1               5                   10
```

<210> SEQ ID NO 13
<211> LENGTH: 17
<212> TYPE: PRT
<213> ORGANISM: Artificial Sequence
<220> FEATURE:
<223> OTHER INFORMATION: VH CDR2

<400> SEQUENCE: 13

```
Val Ile Ala Glu Val Gly Ser Asn Gln Tyr Tyr Ala Asp Ser Val Lys
1               5                   10                  15

Gly
```

<210> SEQ ID NO 14
<211> LENGTH: 8
<212> TYPE: PRT
<213> ORGANISM: Artificial Sequence
<220> FEATURE:
<223> OTHER INFORMATION: VH CDR2

<400> SEQUENCE: 14

Ile Ser Asn Ser Gly Gly Ser Thr
1 5

<210> SEQ ID NO 15
<211> LENGTH: 9
<212> TYPE: PRT
<213> ORGANISM: Artificial Sequence
<220> FEATURE:
<223> OTHER INFORMATION: VH CDR3

<400> SEQUENCE: 15

Ala Lys Asp Gly Pro Tyr Phe Asp Tyr
1 5

<210> SEQ ID NO 16
<211> LENGTH: 8
<212> TYPE: PRT
<213> ORGANISM: Artificial Sequence
<220> FEATURE:
<223> OTHER INFORMATION: VH CDR1

<400> SEQUENCE: 16

Gly Phe Thr Phe Ser Thr Tyr Ala
1 5

<210> SEQ ID NO 17
<211> LENGTH: 8
<212> TYPE: PRT
<213> ORGANISM: Artificial Sequence
<220> FEATURE:
<223> OTHER INFORMATION: VH CDR2

<400> SEQUENCE: 17

Ile Ser Gly Thr Gly Asp Trp Ala
1 5

<210> SEQ ID NO 18
<211> LENGTH: 17
<212> TYPE: PRT
<213> ORGANISM: Artificial Sequence
<220> FEATURE:
<223> OTHER INFORMATION: VH CDR3

<400> SEQUENCE: 18

Ala Lys Ser Ser Ser Thr Val Ala Thr Asp Phe Asp Tyr Gly Met Asp
1 5 10 15

Val

<210> SEQ ID NO 19
<211> LENGTH: 7
<212> TYPE: PRT
<213> ORGANISM: Artificial Sequence
<220> FEATURE:
<223> OTHER INFORMATION: VL CDR2

<400> SEQUENCE: 19

Ala Ala Val Ala Leu Gln Ser
1 5

<210> SEQ ID NO 20
<211> LENGTH: 8
<212> TYPE: PRT
<213> ORGANISM: Artificial Sequence
<220> FEATURE:
<223> OTHER INFORMATION: VH CDR2

<400> SEQUENCE: 20

Ile Ser Gly Ser Gly Gly Ser Thr
1 5

<210> SEQ ID NO 21
<211> LENGTH: 13
<212> TYPE: PRT
<213> ORGANISM: Artificial Sequence
<220> FEATURE:
<223> OTHER INFORMATION: VH CDR3

<400> SEQUENCE: 21

Ala Arg Gly Asp Ser Ser Ser Trp Phe Ile Phe Gln Asp
1 5 10

<210> SEQ ID NO 22
<211> LENGTH: 8
<212> TYPE: PRT
<213> ORGANISM: Artificial Sequence
<220> FEATURE:
<223> OTHER INFORMATION: VH CDR1

<400> SEQUENCE: 22

Gly Phe Thr Val Ser Ser Asn Tyr
1 5

<210> SEQ ID NO 23
<211> LENGTH: 7
<212> TYPE: PRT
<213> ORGANISM: Artificial Sequence
<220> FEATURE:
<223> OTHER INFORMATION: VH CDR2

<400> SEQUENCE: 23

Ile Tyr Tyr Gly Gly Ser Thr
1 5

<210> SEQ ID NO 24
<211> LENGTH: 11
<212> TYPE: PRT
<213> ORGANISM: Artificial Sequence
<220> FEATURE:
<223> OTHER INFORMATION: VH CDR3

<400> SEQUENCE: 24

Ala Arg Val Val Val Pro Gly Tyr Phe Asp Leu
1 5 10

<210> SEQ ID NO 25
<211> LENGTH: 7
<212> TYPE: PRT
<213> ORGANISM: Artificial Sequence
<220> FEATURE:
<223> OTHER INFORMATION: VL CDR2

<400> SEQUENCE: 25

Ala Ala Val Gly Leu Gln Ser
1 5

<210> SEQ ID NO 26
<211> LENGTH: 17
<212> TYPE: PRT
<213> ORGANISM: Artificial Sequence
<220> FEATURE:
<223> OTHER INFORMATION: VH CDR2

<400> SEQUENCE: 26

```
Val Ile Trp Glu Asp Gly Ser Asn Gln Tyr Tyr Ala Asp Ser Val Lys
1               5                   10                  15

Gly


<210> SEQ ID NO 27
<211> LENGTH: 13
<212> TYPE: PRT
<213> ORGANISM: Artificial Sequence
<220> FEATURE:
<223> OTHER INFORMATION: VH CDR3

<400> SEQUENCE: 27

Asp Asn Gln Asp Thr Ser Pro Asp Val Gly Ile Asp Tyr
1               5                   10


<210> SEQ ID NO 28
<211> LENGTH: 6
<212> TYPE: PRT
<213> ORGANISM: Artificial Sequence
<220> FEATURE:
<223> OTHER INFORMATION: VL CDR1

<400> SEQUENCE: 28

Arg Asp Ile Arg Asp Asp
1               5


<210> SEQ ID NO 29
<211> LENGTH: 3
<212> TYPE: PRT
<213> ORGANISM: Artificial Sequence
<220> FEATURE:
<223> OTHER INFORMATION: VL CDR2

<400> SEQUENCE: 29

Ala Ala Ser
1


<210> SEQ ID NO 30
<211> LENGTH: 9
<212> TYPE: PRT
<213> ORGANISM: Artificial Sequence
<220> FEATURE:
<223> OTHER INFORMATION: VL CDR3

<400> SEQUENCE: 30

Leu Gln Asp Ser Asp Tyr Pro Leu Thr
1               5


<210> SEQ ID NO 31
<211> LENGTH: 9
<212> TYPE: PRT
<213> ORGANISM: Artificial Sequence
<220> FEATURE:
<223> OTHER INFORMATION: VL CDR1

<400> SEQUENCE: 31

Ser Ser Asp Val Gly Gly Tyr Asn Tyr
1               5


<210> SEQ ID NO 32
<211> LENGTH: 3
<212> TYPE: PRT
<213> ORGANISM: Artificial Sequence
<220> FEATURE:
<223> OTHER INFORMATION: VL CDR2

<400> SEQUENCE: 32
```

Asp Val Ser
1

<210> SEQ ID NO 33
<211> LENGTH: 10
<212> TYPE: PRT
<213> ORGANISM: Artificial Sequence
<220> FEATURE:
<223> OTHER INFORMATION: VL CDR3

<400> SEQUENCE: 33

Ser Ser Tyr Thr Thr Ser Ser Thr Leu Val
1 5 10

<210> SEQ ID NO 34
<211> LENGTH: 9
<212> TYPE: PRT
<213> ORGANISM: Artificial Sequence
<220> FEATURE:
<223> OTHER INFORMATION: VL CDR3

<400> SEQUENCE: 34

Gln Gln Tyr Thr Asp Tyr Pro Leu Thr
1 5

<210> SEQ ID NO 35
<211> LENGTH: 3
<212> TYPE: PRT
<213> ORGANISM: Artificial Sequence
<220> FEATURE:
<223> OTHER INFORMATION: VL CDR2

<400> SEQUENCE: 35

Glu Val Ser
1

<210> SEQ ID NO 36
<211> LENGTH: 11
<212> TYPE: PRT
<213> ORGANISM: Artificial Sequence
<220> FEATURE:
<223> OTHER INFORMATION: VL CDR3

<400> SEQUENCE: 36

Ser Ser Tyr Ser Ser Ser Ser Thr Leu Val Val
1 5 10

<210> SEQ ID NO 37
<211> LENGTH: 6
<212> TYPE: PRT
<213> ORGANISM: Artificial Sequence
<220> FEATURE:
<223> OTHER INFORMATION: VL CDR1

<400> SEQUENCE: 37

Gln Asp Ile Leu Gly Tyr
1 5

<210> SEQ ID NO 38
<211> LENGTH: 3
<212> TYPE: PRT
<213> ORGANISM: Artificial Sequence
<220> FEATURE:
<223> OTHER INFORMATION: VL CDR2

<400> SEQUENCE: 38

Ala Thr Ser
1

<210> SEQ ID NO 39
<211> LENGTH: 9
<212> TYPE: PRT
<213> ORGANISM: Artificial Sequence
<220> FEATURE:
<223> OTHER INFORMATION: VL CDR3

<400> SEQUENCE: 39

Gln Gln Tyr Asn Ser Tyr Pro Leu Thr
1 5

<210> SEQ ID NO 40
<211> LENGTH: 8
<212> TYPE: PRT
<213> ORGANISM: Artificial Sequence
<220> FEATURE:
<223> OTHER INFORMATION: VL CDR1

<400> SEQUENCE: 40

Gln Ser Ile Ser Ser Tyr Leu Asn
1 5

<210> SEQ ID NO 41
<211> LENGTH: 9
<212> TYPE: PRT
<213> ORGANISM: Artificial Sequence
<220> FEATURE:
<223> OTHER INFORMATION: VL CDR3

<400> SEQUENCE: 41

Gln Gln Tyr Asp Asp Tyr Pro Leu Thr
1 5

<210> SEQ ID NO 42
<211> LENGTH: 9
<212> TYPE: PRT
<213> ORGANISM: Artificial Sequence
<220> FEATURE:
<223> OTHER INFORMATION: VL CDR3

<400> SEQUENCE: 42

Leu Gln Ile Asp Ser Tyr Pro Leu Thr
1 5

<210> SEQ ID NO 43
<211> LENGTH: 11
<212> TYPE: PRT
<213> ORGANISM: Artificial Sequence
<220> FEATURE:
<223> OTHER INFORMATION: VL CDR1

<400> SEQUENCE: 43

Arg Ala Ser Gln Asn Ile Ser Pro Phe Leu Asn
1 5 10

<210> SEQ ID NO 44
<211> LENGTH: 7
<212> TYPE: PRT
<213> ORGANISM: Artificial Sequence
<220> FEATURE:
<223> OTHER INFORMATION: VL CDR2

<400> SEQUENCE: 44

Ala Ala Ser Ser Leu Gln Ser 1 5

<210> SEQ ID NO 45
<211> LENGTH: 9
<212> TYPE: PRT
<213> ORGANISM: Artificial Sequence
<220> FEATURE:
<223> OTHER INFORMATION: VL CDR3

<400> SEQUENCE: 45

Gln Gln Tyr Asn Asp Tyr Pro Leu Thr
1 5

<210> SEQ ID NO 46
<211> LENGTH: 6
<212> TYPE: PRT
<213> ORGANISM: Artificial Sequence
<220> FEATURE:
<223> OTHER INFORMATION: VL CDR1

<400> SEQUENCE: 46

Gln Gly Ile Gly Asp Asp
1 5

<210> SEQ ID NO 47
<211> LENGTH: 3
<212> TYPE: PRT
<213> ORGANISM: Artificial Sequence
<220> FEATURE:
<223> OTHER INFORMATION: VL CDR2

<400> SEQUENCE: 47

Lys Ala Ser
1

<210> SEQ ID NO 48
<211> LENGTH: 9
<212> TYPE: PRT
<213> ORGANISM: Artificial Sequence
<220> FEATURE:
<223> OTHER INFORMATION: VL CDR3

<400> SEQUENCE: 48

Gln Gln Ala His Ser Phe Pro Pro Thr
1 5

<210> SEQ ID NO 49
<211> LENGTH: 9
<212> TYPE: PRT
<213> ORGANISM: Artificial Sequence
<220> FEATURE:
<223> OTHER INFORMATION: VL CDR1

<400> SEQUENCE: 49

Glu Glu Ile Gly Ser Trp Leu Ala Trp
1 5

<210> SEQ ID NO 50
<211> LENGTH: 3
<212> TYPE: PRT
<213> ORGANISM: Artificial Sequence
<220> FEATURE:
<223> OTHER INFORMATION: VL CDR2

<400> SEQUENCE: 50

Glu Ala Ser
1

<210> SEQ ID NO 51
<211> LENGTH: 9
<212> TYPE: PRT
<213> ORGANISM: Artificial Sequence
<220> FEATURE:
<223> OTHER INFORMATION: VL CDR3

<400> SEQUENCE: 51

Gln Gln Tyr Gly Ser Tyr Pro Pro Thr
1 5

<210> SEQ ID NO 52
<211> LENGTH: 6
<212> TYPE: PRT
<213> ORGANISM: Artificial Sequence
<220> FEATURE:
<223> OTHER INFORMATION: VL CDR1

<400> SEQUENCE: 52

Glu Asp Ile Gly Arg Trp
1 5

<210> SEQ ID NO 53
<211> LENGTH: 9
<212> TYPE: PRT
<213> ORGANISM: Artificial Sequence
<220> FEATURE:
<223> OTHER INFORMATION: VL CDR3

<400> SEQUENCE: 53

Gln Gln Tyr Ser Asp Tyr Pro Leu Thr
1 5

<210> SEQ ID NO 54
<211> LENGTH: 9
<212> TYPE: PRT
<213> ORGANISM: Artificial Sequence
<220> FEATURE:
<223> OTHER INFORMATION: VL CDR3

<400> SEQUENCE: 54

Gln Gln Tyr Tyr Asn Tyr Pro Pro Thr
1 5

<210> SEQ ID NO 55
<211> LENGTH: 8
<212> TYPE: PRT
<213> ORGANISM: Artificial Sequence
<220> FEATURE:
<223> OTHER INFORMATION: VL CDR1

<400> SEQUENCE: 55

Ser Ser Asn Met Gly Ser Asn Pro
1 5

<210> SEQ ID NO 56
<211> LENGTH: 3
<212> TYPE: PRT
<213> ORGANISM: Artificial Sequence
<220> FEATURE:
<223> OTHER INFORMATION: VL CDR2

<400> SEQUENCE: 56

Asn Asn Asn
1

<210> SEQ ID NO 57
<211> LENGTH: 11
<212> TYPE: PRT
<213> ORGANISM: Artificial Sequence
<220> FEATURE:
<223> OTHER INFORMATION: VL CDR3

<400> SEQUENCE: 57

Ala Ala Trp Asp Asp Gly Leu Asn Gly Trp Val
1 5 10

<210> SEQ ID NO 58
<211> LENGTH: 9
<212> TYPE: PRT
<213> ORGANISM: Artificial Sequence
<220> FEATURE:
<223> OTHER INFORMATION: VL CDR1

<400> SEQUENCE: 58

Asp Ser Leu Arg Ser Tyr Tyr Ala Ser
1 5

<210> SEQ ID NO 59
<211> LENGTH: 3
<212> TYPE: PRT
<213> ORGANISM: Artificial Sequence
<220> FEATURE:
<223> OTHER INFORMATION: VL CDR2

<400> SEQUENCE: 59

Asn Asn Arg
1

<210> SEQ ID NO 60
<211> LENGTH: 10
<212> TYPE: PRT
<213> ORGANISM: Artificial Sequence
<220> FEATURE:
<223> OTHER INFORMATION: VL CDR3

<400> SEQUENCE: 60

His Ser Arg Asp Ser Ser Gly Lys Tyr Val
1 5 10

<210> SEQ ID NO 61
<211> LENGTH: 11
<212> TYPE: PRT
<213> ORGANISM: Artificial Sequence
<220> FEATURE:
<223> OTHER INFORMATION: VL CDR1

<400> SEQUENCE: 61

Arg Ala Ser Gln Asn Ile Ser Pro Phe Leu Asn
1 5 10

<210> SEQ ID NO 62
<211> LENGTH: 7
<212> TYPE: PRT
<213> ORGANISM: Artificial Sequence
<220> FEATURE:
<223> OTHER INFORMATION: VL CDR2

<400> SEQUENCE: 62

Ala Ala Val Gly Ser Gln Ser
1 5

<210> SEQ ID NO 63
<211> LENGTH: 8
<212> TYPE: PRT
<213> ORGANISM: Artificial Sequence
<220> FEATURE:
<223> OTHER INFORMATION: VL CDR3

<400> SEQUENCE: 63

```
Gln Gln Tyr Thr Asp Tyr Pro Leu
1               5
```

<210> SEQ ID NO 64
<211> LENGTH: 123
<212> TYPE: PRT
<213> ORGANISM: Artificial Sequence
<220> FEATURE:
<223> OTHER INFORMATION: Heavy chain variable region

<400> SEQUENCE: 64

```
Gln Val Gln Leu Gln Glu Ser Gly Gly Gly Leu Glu Lys Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Leu Gly Val Tyr Ser Gly Tyr Asp Thr Pro Phe Asp Tyr
            100                 105                 110

Trp Gly Gln Gly Thr Leu Val Thr Val Ser Ser
        115                 120
```

<210> SEQ ID NO 65
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 65

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Arg Gly Leu Glu Trp Val
        35                  40                  45

Ser Gly Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Gly Ala Glu Asp Thr Ala Val Tyr Tyr Cys
            85                  90                  95

Ala Lys Asp Arg Gly Tyr Gly Asp Tyr Tyr Trp Tyr Phe Asp Leu Trp
            100                 105                 110

Gly Arg Gly Thr Leu Val Thr Val Ser Ser
        115                 120
```

<210> SEQ ID NO 66
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 66

```
Gln Val Gln Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Asn Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Leu Gly Ser Ser Trp Phe Glu Tyr Phe Gln His Trp
            100                 105                 110

Gly Gln Gly Thr Leu Val Thr Val Ser Ser
        115                 120
```

<210> SEQ ID NO 67
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 67

```
Gln Val Gln Leu Glu Glu Ser Gly Gly Gly Val Val Gln Pro Gly Glu
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Gln Asp Ser Ser Pro Asp Val Gly Ile Asp Tyr Trp
            100                 105                 110

Gly Gln Gly Thr Leu Val Thr Val Ser Ser
        115                 120
```

<210> SEQ ID NO 68
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 68

```
Gln Val Gln Leu Gln Arg Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Thr Trp Val Arg Gln Ala Pro Gly Lys Gly Leu Glu Trp Val
        35                  40                  45

Ser Ala Ile Ser Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Pro Tyr Phe Asp Tyr Trp Gly Gln Gly Thr Leu Val
            100                 105                 110

Thr Val Ser Ser
        115


<210> SEQ ID NO 69
<211> LENGTH: 124
<212> TYPE: PRT
<213> ORGANISM: Artificial Sequence
<220> FEATURE:
<223> OTHER INFORMATION: Heavy chain variable region

<400> SEQUENCE: 69

Gln Val Gln Leu Val Glu Ser Gly Gly Gly Leu Ile Gln Pro Gly Gly
1               5                   10                  15

Ser Leu Arg Leu Ser Cys Thr Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Asp Trp Ala Ser Tyr Ala Asp Ser Val
    50                  55                  60

Lys Gly Arg Phe Thr Thr Ser Arg Asp Asn Ser Arg Asn Thr Leu Tyr
65                  70                  75                  80

Leu Gln Met Asn Asn Leu Arg Asp Glu Asp Thr Ala Ile Tyr Tyr Cys
                85                  90                  95

Ala Lys Ser Ser Ser Thr Val Ala Thr Asp Phe Asp Tyr Gly Met Asp
            100                 105                 110

Val Trp Gly Gln Gly Thr Leu Val Thr Val Ser Ser
        115                 120


<210> SEQ ID NO 70
<211> LENGTH: 120
<212> TYPE: PRT
<213> ORGANISM: Artificial Sequence
<220> FEATURE:
<223> OTHER INFORMATION: Heavy chain variable region

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Ser Ser Ser Trp Phe Ile Phe Gln Asp Trp Gly Gln
            100                 105                 110

Gly Thr Leu Val Thr Val Ser Ser
        115                 120


<210> SEQ ID NO 71
<211> LENGTH: 117
<212> TYPE: PRT
<213> ORGANISM: Artificial Sequence
<220> FEATURE:
<223> OTHER INFORMATION: Heavy chain variable region

<400> SEQUENCE: 71

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Glu Gly Leu Glu Trp Ile
        35                  40                  45

Ala Thr Ile Tyr Tyr Gly Gly Ser Thr Tyr Tyr Asn Pro Ser Leu Lys
    50                  55                  60

Ser Arg Val Thr Ile Ser Ala Asp Met Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Val Val Val Pro Gly Tyr Phe Asp Leu Trp Gly Arg Gly Thr Leu
            100                 105                 110

Val Thr Val Ser Ser
        115


<210> SEQ ID NO 72
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 72

Gln Val Gln Leu Val Glu Ser Gly Gly Gly Val Val Gln Pro Gly Glu
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Glu Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Gln Asp Thr Ser Pro Asp Val Gly Ile Asp Tyr Trp
            100                 105                 110

Gly Gln Gly Thr Leu Val Thr Val Ser Ser
```

115 120

<210> SEQ ID NO 73
<211> LENGTH: 107
<212> TYPE: PRT
<213> ORGANISM: Artificial Sequence
<220> FEATURE:
<223> OTHER INFORMATION: Light chain variable region

<400> SEQUENCE: 73

Asp Ile Gln Met Thr Gln Ser Pro Ser Ser Leu Ser Ala Ser Val Gly
1 5 10 15

Asp Arg Ile Thr Ile Thr Cys Arg Ala Ser Arg Asp Ile Arg Asp Asp
20 25 30

Leu Ala Trp Tyr Gln Gln Lys Pro Gly Gly Ala Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Ser Asp Tyr Pro Leu
85 90 95

Thr Phe Gly Gly Gly Thr Lys Leu Glu Ile Lys
100 105

<210> SEQ ID NO 74
<211> LENGTH: 110
<212> TYPE: PRT
<213> ORGANISM: Artificial Sequence
<220> FEATURE:
<223> OTHER INFORMATION: Light chain variable region

<400> SEQUENCE: 74

Ser Ser Glu Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Thr Ser
85 90 95

Ser Thr Leu Val Phe Gly Gly Gly Thr Lys Val Thr Val Leu
100 105 110

<210> SEQ ID NO 75
<211> LENGTH: 111
<212> TYPE: PRT
<213> ORGANISM: Artificial Sequence
<220> FEATURE:
<223> OTHER INFORMATION: Light chain variable region

<400> SEQUENCE: 75

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

```
Asn Tyr Val Ser Trp Tyr Gln Lys His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Ala Asn Thr Ala Ser Leu Thr Ile Ser Gly Leu
65                  70                  75                  80

Gln Ala Glu Asp Glu Ala Asp Tyr Phe Cys Ser Ser Tyr Ser Ser Ser
                85                  90                  95

Ser Thr Leu Val Val Phe Gly Gly Gly Thr Lys Leu Thr Val Leu
            100                 105                 110


<210> SEQ ID NO 76
<211> LENGTH: 107
<212> TYPE: PRT
<213> ORGANISM: Artificial Sequence
<220> FEATURE:
<223> OTHER INFORMATION: Light chain variable region

<400> SEQUENCE: 76

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Leu Gly Tyr
            20                  25                  30

Val Asn Trp Tyr Gln Gln Lys Pro Gly Lys Ala Pro Ile Leu Leu Ile
        35                  40                  45

Tyr Ala Thr Ser Gly Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Asp Ile Lys
            100                 105


<210> SEQ ID NO 77
<211> LENGTH: 107
<212> TYPE: PRT
<213> ORGANISM: Artificial Sequence
<220> FEATURE:
<223> OTHER INFORMATION: Light chain variable region

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Met
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ile Asp Ser Tyr Pro Leu
                85                  90                  95

Thr Phe Gly Gly Gly Thr Lys Val Glu Ile Lys
            100                 105
```

<210> SEQ ID NO 78
<211> LENGTH: 107
<212> TYPE: PRT
<213> ORGANISM: Artificial Sequence
<220> FEATURE:
<223> OTHER INFORMATION: Light chain variable region

<400> SEQUENCE: 78

```
Asp Ile Gln Met Thr Gln Ser Pro Ser Ser Leu Ser Ala Ser Val Gly
1               5                   10                  15

Asp Thr Val Thr Ile Thr Cys Arg Ala Ser Gln Asn Ile Ser Pro Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 79
<211> LENGTH: 107
<212> TYPE: PRT
<213> ORGANISM: Artificial Sequence
<220> FEATURE:
<223> OTHER INFORMATION: Light chain variable region

<400> SEQUENCE: 79

```
Asp Ile Gln Met Thr Gln Ser Pro Ser Thr Leu Ser Ala Ser Val Gly
1               5                   10                  15

Asp Arg Val Thr Ile Thr Cys Arg Val Ser Gln Gly Ile Gly Asp Asp
            20                  25                  30

Leu Gly Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Phe Cys Gln Gln Ala His Ser Phe Pro Pro
                85                  90                  95

Thr Phe Gly Gly Gly Thr Lys Leu Glu Ile Lys
            100                 105
```

<210> SEQ ID NO 80
<211> LENGTH: 107
<212> TYPE: PRT
<213> ORGANISM: Artificial Sequence
<220> FEATURE:
<223> OTHER INFORMATION: Light chain variable region

<400> SEQUENCE: 80

```
Glu Thr Thr Leu Thr Gln Ser Pro Ser Thr Leu Ser Ala Ser Val Gly
1               5                   10                  15

Asp Arg Val Thr Ile Thr Cys Arg Ala Ser Glu Glu Ile Gly Ser Trp
            20                  25                  30

Leu Ala Trp Tyr Gln Gln Thr Pro Gly Lys Ala Pro Lys Arg Leu Ile
        35                  40                  45
```

```
Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Pro Pro
                85                  90                  95

Thr Phe Gly Gln Gly Thr Lys Val Glu Ile Lys
            100                 105


<210> SEQ ID NO 81
<211> LENGTH: 107
<212> TYPE: PRT
<213> ORGANISM: Artificial Sequence
<220> FEATURE:
<223> OTHER INFORMATION: Light chain variable region

<400> SEQUENCE: 81

Asp Ile Val Met Thr Gln Ser Pro Ser Thr Leu Ser Ala Ser Val Gly
1               5                   10                  15

Asp Arg Val Thr Val Thr Cys Arg Ala Ser Glu Asp Ile Gly Arg Trp
            20                  25                  30

Leu Ala Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Pro
                85                  90                  95

Thr Phe Gly Gln Gly Thr Lys Val Glu Ile Lys
            100                 105


<210> SEQ ID NO 82
<211> LENGTH: 110
<212> TYPE: PRT
<213> ORGANISM: Artificial Sequence
<220> FEATURE:
<223> OTHER INFORMATION: Light chain variable region

<400> SEQUENCE: 82

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Met Gly Ser Asn
            20                  25                  30

Pro Val Asn Trp Tyr Gln Gln Leu Pro Gly Glu Ala Pro Gln Leu Leu
        35                  40                  45

Met Tyr Asn Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Gly Leu
                85                  90                  95

Asn Gly Trp Val Phe Gly Gly Gly Thr Lys Leu Thr Val Leu
            100                 105                 110


<210> SEQ ID NO 83
<211> LENGTH: 107
<212> TYPE: PRT
```

<213> ORGANISM: Artificial Sequence
<220> FEATURE:
<223> OTHER INFORMATION: Light chain variable region

<400> SEQUENCE: 83

Ser Ser Glu Leu Thr Gln Asp Pro Ala Val Ser Val Ala Leu Gly Gln
1 5 10 15

Thr Val Ser Ile Thr Cys Gln Gly Asp Ser Leu Arg Ser Tyr Tyr Ala
20 25 30

Ser Trp Tyr Gln Gln Lys Pro Gly Gln Ala Pro Val Pro Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys His Ser Arg Asp Ser Ser Gly Lys Tyr
85 90 95

Val Phe Gly Val Gly Thr Lys Leu Thr Val Leu
100 105

<210> SEQ ID NO 84
<211> LENGTH: 107
<212> TYPE: PRT
<213> ORGANISM: Artificial Sequence
<220> FEATURE:
<223> OTHER INFORMATION: Light chain variable region

<400> SEQUENCE: 84

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Ser Pro Phe
20 25 30

Leu Asn Trp Tyr Gln Gln Lys Pro Gly Lys Ala Pro Lys Leu Leu Ile
35 40 45

Tyr Ala Ala Val Gly Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Thr Asp Tyr Pro Leu
85 90 95

Thr Phe Gly Gly Gly Thr Lys Val Glu Ile Lys
100 105

<210> SEQ ID NO 85
<211> LENGTH: 19
<212> TYPE: PRT
<213> ORGANISM: Artificial Sequence
<220> FEATURE:
<223> OTHER INFORMATION: Signal peptide sequence

<400> SEQUENCE: 85

Met Glu Phe Gly Leu Ser Trp Val Phe Leu Val Ala Ile Leu Lys Gly
1 5 10 15

Val Gln Cys

<210> SEQ ID NO 86
<211> LENGTH: 452
<212> TYPE: PRT
<213> ORGANISM: Artificial Sequence
<220> FEATURE:

<223> OTHER INFORMATION: Heavy chain of antibody M

<400> SEQUENCE: 86

Gln Val Gln Leu Val Glu Ser Gly Gly Gly Val Val Gln Pro Gly Glu
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Glu Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Gln Asp Thr Ser Pro Asp Val Gly Ile Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

```
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

```
<210> SEQ ID NO 87
<211> LENGTH: 214
<212> TYPE: PRT
<213> ORGANISM: Artificial Sequence
<220> FEATURE:
<223> OTHER INFORMATION: Light chain of antibody M

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Pro Phe
            20                  25                  30

Leu Asn Trp Tyr Gln Gln Lys Pro Gly Lys Ala Pro Lys Leu Leu Ile
        35                  40                  45

Tyr Ala Ala Val Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 88
<211> LENGTH: 330
<212> TYPE: PRT
<213> ORGANISM: Artificial Sequence
<220> FEATURE:
<223> OTHER INFORMATION: IgG1-Fc mutant sequence

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Tyr Leu Ser Leu Ser Pro Gly Lys
                325                 330


<210> SEQ ID NO 89
<211> LENGTH: 330
<212> TYPE: PRT
<213> ORGANISM: Artificial Sequence
<220> FEATURE:
<223> OTHER INFORMATION: IgG1-Fc mutant sequence

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Arg Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 90
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 90

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 91
<211> LENGTH: 107
<212> TYPE: PRT
<213> ORGANISM: Artificial Sequence
<220> FEATURE:
<223> OTHER INFORMATION: Light chain constant region

<400> SEQUENCE: 91

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 92
```

<211> LENGTH: 326
<212> TYPE: PRT
<213> ORGANISM: Artificial Sequence
<220> FEATURE:
<223> OTHER INFORMATION: A constant region of human IgG2 isotype

<400> SEQUENCE: 92

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ala Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly Lys
325

<210> SEQ ID NO 93
<211> LENGTH: 107
<212> TYPE: PRT
<213> ORGANISM: Artificial Sequence
<220> FEATURE:
<223> OTHER INFORMATION: A constant region of human IgG2 isotype

<400> SEQUENCE: 93

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 94
<211> LENGTH: 327
<212> TYPE: PRT
<213> ORGANISM: Artificial Sequence
<220> FEATURE:
<223> OTHER INFORMATION: A constant region of the human IgG4 isotype

<400> SEQUENCE: 94

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp

```
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 95
<211> LENGTH: 107
<212> TYPE: PRT
<213> ORGANISM: Artificial Sequence
<220> FEATURE:
<223> OTHER INFORMATION: A constant region of human IgG4 isotype

<400> SEQUENCE: 95

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 96
<211> LENGTH: 15
<212> TYPE: DNA
<213> ORGANISM: Artificial Sequence
<220> FEATURE:
<223> OTHER INFORMATION: Nucleotide sequence encoding VH CDR1

<400> SEQUENCE: 96

tcctacggca tgcac                                                      15


<210> SEQ ID NO 97
<211> LENGTH: 51
<212> TYPE: DNA
<213> ORGANISM: Artificial Sequence
<220> FEATURE:
<223> OTHER INFORMATION: Nucleotide sequence encoding VH CDR2

<400> SEQUENCE: 97

gtgatctggg aggatggctc caaccagtac tatgccgaca gcgtgaaggg a              51


<210> SEQ ID NO 98
<211> LENGTH: 39
<212> TYPE: DNA
<213> ORGANISM: Artificial Sequence
<220> FEATURE:
<223> OTHER INFORMATION: Nucleotide sequence encoding VH CDR3
```

<400> SEQUENCE: 98
gacaaccaag acaccagccc cgacgtgggc atcgattat 39

<210> SEQ ID NO 99
<211> LENGTH: 33
<212> TYPE: DNA
<213> ORGANISM: Artificial Sequence
<220> FEATURE:
<223> OTHER INFORMATION: Nucleotide sequence encoding VL CDR1

<400> SEQUENCE: 99
agagccagcc agaacatctc cccctttctg aat 33

<210> SEQ ID NO 100
<211> LENGTH: 21
<212> TYPE: DNA
<213> ORGANISM: Artificial Sequence
<220> FEATURE:
<223> OTHER INFORMATION: Nucleotide sequence encoding VL CDR2

<400> SEQUENCE: 100
gccgctgtgg gactgcagag c 21

<210> SEQ ID NO 101
<211> LENGTH: 27
<212> TYPE: DNA
<213> ORGANISM: Artificial Sequence
<220> FEATURE:
<223> OTHER INFORMATION: Nucleotide sequence encoding VL CDR3

<400> SEQUENCE: 101
cagcagtata ccgactaccc tctgacc 27

<210> SEQ ID NO 102
<211> LENGTH: 366
<212> TYPE: DNA
<213> ORGANISM: Artificial Sequence
<220> FEATURE:
<223> OTHER INFORMATION: Nucleotide sequence encoding heavy chain variable region

<400> SEQUENCE: 102
caagtgcagc tggtggagag cggaggagga gtggtgcaac ccggcgagtc cctcagactg 60
agctgtgccg ccagcggctt caccttcagc tcctacggca tgcactgggt gagacaagcc 120
cccggcaaag gactggagtg ggtggccgtg atctgggagg atggctccaa ccagtactat 180
gccgacagcg tgaagggaag attcaccatc tctagagaca actccaagaa cacactgtat 240
ctgcagatga actctctgag ggccgaggac accgccgtgt actactgcgc caaggacaac 300
caagacacca gccccgacgt gggcatcgat tattggggcc agggtaccct ggttaccgtt 360
agcagc 366

<210> SEQ ID NO 103
<211> LENGTH: 321
<212> TYPE: DNA
<213> ORGANISM: Artificial Sequence
<220> FEATURE:
<223> OTHER INFORMATION: Nucleotide sequence encoding light chain variable region

<400> SEQUENCE: 103
gacatccaga tgacccagag ccctagctct ctgtccgcta gcgtgggaga tagagtgacc 60

```
atcacatgca gagccagcca gaacatctcc ccctttctga attggtatca gcagaagccc    120

ggcaaggccc ctaagctgct gatctatgcc gctgtgggac tgcagagcgg agtgccttcc    180

agattctccg gcagcggcag cggaaccgac ttcacactga ccatcagctc tctgcagccc    240

gaggacttcg ccacctacta ctgccagcag tataccgact accctctgac cttcggaggc    300

ggcaccaagg tggagatcaa g                                              321


<210> SEQ ID NO 104
<211> LENGTH: 8
<212> TYPE: PRT
<213> ORGANISM: Artificial Sequence
<220> FEATURE:
<223> OTHER INFORMATION: VH CDR1

<400> SEQUENCE: 104

Gly Phe Thr Phe Ser Ser Tyr Gly
1               5


<210> SEQ ID NO 105
<211> LENGTH: 990
<212> TYPE: DNA
<213> ORGANISM: Artificial Sequence
<220> FEATURE:
<223> OTHER INFORMATION: Nucleotide sequence encoding heavy chain
      constant region

<400> SEQUENCE: 105

gcgagcacca aaggcccgag cgtgtttccg ctggccccga gcagcaaaag caccagcggt     60

ggcaccgcag cgctgggttg cctggtgaaa gattatttcc cggaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990


<210> SEQ ID NO 106
<211> LENGTH: 321
<212> TYPE: DNA
<213> ORGANISM: Artificial Sequence
<220> FEATURE:
<223> OTHER INFORMATION: Nucleotide sequence encoding light chain
      constant region

<400> SEQUENCE: 106
```

-continued

```
cgtacggtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg t                                              321
```

DEVELOPMENT AND APPLICATION OF IMMUNE CELL ACTIVATOR

CROSS-REFERENCE TO RELATED APPLICATIONS

This application is a Section 371 of International Application No. PCT/CN2021/081993, filed Mar. 22, 2021, which was published in the Chinese language on Sep. 30, 2021 under International Publication No. WO 2021/190431 A1, which claims priority under 35 U.S.C. § 119 (b) to Chinese Application No. 202010208900.0, filed Mar. 23, 2020, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689755_7US_Sequence_Listing", creation date of Sep. 21, 2022, and having a size of 63,369 bytes. The sequence listing submitted via EFS-Web is part of the specification and is herein incorporated by reference in its entirety.

TECHNICAL FIELD

The present invention relates to the technical field of bio-immunology, and particularly relates to a novel antibody or a fragment thereof that specifically bind to OX40.

BACKGROUND

There are two types of checkpoints in the immune system. One is inhibitory, such as PD-1, and the other is activating, such as OX40. The complete activation of T cells in the immune system requires two-step signals. The first signal is generated by the recognition of an antigen through a T cell antigen receptor, and the activation signal is transduced into a cell via a CD3 molecule. The second signal, known as a co-stimulatory signal, is generated by the interaction of co-stimulatory molecules on the surface of an antigen-presenting cell or a target cell and co-stimulatory molecule receptors on the surface of an activated T cell. The co-stimulatory signals promote proliferation of antigen-specific T cells and differentiation thereof into effector T cells. (Lindsay K et al., *Immunity,* 2016, 44 (5): 1005-1019).

OX40, also known as TNFRSF4, ACT35, CD134, etc., belongs to the tumor necrosis factor receptor superfamily (TNFRSF), and is also a type I transmembrane glycoprotein. OX40 is not expressed on resting T cells but on activated CD4+ T cells, CD8+ T cells, NK cells and NKT cells (Paterson D J et al., *Mol. Immunol.,* 1987; 24:1281-1290). T cells, after being activated by antigens, highly express OX40 molecules within 1-3 days, and the activation of OX40 signals further enhances T cell activation signals to enhance immune system responses (Gramaglia I et al., *J. Immunol.* 2000; 165:3043-3050).

OX40L, also known as TNFSF4, TXGP1, gp34 and CD252, is a type II transmembrane glycoprotein and a natural ligand for OX40. It is present on activated antigen-presenting cells (APCs) such as DC cells and B cells in a trimer form, and its expression is mediated by CD40, toll-like receptors (TLRs) and inflammatory factors. OX40L is also widely present in non-hematopoietic cells such as smooth muscle cells and vascular endothelial cells (Murata K et al., *J. Immunol.* 2002; 169:4628-4636).

Intracellular signaling pathways of OX40 activated by OX40L are associated with multiple intracellular signaling pathways of T cells, and the intracellular signaling pathways of OX40 can be initially activated by the binding of OX40L trimer formed by intramolecular disulfide bonds to OX40 on the cell membranes of T cells (Compaan D M et al., *Structure.* 2006; 14:1321-30). For the further or complete activation of OX40 intracellular signals, further oligomerization of the receptors is required to form hexamers or above (H Wajant. *Cell Death and Differentiation*, (2015) 22, 1727-1741). When activated, OX40 recruits TNF receptor-associated factor (TRAF) 2 and 5 through its intracellular domain, so that signaling pathways of NFκB are activated to exert the effect of anti-apoptosis, thus suppressing the apoptosis of cells (Song J et al., *J. Immunol.* 2008; 180:7240-8).

In addition, the intracellular signaling pathways of OX40 also specifically assist TCR intracellular signaling pathways of T cells, mainly PKB/PI3K and calcium-associated NFAT signaling pathways, wherein the PKB/PI3K signaling pathways promote the survival of activated T cells and the cell cycle progression (Song J et al., *Nat Immunol.* 2004; 5:150-8), and the calcium-associated NFAT signaling pathways promote the proliferation of activated T cells and the secretion of corresponding cytokines (So T et al., *Proc Natl Acad Sci USA.* 2006; 103:3740-5).

Researchers have found that OX40 is also highly expressed on tumor-infiltrating CD4+ Treg cells (regulatory T cells). Treg cells can suppress effector T cells (Teff). At present, there is no consensual and determined view on the regulatory role of the OX40 signaling pathways on the function of Treg cells. Some studies have shown that the OX40 signaling pathways can inhibit the immunosuppressive function of Treg cells (Piconese S et al., *J. Exp. Med.* 2008; 205:825-39; Voo K S et al., *J. Immunol.* 2013; 191:3641-50), while others have shown that OX40 is necessary for Treg cells to completely exert the immunosuppressive function thereof (Piconese S et al., *Eur. J. Immunol.* 2010; 40:2902-13; Griseri T et al., *J. Exp. Med.* 2010; 207:699-709). The effect of the OX40 intracellular signaling pathways on the proliferation and apoptosis of Treg cells varies with the microenvironment in which the cells are placed. It has also been found that the activation of OX40 strongly promotes the proliferation of Treg cells in the absence of IFN-γ and IL-4 or in the presence of FoxP3 expression (Ruby C E et al., *J. Immunol.* 2009; 183:4853-7), while the activation of OX40 does not affect the proliferation of Treg cells in other microenvironments (Vu M D et al., *Blood.* 2007; 110:2501-10).

At present, it is widely believed that anti-OX40 antibodies activate T cells in the immune system and inhibit tumors mainly through the following three cell physiological mechanisms: the first one is directly activating CD4+ and CD8+ effector T cells to promote their proliferation and survival and the secretion of related inflammatory factors; the second one is inhibiting the signals and activities of Treg cells to weaken their inhibitory effect on the immune system; the third one is depleting Treg cells by ADCC, ADCP or the like to reduce their suppression on Teff cells (J. Willoughby et al., *Molecular Immunology* 83, 2017, 13-22).

The concept of using anti-OX40 antibodies or signaling pathways of OX40 to treat tumors has been strongly verified on a large number of mouse tumor models. According to the existing researches, it is strongly indicated that OX40 is a very promising activating target in tumor immunotherapy and it can provide a new means for tumor immunotherapy.

SUMMARY

The present invention provides a novel antibody or a fragment thereof that can specifically recognize and bind to OX40 (particularly human OX40 (hOX40)), wherein the antibody or the fragment thereof can bind to hOX40 with a higher affinity without competing with OX40 ligand (OX40L), can more effectively activate T cells, generate stronger immune responses, and improve anti-tumor activity.

The present invention discloses an antibody or an antigen-binding fragment thereof that specifically binds to OX40, which comprises one or more amino acid sequences in (a) (f):

(a) a VH CDR1 set forth in SEQ ID NO: 1, 4, 10, 16, 104 or 22;

(b) a VH CDR2 set forth in SEQ ID NO: 2, 5, 7, 8, 11, 13, 14, 17, 20, 23 or 26;

(c) a VH CDR3 set forth in SEQ ID NO: 3, 6, 9, 12, 15, 18, 21, 24 or 27;

(d) a VL CDR1 set forth in SEQ ID NO: 28, 31, 37, 40, 43, 46, 49, 52, 55, 58 or 61;

(e) a VL CDR2 set forth in SEQ ID NO: 19, 25, 29, 32, 35, 38, 44, 47, 50, 56, 59 or 62; and (f) a VL CDR3 set forth in SEQ ID NO: 30, 33, 34, 36, 39, 41, 42, 45, 48, 51, 53, 54, 57, 60 or 63.

In some embodiments, the antibody or the fragment thereof comprises a VH CDR1 set forth in SEQ ID NO: 1, 4, 10, 16, 104 or 22. In some embodiments, the antibody or the fragment thereof comprises a VH CDR2 set forth in SEQ ID NO: 2, 5, 7, 8, 11, 13, 14, 17, 20, 23 or 26. In some embodiments, the antibody or the fragment thereof comprises a VH CDR3 set forth in SEQ ID NO: 3, 6, 9, 12, 15, 18, 21, 24 or 27. In some embodiments, the antibody or the fragment thereof comprises a VL CDR1 set forth in SEQ ID NO: 28, 31, 37, 40, 43, 46, 49, 52, 55, 58 or 61. In some embodiments, the antibody or the fragment thereof comprises a VL CDR2 set forth in SEQ ID NO: 19, 25, 29, 32, 35, 38, 44, 47, 50, 56, 59 or 62. In some embodiments, the antibody or the fragment thereof comprises a VL CDR3 set forth in SEQ ID NO: 30, 33, 34, 36, 39, 41, 42, 45, 48, 51, 53, 54, 57, 60 or 63.

In some embodiments, the antibody or the fragment thereof comprises a VH CDR1 set forth in SEQ ID NO: 10. In some embodiments, the antibody or the fragment thereof comprises a VH CDR2 set forth in SEQ ID NO: 7, 11, 13 or 26. In some embodiments, the antibody or the fragment thereof comprises a VH CDR3 set forth in SEQ ID NO: 12 or 27. In some embodiments, the antibody or the fragment thereof comprises a VL CDR1 set forth in SEQ ID NO: 37, 43 or 61. In some embodiments, the antibody or the fragment thereof comprises a VL CDR2 set forth in SEQ ID NO: 19, 25, 38, 44 or 62. In some embodiments, the antibody or the fragment thereof comprises a VL CDR3 set forth in SEQ ID NO: 34, 39, 41, 45, 53 or 63.

In some embodiments, the antibody or the fragment thereof comprises: a VH CDR1 set forth in SEQ ID NO: 1, 4, 10, 16, 104 or 22; a VH CDR2 set forth in SEQ ID NO: 2, 5, 7, 8, 11, 13, 14, 17, 20, 23 or 26; and a VH CDR3 set forth in SEQ ID NO: 3, 6, 9, 12, 15, 18, 21, 24 or 27. In some embodiments, the antibody or the fragment thereof comprises: a VL CDR1 set forth in SEQ ID NO: 28, 31, 37, 40, 43, 46, 49, 52, 55, 58 or 61; a VL CDR2 set forth in SEQ ID NO: 19, 25, 29, 32, 35, 38, 44, 47, 50, 56, 59 or 62; and a VL CDR3 set forth in SEQ ID NO: 30, 33, 34, 36, 39, 41, 42, 45, 48, 51, 53, 54, 57, 60 or 63.

In some embodiments, the antibody or the fragment thereof comprises: a VH CDR1 set forth in SEQ ID NO: 1, 4, 10, 16, 104 or 22; a VH CDR2 set forth in SEQ ID NO: 2, 5, 7, 8, 11, 13, 14, 17, 20, 23 or 26; a VH CDR3 set forth in SEQ ID NO: 3, 6, 9, 12, 15, 18, 21, 24 or 27; a VL CDR1 set forth in SEQ ID NO: 28, 31, 37, 40, 43, 46, 49, 52, 55, 58 or 61; a VL CDR2 set forth in SEQ ID NO: 19, 25, 29, 32, 35, 38, 44, 47, 50, 56, 59 or 62; and a VL CDR3 set forth in SEQ ID NO: 30, 33, 34, 36, 39, 41, 42, 45, 48, 51, 53, 54, 57, 60 or 63.

In some embodiments, the antibody or the fragment thereof comprises: a VH CDR1 set forth in SEQ ID NO: 10; a VH CDR2 set forth in SEQ ID NO: 7, 11, 13 or 26; a VH CDR3 set forth in SEQ ID NO: 12 or 27; a VL CDR1 set forth in SEQ ID NO: 37, 43 or 61; a VL CDR2 set forth in SEQ ID NO: 19, 25, 38, 44 or 62; and a VL CDR3 set forth in SEQ ID NO: 34, 39, 41, 45, 53 or 63.

In some embodiments, the antibody or the fragment thereof comprises: a VH CDR1 set forth in SEQ ID NO: 1; a VH CDR2 set forth in SEQ ID NO: 2; a VH CDR3 set forth in SEQ ID NO: 3; a VL CDR1 set forth in SEQ ID NO: 28; a VL CDR2 set forth in SEQ ID NO: 29; and a VL CDR3 set forth in SEQ ID NO: 30.

In some embodiments, the antibody or the fragment thereof comprises: a VH CDR1 set forth in SEQ ID NO: 4; a VH CDR2 set forth in SEQ ID NO: 5; a VH CDR3 set forth in SEQ ID NO: 6; a VL CDR1 set forth in SEQ ID NO: 31; a VL CDR2 set forth in SEQ ID NO: 32; and a VL CDR3 set forth in SEQ ID NO: 33.

In some embodiments, the antibody or the fragment thereof comprises: a VH CDR1 set forth in SEQ ID NO: 1; a VH CDR2 set forth in SEQ ID NO: 8; a VH CDR3 set forth in SEQ ID NO: 9; a VL CDR1 set forth in SEQ ID NO: 31; a VL CDR2 set forth in SEQ ID NO: 35; and a VL CDR3 set forth in SEQ ID NO: 36.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 12; a VL CDR1 set forth in SEQ ID NO: 37; a VL CDR2 set forth in SEQ ID NO: 38; and a VL CDR3 set forth in SEQ ID NO: 39.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 12; a VL CDR1 set forth in SEQ ID NO: 40; a VL CDR2 set forth in SEQ ID NO: 29; and a VL CDR3 set forth in SEQ ID NO: 42.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 12; a VL CDR1 set forth in SEQ ID NO: 43; a VL CDR2 set forth in SEQ ID NO: 44; and a VL CDR3 set forth in SEQ ID NO: 39.

In some embodiments, the antibody or the fragment thereof comprises: a VH CDR1 set forth in SEQ ID NO: 10; a VH CDR2 set forth in SEQ ID NO: 26; a VH CDR3 set forth in SEQ ID NO: 27; a VL CDR1 set forth in SEQ ID NO: 61; a VL CDR2 set forth in SEQ ID NO: 25; and a VL CDR3 set forth in SEQ ID NO: 34.

In some embodiments, the antibody or the fragment thereof comprises: a VH CDR1 set forth in SEQ ID NO: 10; a VH CDR2 set forth in SEQ ID NO: 14; a VH CDR3 set forth in SEQ ID NO: 15; a VL CDR1 set forth in SEQ ID NO: 46; a VL CDR2 set forth in SEQ ID NO: 47; and a VL CDR3 set forth in SEQ ID NO: 48.

In some embodiments, the antibody or the fragment thereof comprises: a VH CDR1 set forth in SEQ ID NO: 16;

a VH CDR2 set forth in SEQ ID NO: 17; a VH CDR3 set forth in SEQ ID NO: 18; a VL CDR1 set forth in SEQ ID NO: 49; a VL CDR2 set forth in SEQ ID NO: 50; and a VL CDR3 set forth in SEQ ID NO: 51.

In some embodiments, the antibody or the fragment thereof comprises: a VH CDR1 set forth in SEQ ID NO: 16; a VH CDR2 set forth in SEQ ID NO: 17; a VH CDR3 set forth in SEQ ID NO: 18; a VL CDR1 set forth in SEQ ID NO: 52; a VL CDR2 set forth in SEQ ID NO: 29; and a VL CDR3 set forth in SEQ ID NO: 54.

In some embodiments, the antibody or the fragment thereof comprises: a VH CDR1 set forth in SEQ ID NO: 1; a VH CDR2 set forth in SEQ ID NO: 20; a VH CDR3 set forth in SEQ ID NO: 21; a VL CDR1 set forth in SEQ ID NO: 55; a VL CDR2 set forth in SEQ ID NO: 56; and a VL CDR3 set forth in SEQ ID NO: 57.

In some embodiments, the antibody or the fragment thereof comprises: a VH CDR1 set forth in SEQ ID NO: 22; a VH CDR2 set forth in SEQ ID NO: 23; a VH CDR3 set forth in SEQ ID NO: 24; a VL CDR1 set forth in SEQ ID NO: 58; a VL CDR2 set forth in SEQ ID NO: 59; and a VL CDR3 set forth in SEQ ID NO: 60.

In some embodiments, the antibody or the fragment thereof comprises: a VH CDR1 set forth in SEQ ID NO: 10; a VH CDR2 set forth in SEQ ID NO: 26; a VH CDR3 set forth in SEQ ID NO: 27; a VL CDR1 set forth in SEQ ID NO: 61; a VL CDR2 set forth in SEQ ID NO: 62; and a VL CDR3 set forth in SEQ ID NO: 63.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 27; a VL CDR1 set forth in SEQ ID NO: 61; a VL CDR2 set forth in SEQ ID NO: 62; and a VL CDR3 set forth in SEQ ID NO: 34.

In some embodiments, the antibody or the fragment thereof comprises: a VH CDR1 set forth in SEQ ID NO: 10; a VH CDR2 set forth in SEQ ID NO: 26; a VH CDR3 set forth in SEQ ID NO: 27; a VL CDR1 set forth in SEQ ID NO: 61; a VL CDR2 set forth in SEQ ID NO: 44; and a VL CDR3 set forth in SEQ ID NO: 39.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 12; a VL CDR1 set forth in SEQ ID NO: 61; a VL CDR2 set forth in SEQ ID NO: 25; and a VL CDR3 set forth in SEQ ID NO: 34.

In some embodiments, the antibody or the fragment thereof comprises: a VH CDR1 set forth in SEQ ID NO: 10; a VH CDR2 set forth in SEQ ID NO: 26; a VH CDR3 set forth in SEQ ID NO: 27; a VL CDR1 set forth in SEQ ID NO: 61; a VL CDR2 set forth in SEQ ID NO: 25; and a VL CDR3 set forth in SEQ ID NO: 39.

In some embodiments, the antibody or the fragment thereof comprises: a VH CDR1 set forth in SEQ ID NO: 10; a VH CDR2 set forth in SEQ ID NO: 26; a VH CDR3 set forth in SEQ ID NO: 27; a VL CDR1 set forth in SEQ ID NO: 61; a VL CDR2 set forth in SEQ ID NO: 44; and a VL CDR3 set forth in SEQ ID NO: 34.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 27; a VL CDR1 set forth in SEQ ID NO: 61; a VL CDR2 set forth in SEQ ID NO: 25; and a VL CDR3 set forth in SEQ ID NO: 39.

In some embodiments, the antibody or the fragment thereof comprises: a VH CDR1 set forth in SEQ ID NO: 10; a VH CDR2 set forth in SEQ ID NO: 11; a VH CDR3 set forth in SEQ ID NO: 27; a VL CDR1 set forth in SEQ ID NO: 61; a VL CDR2 set forth in SEQ ID NO: 44; and a VL CDR3 set forth in SEQ ID NO: 34.

In some embodiments, the antibody or the fragment thereof comprises a heavy chain variable region comprising an amino acid sequence set forth in SEQ ID NO: 64, 65, 66, 67, 68, 69, 70, 71 or 72, or an amino acid sequence having at least 90%, at least 91%, at least 92%, at least 93%, at least 94%, at least 95%, at least 96%, at least 97%, at least 98% or at least 99% sequence homology to the amino acid sequence set forth in SEQ ID NO: 64, 65, 66, 67, 68, 69, 70, 71 or 72.

In some embodiments, the antibody or the fragment thereof comprises a heavy chain variable region comprising an amino acid sequence set forth in SEQ ID NO: 67 or 72, or an amino acid sequence having at least 90%, at least 91%, at least 92%, at least 93%, at least 94%, at least 95%, at least 96%, at least 97%, at least 98% or at least 99% sequence homology to the amino acid sequence set forth in SEQ ID NO: 67 or 72.

In some embodiments, the antibody or the fragment thereof comprises a light chain variable region comprising an amino acid sequence set forth in SEQ ID NO: 73, 74, 75, 76, 77, 78, 79, 80, 81, 82, 83 or 84, or an amino acid sequence having at least 90%, at least 91%, at least 92%, at least 93%, at least 94%, at least 95%, at least 96%, at least 97%, at least 98% or at least 99% sequence homology to the amino acid sequence set forth in SEQ ID NO: 73, 74, 75, 76, 77, 78, 79, 80, 81, 82, 83 or 84.

In some embodiments, the antibody or the fragment thereof comprises a light chain variable region comprising an amino acid sequence set forth in SEQ ID NO: 76, 78 or 84, or an amino acid sequence having at least 90%, at least 91%, at least 92%, at least 93%, at least 94%, at least 95%, at least 96%, at least 97%, at least 98% or at least 99% sequence homology to the amino acid sequence set forth in SEQ ID NO: 76, 78 or 84.

In some embodiments, the antibody or the fragment thereof comprises a heavy chain variable region set forth in SEQ ID NO: 72 and a light chain variable region set forth in SEQ ID NO: 84.

In some embodiments, the antibody or the fragment thereof is of one of the isotypes IgG, IgM, IgA, IgE and IgD.

In some embodiments, the antibody or the fragment thereof is of the IgG isotype; in some embodiments, the antibody or the fragment thereof is of the IgG1 isotype, IgG2 isotype, IgG3 isotype or IgG4 isotype. Without limitation, the antibody or the fragment thereof is a chimeric antibody, a humanized antibody or a fully human antibody. In a certain aspect, the antibody or the fragment thereof is a humanized antibody.

In some embodiments, the antibody or the fragment thereof further comprises a heavy chain constant region, a light chain constant region, an Fc region, or a combination thereof.

In some embodiments, the antibody described herein is of the IgG isotype. In some embodiments, the constant region of the antibody is of the human IgG1 isotype, and includes a heavy chain constant region comprising an amino acid sequence set forth in SEQ ID NO: 90 and a light chain constant region comprising an amino acid sequence set forth in SEQ ID NO: 91.

In some embodiments, the constant region of the antibody is of the human IgG2 isotype, and includes a heavy chain constant region comprising an amino acid sequence set forth in SEQ ID NO: 92 and a light chain constant region comprising an amino acid sequence set forth in SEQ ID NO: 93.

In some embodiments, the constant region of the antibody is of the human IgG4 isotype, and includes a heavy chain constant region comprising an amino acid sequence set forth in SEQ ID NO: 94 and a light chain constant region comprising an amino acid sequence set forth in SEQ ID NO: 95.

In some embodiments, the Fc region is an Fc region of a human antibody. In some embodiments, a heavy chain of the human Fc region comprises an amino acid R at position 345 (E345R) (Eu numbering). In some embodiments, a heavy chain of the human Fc region comprises an amino acid Y at position 440 (S440Y) (Eu numbering). In some embodiments, the human Fc region comprises an amino acid sequence set forth in SEQ ID NO: 88 or SEQ ID NO: 89.

In some embodiments, the heavy chain constant region comprises an amino acid sequence set forth in SEQ ID NO: 88, 89 or 90, and/or the light chain constant region comprises an amino acid sequence set forth in SEQ ID NO: 91. In some embodiments, the heavy chain constant region comprises an amino acid sequence set forth in SEQ ID NO: 90, and/or the light chain constant region comprises an amino acid sequence set forth in SEQ ID NO: 91.

In some embodiments, the antibody or the fragment thereof is a chimeric antibody or a fragment thereof, a humanized antibody or a fragment thereof, or a fully human antibody or a fragment thereof.

In some embodiments, the antibody comprises a heavy chain and a light chain, wherein the heavy chain comprises an amino acid sequence set forth in SEQ ID NO: 86 or an amino acid sequence having at least 90%, at least 91%, at least 92%, at least 93%, at least 94%, at least 95%, at least 96%, at least 97%, at least 98% or at least 99% sequence homology to the amino acid sequence set forth in SEQ ID NO: 86; and the light chain comprises an amino acid sequence set forth in SEQ ID NO: 87 or an amino acid sequence having at least 90%, at least 91%, at least 92%, at least 93%, at least 94%, at least 95%, at least 96%, at least 97%, at least 98% or at least 99% sequence homology to the amino acid sequence set forth in SEQ ID NO: 87.

In some embodiments, the antibody comprises a heavy chain set forth in SEQ ID NO: 86 and a light chain set forth in SEQ ID NO: 87.

In some embodiments, the antibody or the fragment thereof can specifically recognize and bind to human OX40 or rhesus monkey OX40.

In some embodiments, the antibody or the fragment thereof activates, enhances or induces activity of OX40.

In some embodiments, the antibody or the fragment thereof can activate T cells.

In some embodiments, the antibody or the antigen-binding fragment thereof promotes further activation of activated T cells, resulting in secretion of more inflammatory factors.

In some embodiments, the antibody or the antigen-binding fragment thereof can activate an intracellular signaling pathway of OX40.

In some embodiments, the antibody or the fragment thereof has an affinity value $K_D$ of ≤5 nM for OX40. In some embodiments, the antibody or the fragment thereof has an affinity value $K_D$ of ≤3.5 nM for OX40. In some embodiments, the antibody or the fragment thereof has an affinity value $K_D$ of ≤2 nM for OX40. In some embodiments, the antibody or the fragment thereof has an affinity value $K_D$ of ≤1 nM for OX40. In some embodiments, the antibody or the fragment thereof has an affinity value $K_D$ of ≤0.2 nM for OX40.

In some embodiments, the antibody or the fragment thereof is a monoclonal antibody or a fragment thereof.

In some embodiments, the antibody or the fragment thereof is expressed in CHO cells.

In some embodiments, the antibody or the fragment thereof is expressed in a CHO cell with an edited genome, wherein an antibody or a fragment thereof with a low content of fucose or without fucose is expressed in the CHO cell. In some embodiments, the CHO cell with an edited genome is a CHO cell in which one or more of the following genes are reduced or knocked out: the α-1,6-fucosyltransferase 8 gene (fut8 gene), the GDP-mannose 4,6-dehydratase (GMD) gene, the GDP-4-keto-6-deoxymannose-3,5-epimerase-4-reductase (GMER) gene and the GDP-fucose transporter (GFT) gene (e.g., Slc35c1 gene). In some embodiments, the antibody or the fragment thereof is expressed in a CHO cell in which the fut8 gene is knocked out.

In some embodiments, the antibody or the fragment thereof has one, two or three amino acid residues modified by fucose.

In some embodiments, in the antibody or the fragment thereof, the content of fucose is no more than 10%. In some embodiments, in the antibody or the fragment thereof, the content of fucose is no more than 5%. In some embodiments, in the antibody or the fragment thereof, the content of fucose is no more than 1%. In some embodiments, in the antibody or the fragment thereof, the content of fucose is no more than 0.5%. In some embodiments, the antibody or the fragment thereof does not bind to fucose.

In some embodiments, the antibody or the fragment thereof is an isolated antibody or an antigen-binding fragment thereof.

In some embodiments, the present invention also provides a polynucleotide encoding the antibody or the fragment thereof. In some embodiments, the polynucleotide is an isolated polynucleotide.

In some embodiments, the polynucleotide comprises one or more nucleotide sequences set forth in SEQ ID NOs: 96-101. In some embodiments, the polynucleotide comprises nucleotide sequences set forth in SEQ ID NOs: 96, 97 and 98. In some embodiments, the polynucleotide comprises nucleotide sequences set forth in SEQ ID NOs: 99, 100 and 101. In some embodiments, the polynucleotide comprises a nucleotide sequence set forth in SEQ ID NO: 102. In some embodiments, the polynucleotide comprises a nucleotide sequence set forth in SEQ ID NO: 103. In some embodiments, the polynucleotide comprises a nucleotide sequence set forth in SEQ ID NO: 102 and/or a nucleotide sequence set forth in SEQ ID NO: 103.

In some embodiments, the present invention further provides a vector comprising one or more polynucleotides encoding the antibody or the fragment thereof. In some embodiments, the vector is an isolated vector. In some embodiments, the vector is an expression vector, including a plasmid or a virus.

In some embodiments, the present invention further provides a cell comprising one or more polynucleotides encoding the antibody or the fragment thereof. In some embodiments, the cell is an isolated cell. In some embodiments, the cell is a CHO cell. In some embodiments, the cell comprises the vector. In some embodiments, one or more genes of the cell are edited, so that an antibody or a fragment thereof with a low content of fucose or without fucose is expressed in the CHO cell. In some embodiments, the CHO cell with an edited genome is a CHO cell in which one or more of the following genes are reduced or knocked out: the Slc35c1 gene, the fut8 gene, the GDP-mannose 4,6-dehydratase (GMD) gene, the GDP-4-keto-6-deoxymannose-3,5-epimerase-4-reductase (GMER) gene and the GDP-fucose transporter (GFT) gene.

In some embodiments, the present invention further provides a composition comprising the antibody or the fragment thereof, the polynucleotide or the cell, and a pharmaceutically acceptable carrier.

In some embodiments, the present invention further provides a method for treating a cancer or an infection in a patient in need, which comprises administering to the patient an effective dose of the antibody or the fragment thereof. In some embodiments, the present invention further provides use of the antibody or the fragment thereof described herein in treating a cancer or an infection. In some embodiments, the present invention further provides use of the antibody or the fragment thereof described herein in preparing a medicament for treating a cancer or an infection. In some embodiments, the cancer is a solid tumor.

In some embodiments, the cancer is selected from non-Hodgkin's lymphoma (NHL), acute lymphocytic leukemia (ALL), acute myelogenous leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, etc. Solid tumors include, for example, breast cancer, ovarian cancer, lung cancer, prostate cancer, melanoma, colorectal cancer, head and neck cancer, bladder cancer, esophageal cancer, liver cancer and renal cancer.

In some embodiments, the method further comprises administering to the patient a second cancer therapeutic agent.

In some embodiments, the infection is a viral infection, a bacterial infection, a fungal infection or a parasitic infection.

In some embodiments, the present invention further provides a method for treating a cancer or an infection in a patient in need, which comprises: (a) treating a cell with the antibody or the fragment thereof described herein in vitro; and (b) administering to the patient the treated cell. In some embodiments, the method further comprises isolating the cell from an individual prior to step (a). In some embodiments, the cell is isolated from the patient. In some embodiments, the cell is isolated from a donor individual different from the patient.

In some embodiments, the cell is a T cell. In some embodiments, the T cell is a tumor infiltrating T lymphocyte, a CD4+ T cell, a CD8+ T cell, or a combination thereof.

In some embodiments, the present invention further provides a method for detecting OX40 expression in a sample, which comprises contacting the sample with the antibody or the fragment thereof described herein to allow the antibody or the fragment thereof to bind to OX40, and detecting the binding that reflects the OX40 expression in the sample. In some embodiments, the sample comprises a tumor cell, a tumor tissue, an infected tissue or a blood sample.

In some embodiments, the present invention further provides a method for treating a disease requiring an enhanced immune function in a patient in need, which comprises administering to the patient an effective dose of the antibody or the fragment thereof.

The present invention provides an antibody or a fragment thereof that binds to human OX40 or rhesus monkey OX40, wherein an anti-OX40 antibody or a fragment thereof of the present invention retains strong binding to human OX40 or rhesus monkey OX40.

DETAILED DESCRIPTION

Definitions

Figure 1:
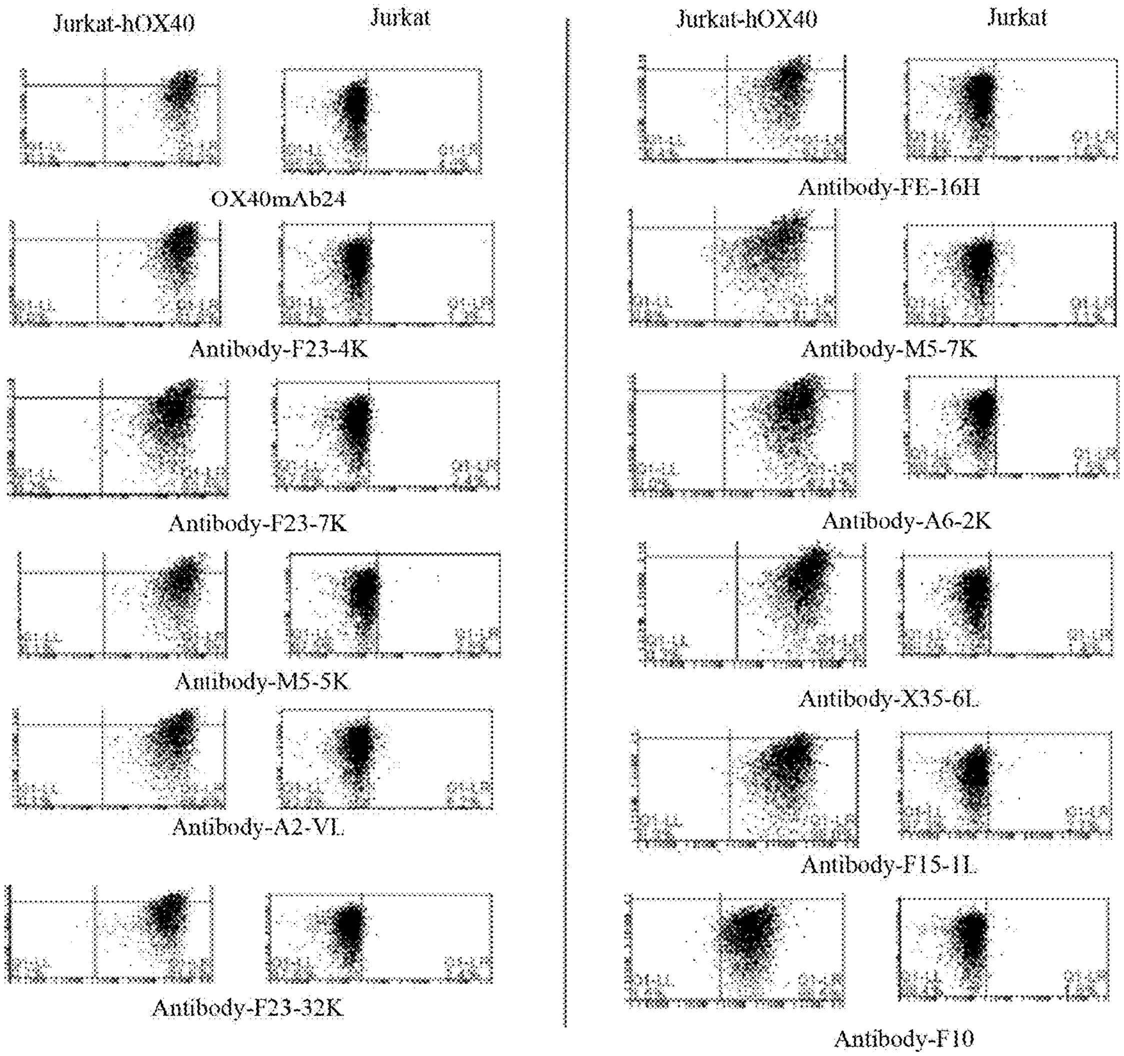
FIG. 1 shows flow cytometric patterns demonstrating the binding of candidate antibodies to Jurkatx cells highly expressing OX40, where the X-axis represents the fluorescence intensity of 50 nM hOX40-FC binding.

Unless otherwise defined, scientific and technical terms used in the present invention have the meanings that are commonly understood by those skilled in the art. Generally, the nomenclature and techniques used in cell culture, molecular biology and protein purification described herein are well known and commonly used in the art. Standard techniques are used for recombinant DNA, oligonucleotide synthesis and cell culture and transformation (e.g., electroporation and lipofection). Enzymatic reactions and purification techniques are performed according to the manufacturer's instructions, or methods commonly used in the art or described herein. The aforementioned techniques and methods are generally used as described in various comprehensive and specific documents that are well known in the art and that are cited and discussed in this specification. See, e.g., Sambrook et al., Molecular Cloning: A Laboratory Manual (2$^{nd}$ edition, Cold Spring Harbor Laboratory Press, Cold Spring Harbor, N. Y. (1989)).

As used herein, the term "polypeptide" is intended to encompass both the singular form "polypeptide" and the plural form "polypeptides", and refers to a molecule consisting of monomers (amino acids) linearly linked by amide bonds (also known as peptide bonds). The term "polypeptide" refers to any single chain or multiple chains of two or more amino acids and does not refer to a particular length of the product. Thus, included within the definition of "polypeptide" are peptides, dipeptides, tripeptides, oligopeptides, "proteins", "amino acid chains" or any other term used to refer to chains of two or more amino acids, and the term "polypeptide" may be used in place of, or interchangeably with, any of the above terms. The term "polypeptide" is also intended to refer to a product of post-expression polypeptide modification, including but not limited o glycosylation, acetylation, phosphorylation, amidation, derivatization by known protecting/blocking groups, proteolytic cleavage or non-naturally occurring amino acid modification. The polypeptide may be derived from a natural biological source or produced by recombinant techniques, but it is not necessarily translated from a specified nucleic acid sequence. It may be produced in any manner, including chemical synthesis, etc.

The "amino acid" refers to a compound containing both amino and carboxyl functional groups, such as α-amino acids. Two or more amino acids may form a polypeptide through amide bonds (also known as peptide bonds). A single amino acid is encoded by a nucleic acid consisting of three nucleotides (so-called codon or base triplet). Each amino acid is encoded by at least one codon. An amino acid may be encoded by different codons, which is known as "codon degeneracy". Amino acids include natural amino acids and non-natural amino acids. Natural amino acids include alanine (three-letter symbol: Ala, one-letter symbol: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y) and valine (Val, V).

The term "isolated" as used herein with respect to cells, nucleic acids, polypeptides, antibodies and the like, e.g., "isolated" DNA or RNA, refers to molecules that are separated from other components, such as natural DNA or RNA, respectively. The term "isolated" as used herein also refers to nucleic acids or polypeptides that are substantially free of cellular materials, viral materials or cell culture media when produced by recombinant DNA techniques, or of chemical precursors or other chemicals when chemically synthesized. In addition, "isolated nucleic acid" is intended to include nucleic acid fragments that do not occur in nature. The term "isolated" is also used herein to refer to cells or polypeptides that are separated from other cellular proteins or tissues. Isolated polypeptides are intended to include both purified and recombinant polypeptides. Isolated polypeptides, antibodies and the like are usually prepared by at least one purification step. In some embodiments, isolated nucleic acids, polypeptides, antibodies and the like are at least 50%, 60%, 70%, 80%, 90% or 95% pure.

In the present invention, the term "recombinant", with regard to a polypeptide or polynucleotide, is intended to refer to a polypeptide or polynucleotide that does not occur in nature, and it means that a polynucleotide or polypeptide that does not normally occur can be produced by combination.

"Homology" or "identity" or "similarity" refers to sequence similarity between two polypeptides or between two nucleic acid molecules. Homology is determined by comparing the positions that can be aligned in the sequences. When a position of the compared sequences is occupied by the same base or amino acid, then the molecules are homologous at that position. The degree of homology between the sequences is a function of the number of matching or homologous positions shared by the sequences.

A polynucleotide or polynucleotide region (or a polypeptide or polypeptide region) having a certain percentage (e.g., 60%, 65%, 70%, 75%, 80%, 85%, 90%, 95%, 98% or 99%) "sequence identity" or "sequence homology" to another sequence means that the percentage of bases (or amino acids) are identical between the two sequences compared when the sequences are aligned. The alignment and the percentage homology or sequence identity can be determined using software programs known in the art, such as the software programs described in Ausubel et al. eds., (2007) Current Protocols in Molecular Biology. In some embodiments, the alignment is performed using default parameters. One alignment program is BLAST using default parameters. Biologically equivalent polynucleotides are polynucleotides having the above specified percentage homology and encoding polypeptides having identical or similar biological activity.

The terms "polynucleotide" and "oligonucleotide" are used interchangeably and refer to a polymeric form of nucleotides of any length, whether deoxyribonucleotides or ribonucleotides or analogs thereof. The polynucleotide may have any three-dimensional structure and may perform any function, known or unknown. Examples of polynucleotides include: genes or gene fragments (such as probes, primers, EST or SAGE tags), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence and isolated RNA of any sequence. Polynucleotides can include modified nucleotides, such as methylated nucleotides and nucleotide analogs. Structural modifications to the nucleotides can be made before or after assembly of the polynucleotide. The sequence of nucleotides can be interrupted by non-nucleotide components. The polynucleotide may be further modified after polymerization. This term also refers to double-stranded and single-stranded molecules. Unless otherwise stated or required, any polynucleotide disclosed herein includes a double-stranded form and each of the two complementary single-stranded forms known or predicted to constitute the double-stranded form.

The term "encoding" as applied to a polynucleotide refers to a polynucleotide that can "encode" a polypeptide. If in its natural state or manipulated by methods well known to those skilled in the art, the polynucleotide can be transcribed and/or translated to produce the mRNA for a polypeptide and/or a fragment thereof. An antisense strand is a complement sequence of such a nucleic acid. The encoding sequence of the antisense strand can be deduced from the nucleic acid.

In the present invention, "antibody" or "antigen-binding fragment" refers to a polypeptide or polypeptide complex that specifically recognizes and binds to an antigen. The antibody may be an intact antibody or any antigen-binding fragment thereof or a single chain thereof. The term "antibody" thus includes proteins or peptides comprising a portion or the whole of an immunoglobulin molecule that has biological activity for binding to an antigen. The antibody includes, but is not limited to, complementarity determining regions (CDRs), heavy chain variable regions (VHs), light chain variable regions (VLs), heavy chain constant regions (CHs), light chain constant regions (CLs), framework regions (FRs) or any portion thereof of a heavy chain or a light chain or a ligand binding portion thereof. The CDRs include CDRs of the light chain (VL CDRs) and CDRs of the heavy chain (VH CDRs). Classes of the heavy chain of the antibody include γ, μ, α, δ, ε and some subclasses (e.g., γ1-γ4). The nature of this chain determines the "type" of the antibody as IgG, IgM, IgA, IgD or IgE. Some of these can be further divided into immunoglobulin subclasses (isotypes), such as IgG1, IgG2, IgG3, IgG4 and the like. Classes of the light chain include κ and λ. Each heavy chain may be connected with a k or A light chain. In general, when an immunoglobulin is produced by a hybridoma, a B cell or a genetically engineered host cell, the light and heavy chains are bound by covalent bonds, and the "tail" portions of the two heavy chains are bound by covalent disulfide bonds or non-covalent bonds. In the heavy chains, the amino acid sequence extends from the N terminus at the forked end of the Y configuration to the C terminus at the bottom of each chain. The immunoglobulin K light chain variable region is Vκ; the immunoglobulin A light chain variable region is VA. The VL commonly used in the present invention is Vκ. Although some discussions are directed to the IgG class of immunoglobulin molecules, all classes of immunoglobulins are within the protection scope disclosed herein. With respect to IgG, a standard immunoglobulin molecule comprises two identical light chain polypeptides having a molecular weight of about 23,000 Daltons and two identical heavy chain polypeptides having a molecular weight of about 53,000-70,000 Daltons. Both the light and heavy chains can be divided into structurally and functionally homologous regions. The terms "constant" and "variable" are used in accordance with function. In this regard, it should be understood that the VL and VH determine the antigen recognition and specificity. Antigen-binding sites on the VL and VH can recognize antigenic determinants and specifically bind to antigens. The antigen-binding sites are defined by three CDRs in each of the VH and VL (i.e., VH CDR1, VH CDR2, VH CDR3, VL CDR1, VL CDR2 and VL CDR3). The CL and CH (CH1, CH2 or CH3) impart important biological properties such as secretion, transplacental movement, Fc receptor binding, complement binding and the like. By convention, the numbering of amino acids in the constant regions increases as they become further away from the antigen-binding site of the antibody or amino terminus. The N-terminal portion is the variable region, and the C-terminal portion is the constant region; the CH3 and CL domains actually comprise the carboxyl termini of the heavy chain and light chain, respectively.

In the present invention, the heavy chain constant region of the antibody may be derived from different immunoglobulin molecules. For example, the heavy chain constant region of the antibody may include a CH1 domain derived from an IgG1 molecule and a hinge region derived from an IgG3 molecule. In another embodiment, the heavy chain constant region may include a hinge region derived partially from an IgG1 molecule and partially from an IgG3 molecule. In another embodiment, a portion of the heavy chain may include a chimeric hinge region derived partially from an IgG1 molecule and partially from an IgG4 molecule.

In the present invention, the term "hinge region" includes a portion of the heavy chain structure connecting the CH1 domain and CH2 domain. The hinge region comprises about 25 residues and is flexible, thereby enabling independent movement of the two N-terminal antigen-binding regions.

As used herein, the term "disulfide bond" includes a covalent bond formed between two sulfur atoms. Cysteine comprises a thiol group which can form a disulfide bond or bridge with a second thiol group. In most naturally occurring IgG molecules, the CH1 and CL regions are linked by a disulfide bond, and the two heavy chains are linked by two disulfide bonds.

In the present invention, the term "fragment", "antibody fragment" or "antigen-binding fragment" is a portion of an antibody, such as F(ab') 2, F (ab) 2, Fab', Fab, Fv, scFv, etc. Regardless of its structure, the antibody fragment binds to the same antigen recognized by an intact antibody. The term "antigen-binding fragment" includes aptamers, mirror image isomers and bivalent antibodies, and also includes any synthetic or genetically engineered protein that functions as an antibody by binding to a particular antigen to form a complex.

The "scFv" refers to a fusion protein of a VH and a VL of an immunoglobulin. In some aspects, these regions are linked to a short linker peptide having about 10 to about 25 amino acids. The linker may be enriched with glycine to improve flexibility, and enriched with serine or threonine to improve solubility, and may link the N terminus of VH and the C terminus of VL, or vice versa. Although the protein has the constant region removed and the linker introduced, it retains the specificity of the original immunoglobulin.

Antibodies, antigen-binding fragments, variants or derivatives disclosed herein include, but are not limited to, polyclonal, monoclonal, multispecific, fully human, humanized, primatized or chimeric antibodies, single-chain antibodies and epitope-binding fragments.

The term "epitope" as used herein includes any protein determining region that can specifically bind to an immunoglobulin or a fragment thereof or a T cell receptor. The epitope determinant generally consists of chemically active surface groups of molecules (such as amino acids or sugar side chains), and usually has specific three-dimensional structural properties and specific charge properties. When the dissociation constant is less than or equal to 1 μM (e.g., less than or equal to 100 nM, less than or equal to 10 nM, or less than or equal to 1 nM), it can be said that an antibody specifically binds to an antigen.

Where the terms used and/or accepted in the art have two or more definitions, the definitions of the terms used herein include all of these meanings unless explicitly indicated as opposite.

Unless otherwise stated, the numbering of residues in various domains of antibodies is based on the EU numbering scheme, which is also known as EU index as described in Kabat et al., *Sequences of Proteins of Immunological Interest,* $5^{th}$ Ed., Public Health Service, National Institutes of Health, Bethesda, MD, 1991.

The antibodies disclosed herein may be derived from any animal, including birds and mammals. Preferably, the antibodies are human, murine, donkey, rabbit, goat, guinea pig, camel, llama, horse or chicken antibodies. In another embodiment, the variable region may be derived from a chondrichthyes source (e.g., from a shark).

In the present invention, the term "chimeric antibody" is considered to be any antibody in which the variable region of the antibody is obtained or derived from a first species, and the constant region thereof (which may be intact, partial or modified in the present invention) is derived from a second species. In some embodiments, the variable region is derived from a non-human source (e.g., mouse or primate) and the constant region is derived from a human source.

"Specifically bind to" or "specific for" generally refers to that an antibody binds to an epitope through its antigen-binding domain, and that the binding requires complementarity between the antigen-binding domain and the epitope. By this definition, an antibody is said to "specifically bind to" an epitope when it binds to the epitope more readily through its antigen-binding domain than it binds to a random, irrelevant epitope. The term "specificity" is used herein to define the relative affinity of a specific antibody for binding to a specific epitope. The strength or affinity of an immunological binding interaction can be expressed as an equilibrium dissociation constant ($K_D$) of the interaction, where a smaller $K_D$ indicates a stronger affinity. The immunological binding properties of the selected polypeptides may be quantified using methods well known in the art. One such method requires the measurement of the rates of antigen-binding site/antigen complex formation and dissociation, where those rates depend on the concentration of the complex partners, the affinity of the interaction and geometric parameters that affect the rates equally in both directions. Thus, both "association rate constant" ($K_{on}$) and "dissociation rate constant" ($K_{off}$) can be determined by calculating the concentration and the actual association and dissociation rates (see *Nature* 361:186-87 (1993)). The ratio $K_{off}/K_{on}$ can eliminate parameters that are independent of the affinity and is equal to the equilibrium dissociation constant $K_D$, i.e., the affinity value (generally see Davies et al. (1990) *Annual Rev Biochem* 59:439-473). Antibodies disclosed herein can be considered to specifically bind to OX40 when the equilibrium binding constant ($K_D$) to OX40 is ≤1 μM.

In the present invention, the "content" of fucose in an antibody refers to a molar ratio of glycoform moieties comprising fucose to all glycoform moieties in the antibody. In some embodiments, the content of fucose in an antibody is not less than about 90%, about 91%, about 92%, about 93%, about 94%, about 95%, about 96%, about 97%, about 98% or about 99%. In some embodiments, the content of fucose in an antibody is about 96%. In some embodiments, the content of fucose in an antibody is no more than about 10%, about 9%, about 8%, about 7%, about 6%, about 5%, about 4%, about 3%, about 2%, about 1% or about 0.5%. In some embodiments, the content of fucose in an antibody is about 0.

In the present invention, the term "treatment" refers to prophylactic measures and/or therapeutic treatments, the purpose of which is to prevent, slow down and/or eliminate the progression of an undesirable physiological change or disorder (such as a cancer). Beneficial or desired clinical results include, but are not limited to, for example, the alleviation of symptoms, the reduction in the severity of a disease, the stabilization (i.e., no worsening) of a disease state, the delay or slowing of disease progression, the amelioration or alleviation of a disease state and the like. "Treatment" also means an extended survival (compared to the expected survival for those without treatment). Those in need of the treatment include those with the condition or disorder, as well as those susceptible to the condition or disorder, or those in whom the condition or disorder is to be prevented.

"Patient" generally refers to any patient, particularly a mammalian patient, in need of diagnosis, prognosis or treatment. Mammalian patients include humans, dogs, cats, guinea pigs, rabbits, rats, mice, horses, bovines, cows, etc., particularly humans.

In the present invention, for example, "a patient in need of treatment" includes patients, e.g., mammalian patients, that benefit from administration of the antibodies or compositions disclosed herein for detection, diagnostic procedures, prevention and/or treatment.

Unless otherwise stated, the term "OX40" refers to any natural OX40 derived from any vertebrate (including mammals, such as primates (e.g., humans and rhesus monkeys), and rodents (e.g., mice and rats)). The term encompasses "full-length", unprocessed OX40, and OX40 in any form resulting from intracellular processing.

"OX40 activation" refers to the activation of OX40 receptors. Generally, OX40 activation results in signal transduction.

"Activating T cells" means inducing, causing or stimulating effector or memory T cells to have renewed, sustained or amplified biological function. Examples of enhancing T cell functions include: increased secretion of γ-interferon (e.g., IFNg) or interleukin (e.g., IL-2) from a CD8+ effector T cell, increased secretion of γ-interferon (e.g., IFNg) or interleukin (e.g., IL-2) from a CD4+ memory and/or effector T cell, enhanced proliferation of a CD4+ effector and/or memory T cell, enhanced proliferation of a CD8+ effector T cell and enhanced antigen responsiveness (e.g., clearance) relative to such levels before the intervention. The relevant measurement methods are known to those skilled in the art.

The term "cytokine" is a generic term for proteins that are released by a cell population and act as intercellular mediators on another cell. Examples of such cytokines are lymphokines, monokines, interleukins (ILs) (such as IL-1, IL-1α, IL-2, IL-3, IL-4, IL-5, IL-6, IL-7, IL-8, IL-9, IL-11, IL-12, IL-15), tumor necrosis factors (such as TNF-α or TNF-β) and other polypeptide factors (including LIF and kit ligand (KL) and γ-interferon). As used herein, the term "cytokine" includes proteins from natural sources or from recombinant cell cultures and biologically active equivalents of natural sequence cytokines. The biologically active equivalents include small molecule entities produced by artificial synthesis, and pharmaceutically acceptable derivatives and salts thereof.

As used herein, the term "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain instances, the label or labels may also be therapeutic. Various methods for labeling polypeptides and glycoproteins are known in the art and can be used. Examples of labels for polypeptides include, but are not limited to: radioisotopes or radionuclides (e.g., $^{3}H$, $^{14}C$, $^{15}N$, $^{35}S$, $^{90}Y$, $^{99}Tc$, $^{111}In$, $^{125}I$ and $^{131}I$), fluorescent labels (e.g., FITC, rhodamine and lanthanide phosphor), enzymatic labels (e.g., horseradish peroxidase, β-galactosidase, luciferase and alkaline phosphatase), chemiluminescent labels, biotinyl groups and predetermined polypeptide epitopes recognized by secondary reporter genes (e.g., leucine zipper pair sequences, secondary antibody-binding sites, metal binding domains and epitope tags). In some embodiments, the labels are connected by spacer arms of various lengths to reduce potential steric hindrance.

Anti-OX40 Antibody

Antibodies of the present invention have the ability to bind to OX40 and can activate intracellular signaling pathways of OX40, particularly in the presence of Fc receptors or cells expressing Fc receptors, thereby promoting the activation of T cells and inhibiting tumor growth or metastasis. For example, the function in activating T cells may be detected by using the NFκB reporter gene system described in the examples herein.

In some embodiments, the present invention provides an antibody or an antigen-binding fragment thereof that binds to human OX40 or rhesus monkey OX40. In some embodiments, the anti-OX40 antibody or the antigen-binding fragment thereof of the present invention retains strong binding to human OX40 or rhesus monkey OX40 (e.g., comparable to or stronger than known anti-OX40 antibodies, such as OX40mAb24 and 11D4).

In some embodiments, the antibody or the antigen-binding fragment thereof of the present invention binds to human OX40 or rhesus monkey OX40. The antibody or the antigen-binding fragment thereof of the present invention does not bind to or has lower (compared to human OX40 or rhesus monkey OX40) binding to murine OX40, such as mouse OX40.

In some embodiments, the anti-OX40 antibody or the antigen-binding fragment thereof of the present invention binds to human OX40 with a $K_D$ of less than or equal to about 20 nM, about 19 nM, about 12 nM, about 6 nM, about 5 nM, about 4 nM or about 2 nM. In some embodiments, the $K_D$ is less than or equal to about 1 nM, about 0.8 nM, about 0.6 nM, about 0.4 nM or about 0.2 nM. In some embodiments, the $K_D$ is about 0.16 nM. In some embodiments, the antibody binding affinity is determined using biological optical interferometry (e.g., Fortebio affinity assay).

In some embodiments, the binding of the antibody or the antigen-binding fragment thereof of the present invention to human OX40 is determined using a flow cytometry assay. In some embodiments, the EC50 for binding to human OX40 is less than or equal to about 1.5 nM. In some embodiments, the EC50 for binding to human OX40 is less than or equal to about 1.33 nM or about 1.0 nM.

In some embodiments, the agonist activity of the anti-OX40 antibody is assessed by OX40 signaling, and determined mainly by Jurkat cells transfected with OX40 and NFκB reporter genes. The present invention provides an anti-OX40 antibody or an antigen-binding fragment thereof that increases the level of NFκB-mediated transcriptional activity compared to an IgG control antibody. In some embodiments, the anti-OX40 antibody or the antigen-binding fragment thereof can increase the level of NFκB-mediated transcriptional activity by about 9-fold or more in the presence of Raji cells, compared to a corresponding control IgG. In some embodiments, the anti-OX40 antibody or the fragment thereof can increase the level of NFκB-mediated transcriptional activity by about 5-fold or more compared to a corresponding control IgG.

In some embodiments, an Fc of the anti-OX40 antibody is mutated with RY (E345R and S440Y) and R (E345R), and its activity is determined using Jurkat cells transfected with OX40 and NFκB reporter genes. The activity of the antibody with RY mutation is 12-fold higher than that of the antibody without mutation, and the activity of the antibody with R mutation is 10-fold higher than that of the antibody without mutation.

In some embodiments, the agonist activity of the anti-OX40 antibody is assessed by the level of cytokines (IL-2) released from PBMC cells after activation. The anti-OX40 antibody or the fragment thereof of the present invention can increase the level of IL-2 secreted by PBMC cells by up to about 1-fold, about 2-fold, about 3-fold or more compared to a corresponding control IgG.

In some embodiments, the affinity of the anti-OX40 antibody or the antigen-binding fragment thereof is increased by about 5-fold, about 10-fold, about 20-fold or about 70-fold after affinity maturation.

In some embodiments, the anti-OX40 antibody or the antigen-binding fragment thereof of the present invention comprises a heavy chain variable region (VH), wherein the VH comprises complementarity determining regions VH CDR1, VH CDR2 and VH CDR3, wherein the VH CDR1 comprises or consists of an amino acid sequence having at least 90%, 91%, 92%, 93%, 94%, 95%, 96%, 97%, 98% or 99% identity or 100% identity to an amino acid sequence selected from SEQ ID NOs: 1, 4, 10, 16, 104 and 22; the VH CDR2 comprises or consists of an amino acid sequence having at least 90%, 91%, 92%, 93%, 94%, 95%, 96%, 97%, 98% or 99% identity or 100% identity to an amino acid sequence selected from SEQ ID NOs: 2, 5, 7, 8, 11, 13, 14, 17, 20, 23 and 26; and the VH CDR3 comprises or consists of an amino acid sequence having at least 90%, 91%, 92%, 93%, 94%, 95%, 96%, 97%, 98% or 99% identity or 100% identity to an amino acid sequence selected from SEQ ID NOs: 3, 6, 9, 12, 15, 18, 21, 24 and 27.

In some embodiments, the anti-OX40 antibody or the antigen-binding fragment thereof of the present invention comprises a light chain variable region (VL), wherein the VL comprises complementarity determining regions (CDRs) VL CDR1, VL CDR2 and VL CDR3, wherein the VL CDR1 comprises or consists of an amino acid sequence having at least 90%, 91%, 92%, 93%, 94%, 95%, 96%, 97%, 98% or 99% identity or 100% identity to an amino acid sequence selected from SEQ ID NOs: 28, 31, 37, 40, 43, 46, 49, 52, 55, 58 and 61; the VL CDR2 comprises or consists of an amino acid sequence having at least 90%, 91%, 92%, 93%, 94%, 95%, 96%, 97%, 98% or 99% identity or 100% identity to an amino acid sequence selected from SEQ ID NOs: 19, 25, 29, 32, 35, 38, 44, 47, 50, 56, 59 and 62; and the VL CDR3 comprises or consists of an amino acid sequence having at least 90%, 91%, 92%, 93%, 94%, 95%, 96%, 97%, 98% or 99% identity or 100% identity to an amino acid sequence selected from SEQ ID NOs: 30, 33, 34, 36, 39, 41, 42, 45, 48, 51, 53, 54, 57, 60 and 63. The VH CDR1, VH CDR2, VH CDR3, VL CDR1, VL CDR2 and VL CDR3 in the antibody or the antigen-binding fragment thereof of the present invention can be any exemplary combination of amino acid sequences corresponding to the CDRs in Table 1.

TABLE 1

CDR sequence corresponding to each sequence number

| SEQ ID NO | VH CDR1 | SEQ ID NO | VH CDR2 | SEQ ID NO | VH CDR3 |
|---|---|---|---|---|---|
| 1 | GETESSYA | 2 | ISYDG SNK | 3 | ARELGVYS GYDTPFDY |
| 4 | GFTFDDYA | 3 | IGGSGGST | 6 | AKDRGYGD YYWYFDL |
| 10 | SYGMH | 7 | VISEDG SNQYYAD SVKG | 9 | AKDPLGS SWFEYFQH |

TABLE 1-continued

| CDR sequence corresponding to each sequence number | | | | | |
|---|---|---|---|---|---|
| 16 | GFTFSTYA | 8 | ISGSGGNT | 12 | DNQDSSPDVGIDY |
| 22 | GFTVSSNY | 11 | VISYDGSNQYYADSVKG | 15 | AKDGPYFDY |
| 104 | GFTFSSYG | 13 | VIAEVGSNQYYADSVKG | 18 | AKSSSTVATDFDYGMDV |
| | | 14 | ISNSGGST | 21 | ARGDSSSWFIFQD |
| | | 17 | ISGTGDWA | 24 | ARVVVPGYFDL |
| | | 20 | ISGSGGST | 27 | DNQDTSPDVGIDY |
| | | 23 | IYYGGST | | |
| | | 26 | VIWEDGSNQYYADSVKG | | |
| SEQ ID NO | VL CDR1 | SEQ ID NO | VL CDR2 | SEQ ID NO | VL CDR3 |
| 28 | RDIRDD | 19 | AAVALQS | 30 | LQDSDYPLT |
| 31 | SSDVGGYNY | 25 | AAVGLQS | 33 | SSYTTSSTLV |
| 37 | QDILGY | 29 | AAS | 34 | QQYTDYPLT |
| 40 | QSISSYLN | 32 | DVS | 36 | SSYSSSSTLVV |
| 43 | RASQNISPILN | 35 | EVS | 39 | QQYNSYPLT |
| 46 | QGIGDD | 38 | ATS | 41 | QQYDDYPLT |
| 49 | EEIGSWLAW | 44 | AASSLQS | 42 | LQIDSYPLT |
| 52 | EDIGRW | 47 | KAS | 45 | QQYNDYPLT |
| 55 | SSNMGSNP | 50 | EAS | 48 | QQAHSFPPT |
| 58 | DSLRSYYAS | 56 | NNN | 51 | QQYGSYPPT |
| 61 | RASQNISPFLN | 59 | NNR | 53 | QQYSDYPLT |
| | | 62 | AAVGSQS | 54 | QQYYNYPPT |
| | | 60 | HSRDSSGKYV | 57 | AAWDDGLNGWV |
| | | 63 | QQYTDYPL | | |

In some embodiments, the anti-OX40 antibody or the fragment thereof of the present invention comprises a heavy chain variable region VH comprising or consisting of an amino acid sequence having at least 90%, 91%, 92%, 93%, 94%, 95%, 96%, 97%, 98% or 99% identity or 100% identity to an amino acid sequence selected from SEQ ID NOs: 64-72.

In some embodiments, the anti-OX40 antibody or the antigen-binding fragment thereof of the present invention comprises a light chain variable region VL comprising or consisting of an amino acid sequence having at least 90%, 91%, 92%, 93%, 94%, 95%, 96%, 97%, 98% or 99% identity or 100% identity to an amino acid sequence selected from SEQ ID NOs: 73-84.

In some embodiments, the heavy chain variable region VH and the light chain variable region VL in the antibody or the antigen-binding fragment thereof of the present invention are exemplary combinations in Table 3.

In some embodiments, the antibody or the fragment thereof further comprises a heavy chain constant region, a light chain constant region, an Fc region, or a combination thereof.

In some embodiments, the antibody comprises a heavy chain set forth in SEQ ID NO: 86 and a light chain set forth in SEQ ID NO: 87.

An antibody, an antigen-binding fragment, a variant or a derivative is disclosed herein. The variant refers to an antibody or an antigen-binding fragment thereof obtained by deletion and/or substitution of one or more amino acid residues or insertion of one or more amino acid residues in an antibody or an antigen-binding fragment thereof. The derivative includes modified derivatives, i.e., modified by covalent binding of any type of molecules to antibodies, wherein the covalent binding does not prevent antibodies from binding to epitopes. For example, but not by way of limitation, an antibody may be modified by glycosylation, acetylation, pegylation, phosphorylation, amidation, derivatization by known protecting/blocking groups, proteolytic cleavage, attachment to cellular ligands or other proteins, or the like. Any of a number of chemical modifications may be made by techniques in the prior art, including but not limited to specific chemical cleavage, acetylation, formylation, metabolic synthesis of tunicamycin, and the like. In addition, the antibody may comprise one or more unnatural amino acids.

In some embodiments, the antibody may be conjugated to a therapeutic agent, a prodrug, a peptide, a protein, an enzyme, a virus, a lipid, a biological response modifier, an agent, or PEG.

The antibody may be conjugated or fused to a therapeutic agent, which may include a detectable label (such as a radiolabel), an immunomodulator, a hormone, an enzyme, an oligonucleotide, a photoactive therapeutic or diagnostic agent, a cytotoxic agent which may be a drug or a toxin, an ultrasound enhancing agent, a nonradioactive label, a composition thereof, and other such agents known in the art.

The antibody may be detectably labeled by coupling to a chemiluminescent compound. The presence of the chemiluminescent-labeled antigen-binding fragment is then determined by detecting the luminescence that occurs during the chemical reaction. Examples of particularly useful chemiluminescent-labeled compounds include luminol, isoluminol, aromatic acridinium esters, imidazole, acridinium salts and oxalate esters.

In some embodiments, the heavy chain and/or light chain of the anti-OX40 antibody or the fragment thereof of the present invention further comprise a signal peptide sequence, such as MEFGLSWVFLVAILKGVQC (SEQ ID NO: 85).

In some embodiments, the antibody of the present invention further encompasses a variant of the amino acid sequence of the anti-OX40 antibody, and an antibody that binds to the same epitope as any of the antibodies described above.

In some embodiments, the anti-OX40 antibody of the present invention further encompasses an antibody fragment thereof; in some embodiments, the antibody fragment is selected from the following fragments: Fab, Fab'-SH, Fv, scFv and (Fab')2.

The anti-OX40 antibody of the present invention can be prepared by conventional recombinant DNA techniques, e.g., by using recombinant DNA techniques well known to those skilled in the art to select, construct and culture DNA encoding the antibody, and vectors and cell lines producing the antibody. These techniques are described in various laboratory manuals and main publications. In this aspect, for the techniques suitable for use in the present invention described below, reference is made to *Current Protocols in Immunology*, Coligan et al., Eds., Green Publishing Associates and Wiley-Interscience, John Wiley and Sons, New York (1991), which is incorporated herein by reference in its entirety, including the supplements.

In some embodiments, the DNA encoding the antibody can be designed and synthesized according to the antibody amino acid sequence described herein by conventional methods, inserted into an expression vector, and transfected into a host cell. The transfected host cell is then cultured in a medium to produce the monoclonal antibody. In some embodiments, the vector expressing the antibody comprises at least one promoter element, an antibody coding sequence, a transcription termination signal and a poly-A tail. Other elements include enhancers, Kozak sequences, and donor and acceptor sites inserted into two ends of the sequence for RNA splicing. Efficient transcription can be obtained by early and late promoters of SV40, long terminal repeats from retroviruses such as RSV, HTLV1 and HIVI, and early promoters of cytomegalovirus, and promoters from other cells such as actin promoter can also be used. Suitable expression vectors may include pIRES1neo, pRetro-Off, pRetro-On, PLXSN, or Plncx, pcDNA3.1 (+/−), pcDNA/Zeo (+/−), pcDNA3.1/Hygro (+/−), PSVL, PMSG, pRSV-cat, pSV2dhfr, pBC12MI, pCS2, etc. Commonly used mammalian cells include 293 cells, Cos1 cells, Cos7 cells, CVI cells, murine L cells, CHO cells and the like.

In some embodiments, the inserted gene fragment should comprise a screening label, common ones of which include screening genes such as dihydrofolate reductase, glutamine synthetase, neomycin resistance and hygromycin resistance, to facilitate the screening and separation of cells that have been successfully transfected. The constructed plasmid is transfected into a host cell, and the successfully transfected cells are cultured in a large quantity in a selective culture medium to produce the desired target protein.

In some embodiments, the present invention provides a nucleic acid encoding any of the above anti-OX40 antibodies or fragments thereof. In one embodiment, a vector comprising the nucleic acid is provided. In one embodiment, the vector is an expression vector, including plasmids, retroviruses, YAC, EBV-derived episomes and the like. In one embodiment, a host cell comprising the vector is provided. In one embodiment, the host cell is eukaryotic. In another embodiment, the host cell is selected from a yeast cell, a mammalian cell (e.g., CHO cell or 293F cell), and other cells suitable for preparing an antibody or an antigen-binding fragment thereof.

In some embodiments, the polynucleotide comprises one or more nucleotide sequences set forth in SEQ ID NOs: 96-101. In some embodiments, the polynucleotide comprises nucleotide sequences set forth in SEQ ID NOs: 96, 97 and 98. In some embodiments, the polynucleotide comprises nucleotide sequences set forth in SEQ ID NOs: 99, 100 and 101. In some embodiments, the polynucleotide comprises a nucleotide sequence set forth in SEQ ID NO: 102. In some embodiments, the polynucleotide comprises a nucleotide sequence set forth in SEQ ID NO: 103. In some embodiments, the polynucleotide comprises a nucleotide sequence set forth in SEQ ID NO: 102 and/or a nucleotide sequence set forth in SEQ ID NO: 103. In some embodiments, a polynucleotide comprising a nucleotide sequence set forth in SEQ ID NO: 96, 97, 98, 99, 100 or 101 can encode a polypeptide comprising an amino acid sequence set forth in SEQ ID NO: 10, 26, 27, 61, 62 or 63, respectively. In some embodiments, a polynucleotide comprising a nucleotide sequence set forth in SEQ ID NO: 102 can encode a polypeptide comprising an amino acid sequence set forth in SEQ ID NO: 72; in some embodiments, a polynucleotide comprising a nucleotide sequence set forth in SEQ ID NO: 103 can encode a polypeptide comprising an amino acid sequence set forth in SEQ ID NO: 84. In some embodiments, a polynucleotide comprising a nucleotide sequence set forth in SEQ ID NO: 105 can encode a polypeptide comprising an amino acid sequence set forth in SEQ ID NO: 90; in some embodiments, a polynucleotide comprising a nucleotide sequence set forth in SEQ ID NO: 106 can encode a polypeptide comprising an amino acid sequence set forth in SEQ ID NO: 91. Nucleotide sequences are shown in Table 2 below.

TABLE 2

Sequence listing of each numbered nucleotide

| SED ID NO: | Sequence |
|---|---|
| 96 | tcctacggcatgcac |
| 97 | gtgatctgggaggatggctccaaccagtactatgc<br>cgacagcgtgaaggga |
| 98 | gacaaccaagacaccagccccgacgtgggcatcga<br>ttat |
| 99 | agagccagccagaacatctcccccttttctgaat |
| 100 | gccgctgtgggactgcagagc |
| 101 | cagcagtataccgactaccctctgacc |
| 102 | caagtgcagctggtggagagcggaggaggagtggt<br>gcaacccggcgagtccctcagactgagctgtgccg<br>ccagcggcttcaccttcagctcctacggcatgcac<br>tgggtgagacaagcccccggcaaaggactggagtg<br>ggtggccgtgatctgggaggatggctccaaccagt<br>actatgccgacagcgtgaagggaagattcaccatc<br>tctagagacaactccaagaacacactgtatctgca<br>gatgaactctctgagggccgaggacaccgccgtgt<br>actactgcgccaaggacaaccaagacaccagcccc<br>gacgtgggcatcgattattggggccagggtaccct<br>ggttaccgttagcagc |
| 103 | gacatccagatgacccagagccctagctctctgtc<br>cgctagcgtgggagatagagtgaccatcacatgca<br>gagccagccagaacatctcccccttttctgaattgg<br>tatcagcagaagcccggcaaggcccctaagctgct<br>gatctatgccgctgtgggactgcagagcggagtgc<br>cttccagattctccggcagcggcagcggaaccgac<br>ttcacactgaccatcagctctctgcagcccgagga<br>cttcgccacctactactgccagcagtataccgact<br>accctctgaccttcggaggcggcaccaaggtggag<br>atcaag |
| 105 | gcgagcaccaaaggcccgagcgtgtttccgctggc<br>cccgagcagcaaaagcaccagcggtggcaccgcag<br>cgctgggttgcctggtgaaagattatttcccggaa<br>ccggtgacggtgtcgtggaactcaggcgccctgac<br>cagcggcgtgcacaccttcccggctgtcctacagt |

TABLE 2-continued

Sequence listing of each numbered nucleotide

| SED ID NO: | Sequence |
|---|---|
| | cctcaggactctactccctcagcagcgtggtgacc<br>gtgccctccagcagcttgggcacccagacctacat<br>ctgcaacgtgaatcacaagcccagcaacaccaagg<br>tggacaagaaagttgagcccaaatcttgtgacaaa<br>actcacacatgcccacegtgeceageacctgaact<br>cetggggggaccgtcagtcttcctcttccccccaa<br>aacccaaggacaccctcatgatctcccggacccct<br>gaggtcacatgcgtggtggtggacgtgagccacga<br>agaccctgaggtcaagttcaactggtacgtggacg<br>gcgtggaggtgcataatgccaagacaaagccgcgg<br>gaggagcagtacaacagcacgtaccgtgtggtcag<br>cgtcctcaccgtcctgcaccaggactggctgaatg<br>gcaaggagtacaagtgcaaggtctccaacaaagcc<br>ctcccagcccccatcgagaaaaccatctccaaagc<br>caaagggcagccccgagaaccacaggtgtacaccc<br>tgcccccatcecgggatgagctgaccaagaaccag<br>gtcagcetgacctgcctggtcaaaggettetatcc<br>cagcgacatcgccgtggagtgggagagcaatgggc<br>agccggagaacaactacaagaccacgcctcccgtg<br>ctggactccgacggctccttcttcctctacagcaa<br>gctcaccgtggacaagagcaggtggcagcagggga<br>acgtcttctcatgctccgtgatgcatgaggctctg<br>cacaaccactacacgcagaagagcctctccctgtc<br>tccgggtaaa |
| 106 | cgtacggtggctgeaccatctgtcttcatcttccc<br>gccatctgatgageagttgaaatctggaactgcct<br>ctgttgtgtgcctgctgaataacttctatcccaga<br>gaggccaaagtacagtggaaggtggataacgccct<br>ccaatcgggtaactcccaggagagtgtcacagagc<br>aggacagcaaggacagcacctacagcctcagcagc<br>accctgacgctgagcaaagcagactacgagaaaca<br>caaagtctacgcctgcgaagtcacccatcagggcc<br>tgagctcgcccgtcacaaagagcttcaacagggga<br>gagtgt |

Pharmaceutical compositions of the present invention may comprise the antibody or the antigen-binding fragment thereof of the present invention. These pharmaceutical compositions may be contained in a kit, such as a diagnostic kit.

The present invention further provides a method for alleviating symptoms of cancer or other neoplastic diseases or infection by administering to a patient in need one or more antibodies or fragments described herein. The antibody should be administered at a dose sufficient to alleviate the symptoms of cancer or other neoplastic diseases or infection in the patient. In some embodiments, the patient is a human. In some embodiments, the antibody is chimeric, humanized or fully human. In some embodiments, the antibody or the fragment thereof can activate T cells and promote their proliferation or secretion of inflammatory factors. In some embodiments, the antibody or the fragment thereof is of an IgG isotype selected from the group consisting of IgG1 isotype, IgG2 isotype, IgG3 isotype and/or IgG4 isotype. In some embodiments, the antibody or the antigen-binding fragment thereof is of an IgG isotype selected from IgG4P and IgG4PE. In some embodiments, the antibody or the antigen-binding fragment thereof is of an IgG isotype selected from one comprising RY (E345R and S440Y) and R (E345R).

In some embodiments, the anti-OX40 antibody and other therapeutic agents are prepared as a single therapeutic composition, and the anti-OX40 antibody and the other therapeutic agents are administered simultaneously. Alternatively, the anti-OX40 antibody and the other therapeutic agents are independent of each other, for example, are each prepared as an independent therapeutic composition, and the anti-OX40 antibody and the other therapeutic agents are administered simultaneously, or the anti-OX40 antibody and the other therapeutic agents are administered at different time points during implementation of a therapeutic regimen. For example, the anti-OX40 antibody is administered before the other therapeutic agents, the anti-OX40 antibody is administered after the other therapeutic agents, or the anti-OX40 antibody and the other therapeutic agents are administered in an alternating scheme. In the present invention, the anti-OX40 antibody and the other therapeutic agents are administered at a single dose or at multiple doses.

It will be understood by those skilled in the art that the antibodies of the present invention can be widely used. For example, the antibodies of the present invention can be used as therapeutic agents, reagents in diagnostic kits or diagnostic tools, or reagents in competitive experiments to produce therapeutic agents.

The present invention provides antibodies and sequences thereof in Table 3. In the present invention, these antibodies are collectively referred to as anti-OX40 antibodies.

Some properties of the antibodies described herein include: specific binding to human OX40 and rhesus monkey OX40; ability in activating intracellular signaling pathways of OX40; ability in promoting T cell activation; and strong tumor suppressing activity.

The equilibrium dissociation constant ($K_D$) for the binding of the antibody and the fragment thereof of the present invention to the human OX40 epitope is determined using biological optical interferometry and BIACORE, and it is less than or equal to about 20 nM, about 19 nM, about 12 nM, about 6 nM, about 5 nM, about 4 nM or about 2 nM. In some embodiments, the $K_D$ is less than or equal to about 1 nM or 0.16 nM.

The equilibrium binding constant ($K_D$) for the binding of the antibody or the fragment thereof of the present invention to the human OX40 epitope is determined using a flow cytometry assay. In some embodiments, the EC50 for binding to human OX40 is less than or equal to about 1.5 nM. In some embodiments, the EC50 for binding to human OX40 is less than or equal to about 1.33 nM or 1.0 nM. The determined $K_D$ thereof is equal to or less than that of the known control antibody.

The activity of the anti-OX40 antibody of the present invention in activating OX40 is identified using the NFκB reporter gene system, and the EC50 is about 0.14 μg/mL in the presence of protein A and the EC50 is about 0.0602 μg/mL and 0.0722 μg/mL in the presence of Raji cells.

Exemplary antibodies of the present invention include antibody-F10, antibody-F15-1L, antibody-A2, antibody-X35-6L, antibody-A6-1k, antibody-M5-5k, antibody-M5-7k, antibody-F23-4k, antibody-F23-7k, antibody-F23-32k, antibody-FE-16H and antibody M. Exemplary antibodies of the present invention include an antibody comprising a variable heavy chain having a sequence selected from SEQ ID NOs: 64-72 and a variable light chain (VL) having a sequence selected from SEQ ID NOs: 73-84. In particular, exemplary antibodies include those provided in Table 3.

TABLE 3

| Sequence listing of each numbered anti-OX40 antibody | | | |
|---|---|---|---|
| No. | Name | Heavy chain variable region | Light chain variable region |
| 1 | Antibody-F10 | QVQLQESGGGLEKPGRSLRLSCAASGFT FSSYAMHWVRQAPGKGLEWVAVISYDG SNKYYADSVKGRFTISRDNSKNTLYLQM NSLRAEDTAVYYCARELGVYSGYDTPF DYWGQGTLVTVSS (SEQ ID NO: 64) | DIQMTQSPSSLSASVGDRITITCRASRDIR DDLAWYQQKPGGAPKLLIYAASTLQSG VPSRFSGSGSGTDFTLTISSLQPEDFATYY CLQDSDYPLTFGGGTKLEIK (SEQ ID NO: 73) |
| 2 | Antibody-X35-6L | EVQLVESGGGLVQPGRSLRLSCAASGFT FDDYAMHWVRQAPGRGLEWVSGIGGS GGSTYYADSVKGRFTISRDNSKNTLYLQ MNGLGAEDTAVYYCAKDRGYGDYYW YFDLWGRGTLVTVSS (SEQ ID NO: 65) | SSELTQPASVSGSPGQSITISCTGTSSDVG GYNYVSWYQQHPGKAPKLMIYDVSNR PSGVSNRFSGSKSGNTASLTISGLQAEDE ADYYCSSYTTSSTLVFGGGTKVTVL (SEQ ID NO: 74) |
| 3 | Antibody-F15-IL | QVQLRESGGGLVQPGGSLRLSCAASGFT FSSYAMNWVRQAPGKGLEWVSAISGSG GNTYYADSVKGRLTISRDNSKNTLYLQM NSLRAEDTAVYYCAKDPLGSSWFEYFQ HWGQGTLVTVSS (SEQ ID NO: 66) | QSALTQPASVSGSPGQSITISCTGTSSDV GGYNYVSWYQKHPGKAPKLMIYEVSN RPSGVSNRFSGSKSANTASLTISGLQAED EADYFCSSYSSSSTLVVFGGGTKLTVL (SEQ ID NO: 75) |
| 4 | Antibody-F23-4k | QVQLEESGGGVVQPGESLRLSCAASGFT FSSYGMHWVRQAPGKGLEWVAVISYDG SNQYYADSVKGRFTISRDNSKNTLYLQM NSLRAEDTAVYYCAKDNQDSSPDVGID YWGQGTLVTVSS (SEQ ID NO: 67) | DIWTQSPSSLSASVGDRVTITCRASQDI LGYVNWYQQKPGKAPILLIYATSGLQGG VPSRFSGSGSGTDFTLTISSLQPEDFATYY CQQYNSYPLTFGGGTKVDIK (SEQ ID NO: 76) |
| 5 | Antibody-F23-7k | QVQLEESGGGVVQPGESLRLSCAASGFT FSSYGMHWVRQAPGKGLEWVAVISYDG SNQYYADSVKGRFTISRDNSKNTLYLQM NSLRAEDTAVYYCAKDNQDSSPDVGID YWGQGTLVTVSS (SEQ ID NO: 67) | DIQMTQSPSSLSASVGDRVTITCRASQSI SSYLNWYQQKPGKAPKLLMYAASSLQSGV PSRFSGSGSGTDFTLTISSLQPEDFATY YCLQIDSYPLTFGGGTKVEIK (SEQ ID NO: 77) |
| 6 | Antibody-F23-32k | QVQLEESGGGVVQPGESLRLSCAASGFT FSSYGMHWVRQAPGKGLEWVAVISYDG SNQYYADSVKGRFTISRDNSKNTLYLQM NSLRAEDTAVYYCAKDNQDSSPDVGID YWGQGTLVTVSS (SEQ ID NO: 67) | DIQMTQSPSSLSASVGDTVTI**T**CRASQNI SPFLNWYQ**Q**KPGKAPKLLIYAASSLQSGV PSRFSGSGSGTDFTLTISSLQPEDFATYY CQQYNSYPLTFGGGTKVEIK (SEQ ID NO: 78) |
| 7 | Antibody-A6-1k | QVQLQRSGGGLVQPGGSLRLSCAASGFT FSSYGMTWWRQAPGKGLEWVSAISNSG GSTYYADSVKGRFTISRDNSKNTLYLQM NSLRAEDTAVYYCAKDGPYFDYWGQG TLVTVSS (SEQ ID NO: 68) | DIQMTQSPSTLSASVGDRVTITCRVSQGI GDDLGWYQQKPGKAPKLLIYKASNLESGV PSRFSGSGSGTDFSLTISSLQPEDFATY FCQQAHSFPPTFGGGTKLEIK (SEQ ID NO: 79) |
| 8 | Antibody-M5-5k | QVQLVESGGGLIQPGGSLRLSCTASGFTF STYAMSWVRQAPGKGLEWVSAISGTGD WASYADSVKGRFTTSRDNSRNTLYLQM NNLRDEDTAIYYCAKSSSTVATDFDYGM DVWGQGTLVTVSS (SEQ ID NO: 69) | ETTLTQSPSTLSASVGDRVTITCRASEEIG SWLAWYQQTPGKAPKRLIYEASSLQSGVP SRFSGSGSGTDFTLTISSLQPEDFATYY CQQYGSYPPTFGQGTKVEIK (SEQ ID NO: 80) |
| 9 | Antibody-M5-7k | QVQLVESGGGLIQPGGSLRLSCTASGFTF STYAMSWVRQAPGKGLEWVSAISGTGD WASYADSVKGRFTTSRDNSRNTLYLQM NNLRDEDTAIYYCAKSSSTVATDFDYGM DVWGQGTLVTVSS (SEQ ID NO: 69) | DIVMTQSPSTLSASVGDRVTVTCRASEDI GRWLAWYQQKPGKAPKRLIYAASSLQS GVPSRFSGSGSGTEFTLTISSLQPEDFATY YCQQYYNYPPTFGQGTKVEIK (SEQ ID NO: 81) |
| 10 | Antibody-FE-16H | QVQLVESGGGLVQPGGSLRLSCAASGFT FSSYAMSWVRQAPGKGLEWVSAISGSG GSTYYADSVKGRFTISRDNSKNSLYLQM NSLRAEDTAVYYCARGDSSSWFIFQDW GQGTLVTVSS (SEQ ID NO: 70) | QSVLTQPPSASGTPGQRVTISCSGSSSNM GSNPVNWYQQLPGEAPQLLMYNNNQR PSGVPDRFSGSKSGTSASLAISGLQSEDE AEYYCAAWDDGLNGWVFGGGTKLTVL (SEQ ID NO: 82) |
| 11 | Antibody-A2 | QVQLVESGGGLIQPGGSLRLSCAASGFT VSSNYMSWVRQAPGEGLEWIATIYYGG STYYNPSLKSRVTISADMSKNQFSLKLSS MTAADTAVYYCARVVVPGYFDLWGRG TLVTVSS (SEQ ID NO: 71) | SSELTQDPAVSVALGQTVSITCQGDSLRS YYASWYQQKPGQAPVPVIYGKNNRPSG IPDRFSGSSSGNTASLTITGAQAEDEADY YCHSRDSSGKYVFGVGTKLTVL (SEQ ID NO: 83) |

TABLE 3-continued

| Sequence listing of each numbered anti-OX40 antibody | | | |
|---|---|---|---|
| No. | Name | Heavy chain variable region | Light chain variable region |
| 12 | Antibody M | QVQLVESGGGVVQPGESLRLSCAASGFT FSSYGMHWVRQAPGKGLEWVAVIWED GSNQYYADSVKGRFTISRDNSKNTLYLQ MNSLRAEDTAVYYCAKDNQDTSPDVGI DYWGQGTLVTVSS (SEQ ID NO: 72) | DIQMTQSPSSLSASVGDRVTITCRASQNI SPFLNWYQQKPGKAPKLLIYAAVGLQSGV PSRFSGSGSGTDFTLTISSLQPEDFATYY CQQYTDYPLTFGGGTKVEIK (SEQ ID NO: 84) |

The present invention further comprises an antibody that binds to the same epitope as the anti-OX40 antibody described herein. For example, the antibody of the present invention specifically binds to an epitope comprising one or more amino acid residues on human OX40 (see, e.g., P43489 in Uniprot).

Those skilled in the art will recognize that it can be determined whether an antibody binds to the same epitope as the antibody described herein (e.g., the antibody listed in Table 3, or one antibody comprising a variable heavy chain having a sequence selected from SEQ ID NOs: 64-72 and a variable light chain having a sequence selected from SEQ ID NOs: 73-84) simply by ascertaining whether a test antibody prevents the known antibody from binding to OX40 without undue experiments. As shown by the reduction in the binding of the antibody described herein, if the test antibody competes with the antibody disclosed herein, both antibodies may bind to the same or similar epitope.

An alternative method for determining whether an antibody has the specificity of the antibody described herein is to pre-incubate the antibody described herein with soluble OX40 protein to which the antibody generally responses and then add the test antibody to determine whether the ability of the test antibody to bind to OX40 is suppressed. If the test antibody is suppressed, it has the same or functionally the same epitope specificity as the antibody disclosed herein.

In some embodiments, the antibodies of the present invention can be prepared using, for example, the methods described in the examples provided below. In some embodiments, the antibodies may also be prepared by using Trioma technology, human B-cell hybridoma technology (see Kozbor et al., 1983, *Immunol Today,* 4:72), EBV hybridoma technology (see Cole et al., 1985, In: *Monoclonal Antibodies and Cancer Therapy*, Alan R. Liss, Inc., pp. 77-96), and the like.

Antibodies can be purified by known techniques, for example, affinity chromatography, immunoaffinity chromatography and the like using protein A or protein G. For example, purification of immunoglobulins is discussed by D. Wilkinson (*The Scientist*, published by The Scientist, Inc., Philadelphia Pa., Vol. 14, No. 8 (2000), pp. 25-28).

Monoclonal anti-OX40 antibodies of the present invention have the ability to regulate, promote, activate and initiate intracellular signals of OX40 and/or otherwise enable them to be activated. In some embodiments, the anti-OX40 antibodies (such as fully human antibodies or humanized antibodies) can be produced by, for example, a yeast surface display method. See patents WO2009036379 and WO2010105256. In this method, a natural or recombinant OX40 or a fragment thereof is used to screen a combinatorial library of yeast carrying random pairs of light and heavy chains.

Fc Modification

Relevant effector functions of the antibodies described herein can be modified to improve, for example, the efficacy of the antibodies in treating diseases and disorders associated with OX40 signaling. For example, since tumor-infiltrating regulatory T cells (Tregs) are ubiquitously expressed, one or more mutations may be introduced into the Fc region of the antibody to improve the function of ADCC, thereby killing Tregs more effectively. For another example, complete activation of intracellular signals of OX40 requires aggregation of multiple OX40 receptors or even oligomerization thereof, and therefore one or more mutations can be introduced into the Fc region of the antibody to improve aggregation capacity of the antibody itself or improve binding capacity to Fc receptors to promote the aggregation of the antibody, thereby more completely activating intracellular signals of OX40.

In some embodiments, the antibody described herein is of the IgG isotype. In some embodiments, a constant region of the antibody is of a human IgG1 isotype and has amino acid sequences set forth in SEQ ID NO: 90 and SEQ ID NO: 91. In some embodiments, specific amino acids on the human IgG1 constant region are modified to modify the glycosylation of the antibody, e.g., afucosylation of N297. In some embodiments, the antibody or the antigen-binding fragment thereof comprises a small amount of fucose modification, or little fucose modification, or no fucose modification, and the ADCC effect is significantly improved. In some embodiments, the antibody or the fragment thereof has up to one (or up to two or three) amino acid residues modified by fucose. In some embodiments, the antibody or the fragment thereof comprises no more than 0.01%, 0.1%, 1%, 2%, 3%, 4% or 5% of protein molecules modified by fucose. In some embodiments, an antibody with reduced or eliminated fucose modification has stronger ADCC effect and is suitable for certain therapeutic use. In some embodiments, the antibody or the antigen-binding fragment thereof is expressed in an engineered CHO cell. In some embodiments, the engineered CHO cell is a CHO cell in which one or more of the following genes are reduced or knocked out: a Slc35c1 gene, a fut8 gene, a GDP-mannose 4,6-dehydratase (GMD) gene, a GDP-4-keto-6-deoxymannose-3,5-epimerase-4-reductase (GMER) gene and a GDP-fucose transporter (GFT) gene. In some embodiments, the engineered CHO cell is a CHO cell with the fut8 gene knocked out.

In some embodiments, specific amino acids on the antibody constant region are modified to change the interaction of Fc receptors, e.g., mutations of S267E/L328F.

In some embodiments, a constant region of the antibody is of a human IgG2 isotype and has amino acid sequences set forth in SEQ ID NOs: 92 and 93, wherein the amino acid sequence set forth in SEQ ID NO: 92 is:

ASTKGPSVFPLAPCSRSTSESTAALGCLVKDYFPE

PVTVSWNSGALTSGVHTFPAVLQSSGLYSLSSVVT

VPSSNFGTQTYTCNVDHKPSNTKVDKTVERKCCVE

CPPCPAPPVAGPSVFLFPPKPKDTLMISRTPEVTC

VVVDVSHEDPEVQFNWYVDGVEVHNAKTKPREEQF

NSTFRVVSVLTVVHQDWLNGKEYKCKVSNKGLPAP

IEKTISKTKGQPREPQVYTLPPSREEMTKNQVSLT

CLVKGFYPSDIAVEWESNGQPENNYKTTPPMLDSD

GSFFLYSKLTVDKSRWQQGNVFSCSVMHEALHNHY

TQKSLSLSPGK;

wherein the amino acid sequence set forth in SEQ ID NO: 93 is:

RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC.

In some embodiments, a constant region of the antibody is of a human IgG4 isotype and has amino acid sequences set forth in SEQ ID NOs: 94 and 95, wherein the amino acid sequence set forth in SEQ ID NO: 94 is:

ASTKGPSVFPLAPCSRSTSESTAALGCLVKDYFPE

PVTVSWNSGALTSGVHTFPAVLQSSGLYSLSSVVT

VPSSSLGTKTYTCNVDHKPSNTKVDKRVESKYGPP

CPPCPAPEFLGGPSVFLFPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFFLYSRLTVDKSRWQEGNVFSCSVMHEALHNH

YTQKSLSLSLGK;

wherein the amino acid sequence set forth in SEQ ID NO: 95 is:

RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC.

In some embodiments, the hinge region within the human IgG4 constant region is modified to avoid or reduce chain swapping. In other embodiments, amino acid 235 on the human IgG4 constant region is modified to change the interaction of Fc receptors.

Uses of Anti-OX40 Antibodies or Antigen-Binding Fragments Thereof

Diseases or disorders that can be treated by the anti-OX40 antibodies described herein include hematologic cancers and/or solid tumors. The hematologic cancers include, for example, leukemia, lymphoma and myeloma. In some embodiments, the leukemia includes acute lymphocytic leukemia (ALL), acute myelogenous leukemia (AML), chronic lymphocytic leukemia (CLL), chronic myelogenous leukemia (CML) and myeloproliferative diseases/tumors (MPDs). The lymphoma includes Hodgkin's lymphoma, indolent and aggressive non-Hodgkin's lymphoma, Burkitt's lymphoma and follicular lymphoma (both small and large cell lymphomas). The myeloma includes multiple myeloma (MM), giant cell myeloma, heavy chain myeloma and light chain or Bence-Jones myeloma. The solid tumor includes, for example, breast cancer, ovarian cancer, lung cancer, pancreatic cancer, prostate cancer, melanoma, colorectal cancer, lung cancer, head and neck cancer, bladder cancer, esophageal cancer, liver cancer and renal cancer.

A therapeutically effective amount of the antibody described herein relates to an amount required to achieve a therapeutic goal. The amount required for administration depends on the binding affinity of the antibody for its specific antigen, the severity of the disease, disorder or condition, the route of administration, the rate at which the antibody administered in the subject is depleted from free volume, and the like. In some embodiments, a range of the therapeutically effective dose of the antibody or the antibody fragment described herein is from about 0.01 mg/kg to about 100 mg/kg. In some embodiments, a range of the therapeutically effective dose of the antibody or the antibody fragment described herein is from about 0.1 mg/kg to about 30 mg/kg. A range of administration frequency may be, for example, once every two weeks or once every three weeks.

In other embodiments, antibodies for OX40 can be used in methods known in the art related to OX40 localization and/or quantification (e.g., for determining the level of OX40 and/or both OX40 and OX40L in a suitable physiological sample, for diagnostic methods, for protein imaging, etc.).

In some embodiments, the anti-OX40 antibody is administered to a patient diagnosed with clinical symptoms associated with one or more of the aforementioned diseases (including but not limited to cancers or other neoplastic disorders). After diagnosis, the anti-OX40 antibody is administered to reduce or reverse the effects of clinical symptoms associated with one or more of the aforementioned diseases.

Overexpression of OX40 is observed in certain tumor samples, and patients with cells overexpressing OX40 are likely to respond to treatment with the anti-OX40 antibody of the present invention. Thus, the antibodies of the present invention may also be used for diagnosis and prognosis.

In some embodiments, a sample comprising cells may be obtained from a patient, which may be a cancer patient or a patient to be diagnosed. The cells are cells of a tumor tissue or tumor mass, a blood sample, a urine sample, or any sample from the patient. After an optional pretreatment of the sample, the sample can be incubated with the antibody of the present invention under a condition allowing the antibody to interact with a OX40 protein that may be present in the sample, and the anti-OX40 antibody can be used for detecting the presence of the OX40 protein in the sample.

The antibody of the present invention can also be used for detecting OX40 in patient samples, and thus can be used for diagnosis. For example, the anti-OX40 antibody of the present invention is used for in vitro assays (e.g., ELISA) to detect the level of OX40 in patient samples.

In one embodiment, the anti-OX40 antibody of the present invention is immobilized on a solid support (e.g., wells of a microtiter plate). The immobilized antibody acts as a capture antibody to capture any OX40 that may be present in the test sample. Before the immobilized antibody is contacted with the patient sample, the solid support is washed and treated with a blocking reagent (e.g., milk protein or albumin) to avoid the nonspecific adsorption of the analyte. The wells are then treated with a test sample that may comprise antigens or a solution comprising a standard amount of antigens. Such samples are, for example, serum samples from the subject, which may have circulating antigen levels that are considered capable of diagnosing a certain lesion. After the test sample or the standard is washed away, the solid support is treated with a detectably labeled secondary antibody. The labeled secondary antibody is used as a detect antibody. The level of the detectable label is measured and the concentration of OX40 in the test sample is determined by comparing with a standard curve established for the standard sample.

Based on the results obtained from in vitro diagnostic assays using the anti-OX40 antibodies of the present invention, the diseases of the subjects (e.g., clinical symptoms associated with ischemia or autoimmune or inflammatory diseases) can be graded based on the expression levels of OX40 and/or OX40L. For specific diseases, blood samples are taken from subjects diagnosed to be at multiple stages of disease progression and/or at multiple points of disease treatment. A range of antigen concentrations considered to be characteristics of each stage is determined using a population of samples that provides statistically significant results for each stage of progression or therapy.

In some embodiments, when an anti-OX40 antibody or an antigen-binding fragment thereof described herein is used, the antibody or the fragment thereof is present in the form of a pharmaceutical composition, wherein the pharmaceutical composition can consist of the anti-OX40 antibody or the antigen-binding fragment thereof and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like that are compatible with pharmaceutical administration. Suitable carriers are described in the latest edition of Remington's Pharmaceutical Sciences. Such carriers or diluents include, but are not limited to, water, saline, Ringer's solution, glucose solution and/or 5% human serum albumin.

The preparation of the pharmaceutical composition should be compatible with the intended route of administration thereof. Examples of the route of administration include parenteral administration, such as intravenous, intradermal, subcutaneous, oral (e.g., inhalational), transdermal (i.e., topical), transmucosal and rectal administration. Solutions or suspensions used for parenteral, intradermal or subcutaneous administration may include the following components: sterile diluents for injection, such as water, saline solutions, fixed oils, polyethylene glycols, glycerol, propylene glycol or other synthetic solvents; antibacterial agents, such as benzyl alcohol or methylparaben; antioxidants, such as ascorbic acid or sodium bisulfite; chelating agents, such as ethylenediamine tetraacetic acid (EDTA); buffers, such as acetates, citrates or phosphates; and agents for adjusting osmotic pressure, such as sodium chloride or dextrose. The pH can be adjusted with acids or bases, such as hydrochloric acid or sodium hydroxide. The parenteral formulation can be packaged in an ampoule, a disposable syringe or a multiple-dose vial made of glass or plastic.

The pharmaceutical composition suitable for injection includes a sterile aqueous solution (herein water-soluble solution) or dispersion and sterile powders for the instant preparation of a sterile injectable solution or dispersion. For intravenous administration, a suitable carrier includes normal saline, bacteriostatic water or phosphate-buffered saline (PBS). In some embodiments, the composition must be sterile and easy to be injected. The composition must be stable under the conditions of manufacture and storage and must be able to prevent the contamination of microorganisms such as bacteria and fungi. The carrier may be a solvent or dispersion medium comprising, for example, water, ethanol or polyol (e.g., glycerol, propylene glycol and liquid polyethylene glycol), and a suitable mixture thereof. In some embodiments, the pharmaceutically acceptable carrier may include an antibacterial and/or antifungal agent, e.g., p-hydroxylbenzoate, chlorobutanol, phenol, ascorbic acid and thimerosal. In some embodiments, the pharmaceutically acceptable carrier may include an isotonic agent, such as a sugar, a polyol (such as mannitol and sorbitol), and sodium chloride.

As desired, sterile injectable solutions can be prepared by incorporating a required amount of the antibody into a suitable solvent having combinations of one or more of the ingredients described above (as desired), and then filtered and disinfected. The aforementioned sterile solutions may also be prepared as powders by lyophilizing for the preparation of sterile injectable solutions when administration.

In some embodiments, the antibodies of the present invention can activate an immune response and thus be used for treating infections.

Infections are invasion of pathogenic factors in tissues, their reproduction, and the response of the host tissues to these factors and toxins they produce. Infections may be caused by infectious agents, such as viruses, viroids, prions, bacteria, nematodes such as parasitic ascarids and pinworms, arthropods such as ticks, mites, fleas and lice, fungi such as tinea, and other macroparasites such as cestodes and other worms. In a certain aspect, the infectious agent is a bacterium, such as a gram-negative bacterium. In a certain aspect, the infectious agent is a virus, such as a DNA virus, an RNA virus, and a retrovirus. Non-limiting examples of viruses include adenovirus, coxsackievirus, Epstein-Barr virus, hepatitis A virus, hepatitis B virus, hepatitis C virus, herpes simplex virus type 1, herpes simplex virus type 2, cytomegalovirus, human herpes virus type 8, HIV, influenza virus, measles virus, mumps virus, human papilloma virus, parainfluenza virus, poliovirus, rabies virus, respiratory syncytial virus, rubella virus and varicella-zoster virus.

The antibodies disclosed herein can also be used for treating infectious diseases caused by microorganisms, or for killing microorganisms by targeted binding of the microorganisms to immune cells for the purpose of eliminating the microorganisms. In a certain aspect, the microorganisms include a virus, including RNA and DNA viruses, a gram-positive bacterium, a gram-negative bacterium, a protozoan or a fungus.

EXAMPLES

Example 1: Production and Purification of OX40 Antigens and Control Antibodies 1.1 Preparation of Human OX40 Antigens The amino acid sequence of human OX40 (P43489) was obtained from the protein database Uniprot, wherein the amino acid sequence of the extracellular region of human OX40 was residues at positions 1 to 216. The amino acid sequence of human IgG1-Fc (P01857) obtained from the protein database Uniprot was residues at positions 104 to 330. Nucleotide sequences corresponding to OX40 and Fc were then obtained by artificial synthesis (General Biol) and each inserted into the pCDNA3.0 vector (purchased from Invitrogen) by digestion-ligation. Recombinant plasmids pCDNA-OX40-his and pCDNA-OX40-Fc were obtained. The above plasmids were then transiently transfected into HEK293 by PEI, the supernatant was collected after 7 days of culturing, and finally, by purification, hOX40-FC and hOX40-his protein samples were obtained for the following various examples.

1.2 Preparation of Positive Control Antibodies 11D4 and OX40mAb24

The sequences of the heavy and light chains of 11D4 were derived from U.S. Pat. No. 8,236,930. The sequences of the heavy and light chains of OX40mAb24 were derived from U.S. Pub. No. US2016/0137740. Nucleotide sequences corresponding to the above antibodies were obtained by artificial synthesis, and the nucleotides of the heavy chain and the nucleotides of the light chain were separately ligated to pCHO1.0 plasmid (purchased from Invitrogen) by digestion-ligation to obtain recombinant plasmids for expression of the full antibodies. According to the manufacturer's instructions, the recombinant plasmids above were each transfected into CHO-S cell lines using the Freedom CHO-S kit (purchased from Invitrogen), the supernatant was collected after 11 days of culturing, and finally, by purification, 11D4 and OX40mAb24 antibody protein samples were obtained for the following various examples.

Example 2: Preparation of Anti-OX40 Antibodies

According to the variable regions of each of antibodies No. 1-11 as shown in Table 3, the heavy chain constant region set forth in SEQ ID NO: 90 and the light chain constant region set forth in SEQ ID NO: 91, the corresponding nucleic acid sequences thereof were inserted into pCHO1.0 plasmid (purchased from Invitrogen) by molecular cloning technique to obtain recombinant plasmids for expressing of the full antibodies. According to the manufacturer's instructions, the recombinant plasmids above were each transfected into CHO-S cell lines using the Freedom CHO-S kit (purchased from Invitrogen), and the supernatant was collected after 11 days of culturing. Finally, the protein samples of eleven antibodies were obtained by purification, sequenced to verify the sequences and used for the following various examples.

The sequence of the heavy chain constant region is set forth in SEQ ID NO 90 below:

```
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK
```

-continued

```
THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
```

The sequence of the light chain constant region is set forth in SEQ ID NO 91 below:

```
RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC
```

Example 3: Identification of Binding Capacity of Anti-Human OX40 Antibodies 3.1 Affinity of Anti-Human OX40 Antibodies as Determined by Biological Optical Interferometry The ForteBio affinity assay was conducted according to the existing conventional method (Estep, P et al., *MAbs,* 2013, 5 (2): 270-8). The brief process is as follows: the sensor was equilibrated offline in an assay buffer (such as PBS) for 20 min and then subjected to online test for 60 s to establish a signal baseline. The purified antibodies obtained as described above were each loaded online onto a corresponding sensor (ForteBio), and finally the ForteBio affinity assay was conducted. The biotinylated candidate antibodies were adsorbed with the SA sensor, and binding and dissociation of hOX40-FC were each detected for about 5 min. The results are shown in Table 4, and N.D indicates not detected in Table 4. Finally, kinetic analysis was performed for all by using a 1:1 binding model. The results show that the affinity of some of the antibodies described herein is superior or close to that of the control antibody.

TABLE 4

Affinity ($K_D$) of candidate antibodies described herein for hOX40-FC as determined by biological optical interferometry

| Candidate antibodies Determination method | Adsorption of biotinylated antibodies with SA, and detection of OX40-Fc (50 nM, bivalent) |
|---|---|
| OX40mAb24 | 0.3 nM |
| Antibody-F10 | N.D |
| Antibody-X35-6L | <0.1 nM |
| Antibody-F15-1L | 3 nM |
| Antibody-F23-4k | 0.6 nM |
| Antibody-F23-7k | 2 nM |
| Antibody-F23-32k | 0.4 nM |
| Antibody-A6-1k | 4 nM |
| Antibody-M5-5k | 2 nM |
| Antibody-M5-7k | 0.4 nM |
| Antibody-FE-16H | 3 nM |
| Antibody-A2 | 9 nM |

3.2 Binding Capacity of Anti-Human OX40 Antibodies for Cell Surface Antigens

Jurkat cells overexpressing human OX40 (Jurkat-hOX40 cells) were generated by transfecting pCMV vectors with human OX40 cDNA. Jurkat-hOX40 cells ($0.5\times10^6$ cells) were incubated with 100 nM experimental antibody in PBS containing 0.1% BSA on ice for 40 min. The cells were then washed twice and incubated with the secondary antibody in PBS containing 0.1% BSA on ice for 25 min. The cells were washed twice and analyzed by flow cytometry on Accuri C6 system (BD Biosciences). The results are shown in FIG. 1.

Antibody-F23-4k and antibody-F23-32k, as well as two control antibodies 11D4 and OX40mAb24 at different concentrations were used to incubate Jurkat-hOX40 cells. The antibodies were each 3-fold diluted in gradient from 50 nM for a total of nine concentration points, MFI values were collected, and the data was treated with SoftMax Pro to obtain EC50 values of 1.5 nM, 1.0 nM, 1.5 nM and 5 nM, respectively.

PBMC cells from healthy humans (purchased from Leide Biosciences) were activated with anti-CD3/CD28 magnetic beads (purchased from Invitrogen) for 48 h, and $0.5\times10^6$ cells were co-incubated with 50 nM experimental antibody in PBS for 40 min. The cells were then washed twice and incubated with the anti-FC-PE secondary antibody (purchased from eBioscience) in PBS on ice for 30 min. The cells were washed twice and analyzed by flow cytometry, and MFI values were calculated. The results are shown in Table 5.

TABLE 5

Binding of experimental antibodies to OX40 on activated T cells (human PBMCs)

| | Binding percentage % | MFI (ten thousand) |
|---|---|---|
| IgG1 | 23 | 0.7 |
| OX40mAb24 | 81 | 6.0 |
| Antibody-F23-32K | 79 | 5.8 |

Example 4: Specificity of Anti-Human OX40 Antibodies

Figure 2:
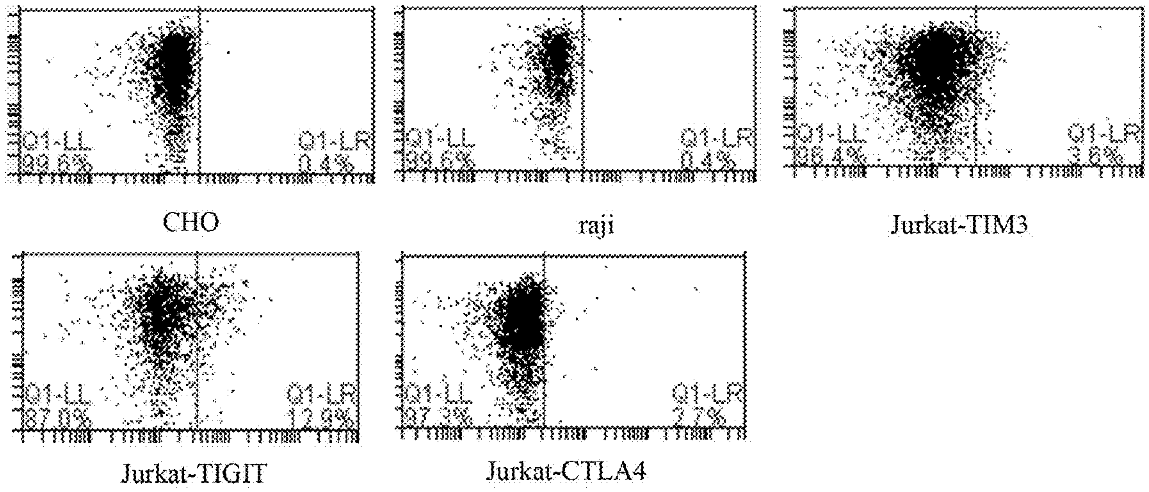
FIG. 2 shows that antibody-F23-32k does not bind to Jurkat-TIM3, Jurkat-CTLA4, Jurkat-TIGIT, CHO and Raji cells.

Similar to the method in Example 3.2, 100 nM experimental antibodies were each incubated with Jurkat cells overexpressing different antigens (Jurkat-TIM3, Jurkat-CTLA4 and Jurkat-TIGIT), CHO cells and Raji cells and then detected by flow cytometry. The results are shown in FIG. 2. The results show that antibody-F23-32k did not bind significantly to any of these antigens or cell lines, which indicates that it has good specificity.

10 ng of mouse OX40-his (mOX40-his), hCD27-FC and hOX40-his were coated overnight at 4° C. by ELISA, washed, and then incubated with antibody-F23-32K and control antibody, and finally labeled for color developing with HRP-labeled secondary antibody. The OD values detected are shown in Table 6. Similar to the method in Example 3.2, the affinity of antibody-F23-32K and control antibody for rhesus monkey OX40 (Rh-OX40) was detected by Fortebio according to the protein A sensor-antibody-OX40-his (100 nM) program settings. The results are shown in Table 6. The above results show that antibody-F23-32K neither bound to hCD27 (a protein in the same family with hOX40) nor mouse OX40, but it significantly bound to rhesus monkey OX40.

TABLE 6

Binding of antibody-F23-32k to hCD27, mouse OX40 and rhesus monkey OX40

| | Antibody-F23-32k | | OX40mAb24 | |
|---|---|---|---|---|
| ELISA (OD value) | | | | |
| mOX40-his | 0.17 | 0.20 | 0.17 | 0.17 |
| hCD27-FC | 0.15 | 0.13 | 0.20 | 0.2 |
| hOX40-his | 3.68 | 3.48 | 3.10 | 3.20 |
| Fortibio($K_D$) | | | | |
| Rh-OX40-his | 9 nM | | 3 nM | |

Figure 3:
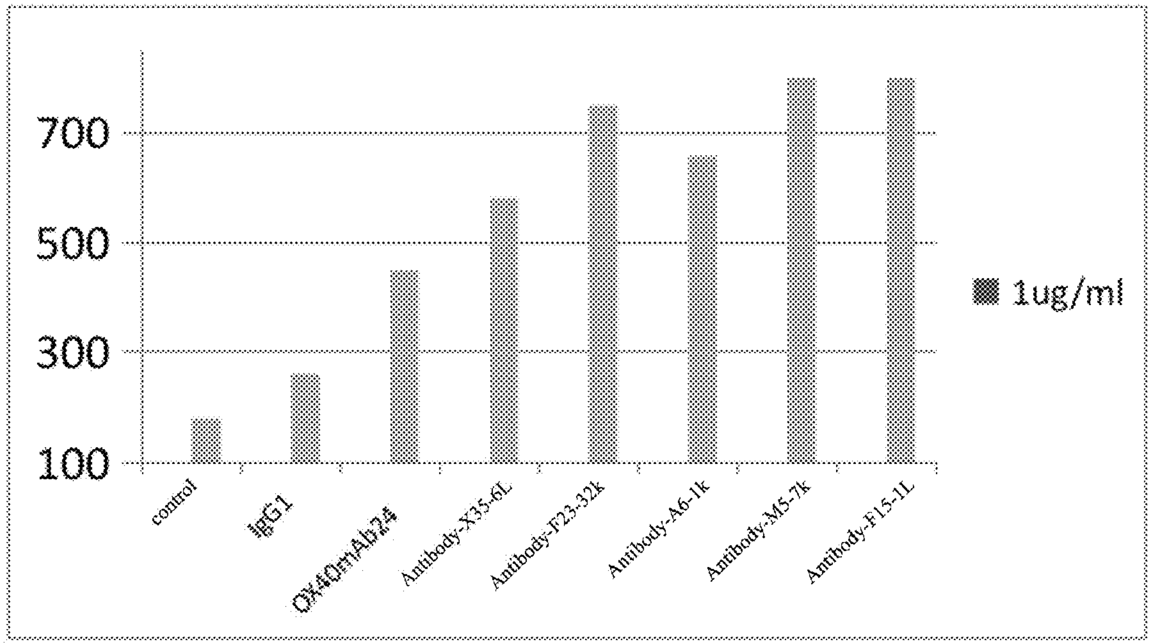
FIG. 3 shows the in vitro activation activities of candidate antibodies detected by the NFκB reporter gene system.

Example 5: Biological Activity Assays of Anti-OX40 Antibodies 5.1 In Vitro Activation Activities of Candidate Antibodies Detected by Using the NFκB Reporter Gene System pGL6-NFκB-luciferase-reporter plasmid (purchased from Beyotime) was electrotransfected into the Jurkat-hOX40 obtained based on Example 3.2, and finally the cells were subjected to pressurized screening with antibiotics to obtain a stable monoclonal strain named Jurkat-hOX40-NFκB. The cells were thawed, passaged three times, and then plated at $20\times10^4$ cells/well, wherein each well had 60 μL of medium. Corresponding 1 μg/mL experimental antibody and 2.5 μg/mL anti-FC antibody (goat anti-human, purchased from invitrogen) were added, and the mixture was incubated for 5 h and then added with 50 μL of fluorescent reactant per well (ONE-Glo™ Luciferase Assay System, purchased from promega corporation). The results are shown in FIG. 3. The data indicates that the activation signals of the experimental antibodies are all stronger than that of the control antibody at a concentration of 1 μg/mL.

Jurkat-hOX40-NFκB-2 cells with a larger window value were reconstructed according to the methods described previously to validate the activation activity of the antibodies. Studies have shown that antibodies directed to activating target receptors require the involvement of Fc-R if the activation activity is to be exerted strongly. Similar to the above method, Jurkat-hOX40-NFκB-2 cells were thawed, passaged three times, and then plated at $4\times10^4$ cells/well, wherein each well had 60 μL of medium. Corresponding experimental antibodies and 40,000 Raji cells (which naturally have certain Fc-receptors (i.e., Fc-R) on surface) were added, and the mixture was incubated for 4.5 h and then added with 50 μL of fluorescent reactant per well. The results are shown in Table 7. The data indicates that the activation activities of the candidate antibodies can be significantly improved in the presence of Raji cells.

TABLE 7

In vitro activation activities of candidate antibodies detected by using the NFκB reporter gene system in the presence of Raji cells

| | Antibody-F23-32k | +Raji | Antibody-F23-32K + Raji | OX40L |
|---|---|---|---|---|
| Luciferase IFM | 3700 | $1.6\times10^4$ | $1.5\times10^5$ | $5.9\times10^4$ |

Figure 4:
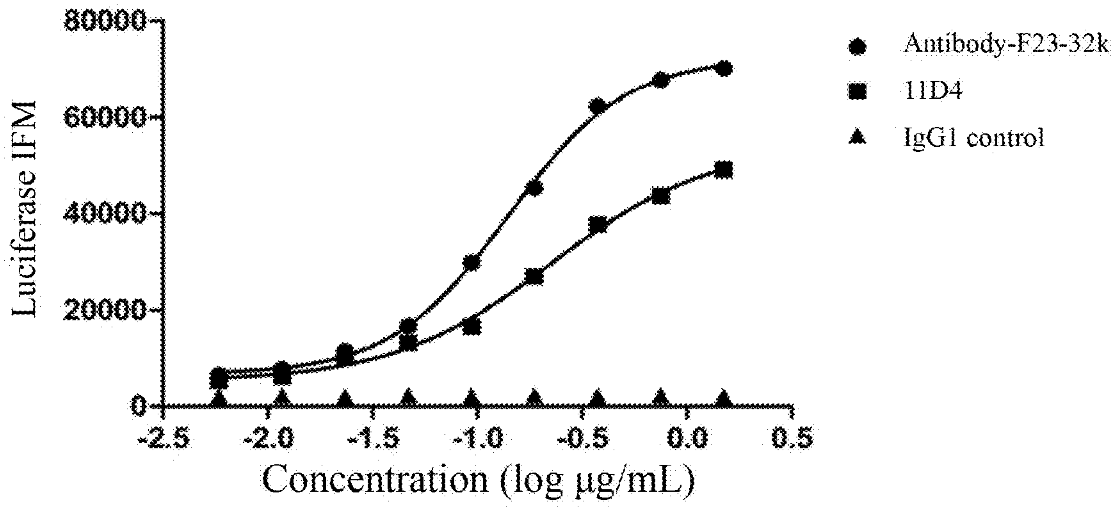
FIG. 4 shows the in vitro activation activities detected by the NFκB reporter gene system, when the candidate antibodies are aggregated by protein A; and the unit of EC50 values in FIG. 4 is μg/mL.

Similar to the above method, Jurkat-hOX40-NFκB-2 cells were thawed, passaged three times, and then plated at $4\times10^4$ cells/well, wherein each well had 60 μL of medium. The experimental antibody and protein A/G were incubated in a ratio of 1:1 for 2 min, and then the mixture was diluted in gradient from an initial concentration of 1.5 μg/mL. The results are shown in FIG. 4. The EC50 values of antibody-F23-32k and 11D4 were 0.1405 μg/mL and 0.2261 μg/mL, respectively.

5.2 Detection of Effect of Antibodies on Secretion of IL-2 from Activated PBMCs

Figures 5, 6:
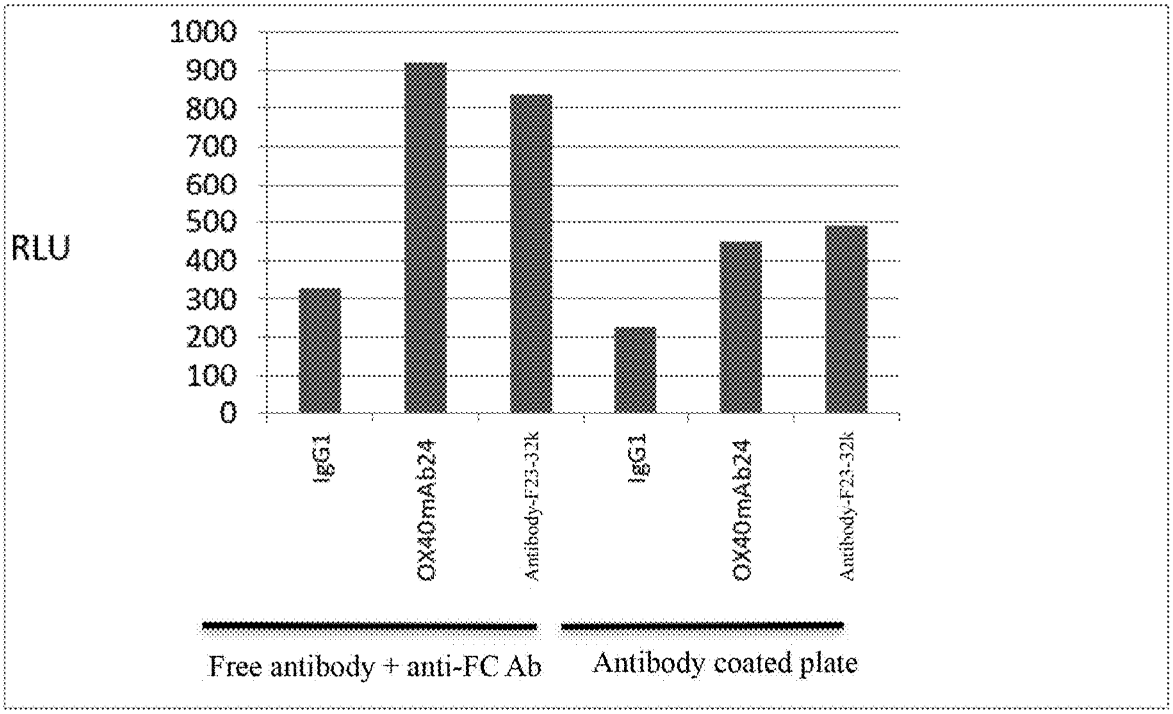
FIG. 5 shows the detected secretion level of inflammatory factor IL-2 from PBMCs activated with SEB under stimulation of the antibodies described herein.
FIG. 6 shows the in vitro activation activities of Fc mutants 32k-RY and 32k-R of experimental antibodies, as well as the change in activation activity in the presence of protein A or raji, as measured by the NFκB reporter gene system.

The agonist activity of the anti-OX40 antibodies described herein was assessed by measuring inflammatory cytokines released by T cells after T cell activation. PBMCs were obtained and plated at 200,000 cells/well on a 96-well plate, wherein each well had 200 μL of medium. Then 80 μg/mL SEB was added to activate the PBMCs. After 2 days, the PBMCs were collected, washed and plated at 200,000 cells/well, wherein each well had 200 μL of medium. Then 1 μg/mL candidate or control antibody and 2 μg/mL anti-FC antibody (goat anti-human, purchased from invitrogen) were added. After 3 days, the secretion level of IL-2 in the medium was determined by ELISA kit. The results are shown in FIG. 5. Similar to the above procedure, 1 μg/mL candidate or control antibody was coated on the plate, incubated overnight at 4° C. and then washed three times. The activated PBMCs were plated at 200,000 cells/well, wherein each well had 200 μL of medium. After 3 days, the secretion level of IL-2 in the medium was determined by ELISA kit (purchased from Neobioscience). The results are shown in FIG. 5. The data indicates that antibody-F23-32k of the present invention is comparable to the positive control.

Example 6: Enhanced Biological Activity of Anti-OX40 Antibodies by Fc Mutation Two IgG1-Fc mutant sequences (mutations RY (E345R and S440Y) and R (E345R)), which were named IgG1-FC-RY (SEQ ID NO: 88) and IgG1-FC-R (SEQ ID NO: 89), respectively, were obtained by artificial synthesis, and the sequences are shown in Table 8 (underline indicates the mutation position). Antibody-F23-32k was subjected to RY or R mutation, and the resulting antibodies were named as 32k-RY and 32k-R, respectively. Furthermore, it was confirmed by HPLC that in the free state, the antibodies were mainly present in the form of a monomer. Jurkat-hOX40-NFκB-2 and Jurkat-hOX40-NFκB cells were thawed and each used in the following experiment. Similar to the procedure in Example 5.1, the cells were passaged three times and then plated at $4\times10^4$ or 200,000 cells/well. The mixture was added with the corresponding antibody (1 μg/mL), antibody mutant (1 μg/mL), Raji cells (10,000 cells/well) or protein A (1 μg/mL, purchased from Sangon Biotech). The protocols and combinations of samples for addition to the 96-well plate are shown in FIG. 6, and the results are also shown in FIG. 6. The antibodies comprising the RY or R mutation also significantly activate the OX40 signals in the absence of protein A, and are about ten times stronger than wild-type antibodies.

TABLE 8

Two IgG1-Fc mutant sequences

| SEQ ID NO | Sequence |
|---|---|
| 88 | ASTKGPSVFPLAPSSKSTSG<br>GTAALGCLVKDYFPEPVTVS<br>WNSGALTSGVHTFPAVLQSS<br>GLYSLSSVVTVPSSSLGTQT |

TABLE 8-continued

Two IgG1-Fc mutant sequences

| SEQ ID NO | Sequence |
|---|---|
| | YICNVNHKPSNTKVDKKVEP<br>KSCDKTHTCPPCPAPELLGG<br>PSVFLFPPKPKDTLMISRTP<br>EVTCVVVDVSHEDPEVKFNW<br>YVDGVEVHNAKTKPREEQYN<br>STYRVVSVLTVLHQDWLNGK<br>EYKCKVSNKALPAPIEKTIS<br>KAKGQPRRPQVYTLPPSRDE<br>LTKNQVSLTCLVKGFYPSDI<br>AVEWESNGQPENNYKTTPPV<br>LDSDGSFFLYSKLTVDKSRW<br>QQGNVFSCSVMHEALHNHYT<br>QKYLSLSPGK |
| 89 | ASTKGPSVFPLAPSSKSTSG<br>GTAALGCLVKDYFPEPVTVS<br>WNSGALTSGVHTFPAVLQSS<br>GLYSLSSVVTVPSSSLGTQT<br>YICNVNHKPSNTKVDKKVEP<br>KSCDKTHTCPPCPAPELLGG<br>PSVFLFPPKPKDTLMISRTP<br>EVTCVVVDVSHEDPEVKFNW<br>YVDGVEVHNAKTKPREEQYN<br>STYRVVSVLTVLHQDWLNGK<br>EYKCKVSNKALPAPIEKTIS<br>KAKGQPRRPQVYTLPPSRDE<br>LTKNQVSLTCLVKGFYPSDI<br>AVEWESNGQPENNYKTTPPV<br>LDSDGSFFLYSKLTVDKSRW<br>QQGNVFSCSVMHEALHNHYT<br>QKSLSLSPGK |

Example 7: Validation of Ability of Anti-OX40 Antibodies to Inhibit Tumor Growth in Humanized Mouse MC38 Tumor Graft Models The anti-tumor efficacy of the anti-OX40 antibodies of the present invention was studied in OX40 humanized mouse models (purchased from Biocytogen). MC38 tumor cells were seeded subcutaneously on the right side of B-hOX40 humanized female mice at a concentration of $5\times10^5$ cells/0.1 mL, and the mice were randomly grouped (6 mice per group) by tumor volume when tumors grew to about 119 $mm^3$. The antibodies were administered intraperitoneally at a frequency of Q3D (once every 3 days) at 3 mg/kg for a total of 6 administrations. PBS was used as the negative control.

Figure 7:
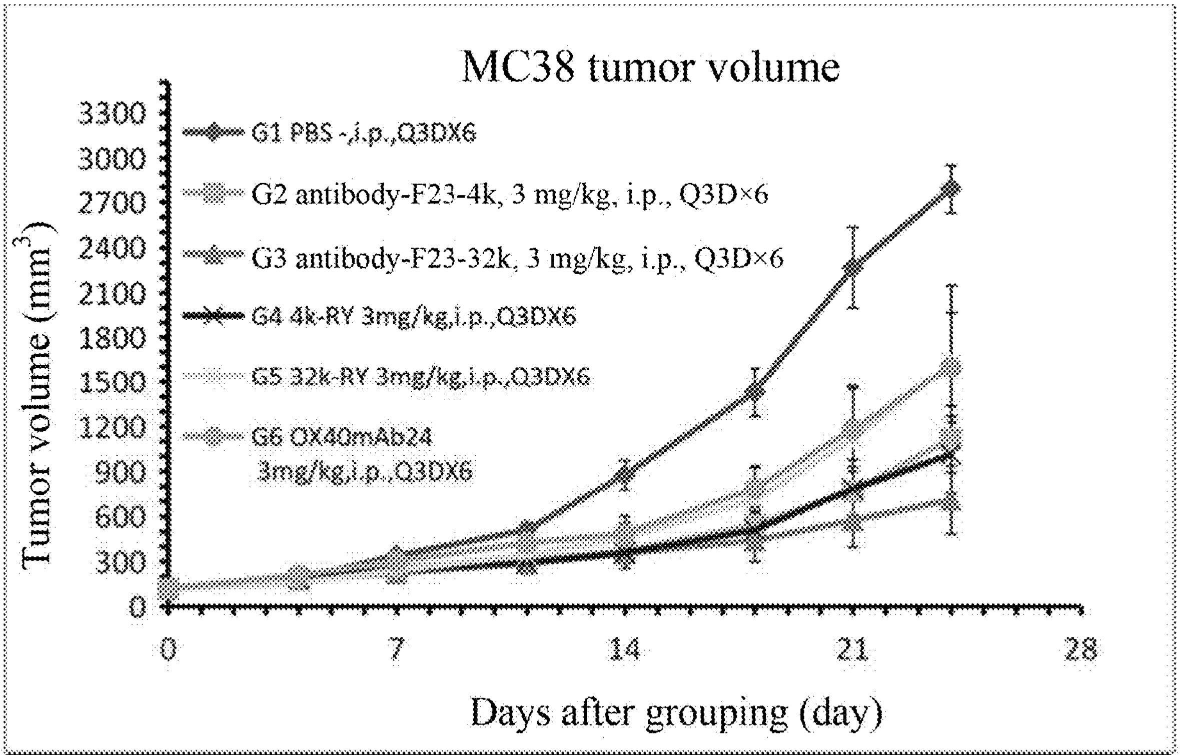
FIG. 7 shows the inhibitory effect of candidate antibodies on tumor (MC38) growth in vivo.

The tumor volume and body weight were measured twice a week throughout the study, and the mice were euthanized when the tumors reached an endpoint or when the mice had more than 20% of body weight loss. For each group, mean tumor volume was estimated with a digital caliper, and the tumor volume ($mm^3$) was calculated to be about 50 $mm^3$ by using the following formula: $(\text{width})^2\times\text{length}/2$. The results are shown in FIG. 7. In FIG. 7, TGI % is the inhibition rate for relative tumor volume, which is calculated by the formula: TGI %=(1−(mean RTV administration group)/(mean RTV control group))×100%, wherein the mean RTV administration group represents mean RTV of administration group and the mean RTV control group represents mean RTV of control group; RTVn=Vnt/Vn0, wherein the Vnt represents tumor volume at day t for a mouse numbered n, the Vn0 represents tumor volume at day 0 for a mouse numbered n, and the RTVn represents relative tumor volume at day t for a mouse numbered n. The heavy chain of antibody 4K-RY was obtained by FC mutation of antibody-F23-4k (E345R and S440Y).

To further understand the effect of experimental antibodies on tumor-infiltrating T cells (TILs) after administration, four suitable mice were selected from each group at the end of the above experiment. Tumor-infiltrating T lymphocytes and T lymphocytes in the blood were obtained by conventional dissection method. The cells were further fluorescently labeled by different labels, and finally fluorescence detection was conducted by using a flow sorter. The results show that the experimental antibodies of the present invention can increase the ratio of CD4+ and CD8+ T cells in tumor, and have no effect on the ratio of CD4+ and CD8+ T cells in blood.

Example 8

1) Affinity Maturation and Affinity Determination of Candidate Antibodies

Figure 8:
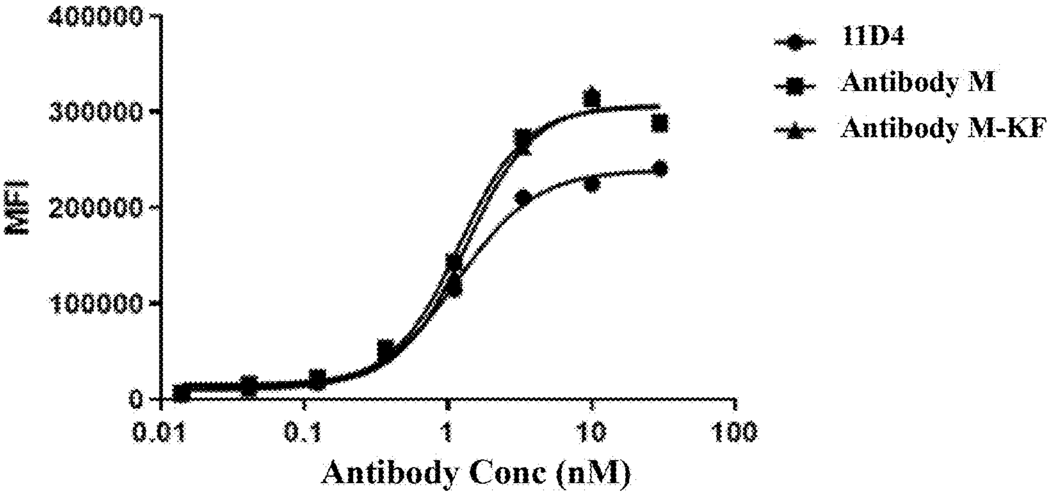
FIG. 8 shows the binding capacity of affinity-matured antibodies for OX40 on the cell surface, and the unit of EC50 values in FIG. 8 is nM.

Table 9 shows some mutations in the CDRs of antibody-F23-32K, wherein the underlined amino acids are the mutation sites. Table 10 illustrates the CDRs of eight full antibodies containing these amino acid mutations, and the rest of the sequences are the same as those of antibody-F23-32K. Their affinity was determined by BIACORE, and the specific process was binding the antibodies to probes and then detecting the binding and dissociation of 20 nM OX40-his. The results are shown in Table 11, wherein the affinity of antibody M is increased by about 70-fold to 0.16 nM, which is about 21-fold higher than that of OX40mAb24, and about 9-fold higher than that of 11D4. Similar to the method described above, Jurkat cells overexpressing OX40 were incubated with WEST+VGTD and ST+VGTD antibodies at different concentrations, and the resulting EC50 values were 1.2 nM and 1.3 nM, respectively. The results are shown in FIG. 8. The sequences of the anti-OX40 antibody (antibody M) are shown in Table 12; wherein, the expression cells used for the antibodies above (including antibody M) are CHO-S cells, and the method for preparing the antibody M-KF is as follows: the antibody M was identical to the antibody M-KF in terms of amino acid sequence and was expressed by the CHO cell line in which the fut8 gene was knocked out (the content of fucose in antibody M-KF was about 0%).

TABLE 9

Mutation sites of antibody-F23-32K

| | VH-CDR2 | VH-CDR3 | VL-CDR2 | VL-CDR3 |
|---|---|---|---|---|
| Antibody-F23-32K | VISYDGSNQYYADSVKG (SEQ ID NO: 11) | DNQDSSPDVGIDY (SEQ ID NO: 12) | AASSLQS (SEQ ID NO: 44) | QQYNSYPLT (SEQ ID NO: 39) |
| Amino acid mutation at underlined sites | WED, SED, AEV | T | VGL, VAL, VGS | TD, ND, DD, SD |

TABLE 10

CDR sequences of 8 mutated anti-OX40 antibodies

| | VH CDR1 | VH CDR2 | VH CDR3 | VL CDR1 | VL CDR2 | VL CDR3 |
|---|---|---|---|---|---|---|
| Antibody M | SYGMH (SEQ ID NO: 10) | VIWEDGSNQYYADSVKG (SEQ ID NO: 26) | DNQDTSPDVGIDY (SEQ ID NO: 27) | RASQNISPFLN (SEQ ID NO: 61) | AAVGLQS (SEQ ID NO: 25) | QQYTDYPLT (SEQ ID NO: 34) |
| T + VGL + TD | SYGMH (SEQ ID NO: 10) | VISYDGSNQYYADSVKG (SEQ ID NO: 11) | DNQDTSPDVGIDY (SEQ ID NO: 27) | RASQNISPFLN (SEQ ID NO: 61) | AAVGLQS (SEQ ID NO: 25) | QQYTDYPLT (SEQ ID NO: 34) |
| WEST + VL | SYGMH (SEQ ID NO: 10) | VIWEDGSNQYYADSVKG (SEQ ID NO: 26) | DNQDTSPDVGIDY (SEQ ID NO: 27) | RASQNISPFLN (SEQ ID NO: 61) | AASSLQS (SEQ ID NO: 44) | QQYNSYPLT (SEQ ID NO: 39) |
| VH + VGTD | SYGMH (SEQ ID NO: 10) | VISYDGSNQYYADSVKG (SEQ ID NO: 11) | DNQDSSPDVGIDY (SEQ ID NO: 102 | RASQNISPFLN (SEQ ID NO: 61) | AAVGLQS (SEQ ID NO: 25) | QQYTDYPLT (SEQ ID NO: 34) |
| WEST VG | SYGMH (SEQ ID NO: 10) | VIWEDGSNQ (SEQ ID NO: 26) | DNQDTSPDVGIDY (SEQ ID NO: 27) | RASQNISPFLN (SEQ ID NO: 61) | AAVGLQS (SEQ ID NO: 25) | QQYNSYPLT (SEQ ID NO: 39) |
| WEST + TD | SYGMH (SEQ ID NO: 10) | VIWEDGSNQYYADSVKG (SEQ ID NO: 26) | DNQDTSPDVGIDY (SEQ ID NO: 27) | RASQNISPFLN (SEQ ID NO: 61) | AASSLQS (SEQ ID NO: 44) | QQYTDYPLT (SEQ ID NO: 34) |
| T + VG | SYGMH (SEQ ID NO: 10) | VISYDGSNQYYADSVKG (SEQ ID NO: 11) | DNQDTSPDVGIDY (SEQ ID NO: 27) | RASQNISPFLN (SEQ ID NO: 61) | AAVGLQS (SEQ ID NO: 25) | QQYNSYPLT (SEQ ID NO: 39) |
| T + TD | SYGMH (SEQ ID NO: | VISYDGSNQYYADSVKG | DNQDTSPDVGIDY (SEQ | RASQNISPFLN (SEQ ID | AASSLQS (SEQ ID NO: | QQYTDYPLT (SEQ ID |

TABLE 10-continued

CDR sequences of 8 mutated anti-OX40 antibodies

| | VH CDR1 | VH CDR2 | VH CDR3 | VL CDR1 | VL CDR2 | VL CDR3 |
|---|---|---|---|---|---|---|
| | 10) | (SEQ ID NO: 11) | ID NO: 27) | NO: 61) | 44) | NO: 34) |

TABLE 11

Affinity of the 8 mutated anti-OX40 antibodies

| Antibody | $K_D$ (M) | $K_a$ (1/Ms) | $K_d$ (1/s) |
|---|---|---|---|
| 11D4 | $1.31 \times 10^{-09}$ | 353000 | 0.000461 |
| OX40mAb24 | $3.45 \times 10^{-09}$ | 408100 | 0.001410 |
| Antibody-F23-32K | $1.15 \times 10^{-08}$ | 841000 | 0.00965 |
| Antibody M | $1.6 \times 10^{-10}$ | 610000 | 0.0000977 |
| T + VGL + TD | $2.66 \times 10^{-10}$ | 448000 | 0.000119 |
| WEST + VL | $1.93 \times 10^{-09}$ | 371000 | 0.000714 |
| VH + VGTD | $5.65 \times 10^{-10}$ | 431000 | 0.000243 |
| WEST + VG | $7.7 \times 10^{-10}$ | 452000 | 0.000348 |
| WEST + TD | $6.53 \times 10^{-10}$ | 491000 | 0.000321 |
| T + VG | $4.54 \times 10^{-09}$ | 292000 | 0.00133 |
| T + TD | $5.01 \times 10^{-09}$ | 278000 | 0.00139 |

TABLE 12

Sequences of the anti-OX40 antibody (antibody M)

| SEQ ID NO | Name | Sequence |
|---|---|---|
| 86 | Heavy chain of antibody M | QVQLVESGGGVVQPGESLRLSCAASGFTFSSYGMHWVRQAPGKGLEWVAVIWEDGSNQYYADSVKGRFTISRDNSKNTLYLQMNSLRAEDTAVYYCAKDNQDTSPDVGIDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLIVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 87 | Light chain of antibody M | DIQMTQSPSSLSASVGDRVTITCRASQNISPFLNWYQQKPGKAPKLLIYAAVGLQSGVPSRFSGSGSGTDFTLTISSLQPEDFATYYCQQYTDYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

2) Detection of Antigen-Binding Specificity of Antibodies

The binding capacities of the antibody M-KF for human and cynomolgus monkey OX40 were determined by ELISA. The test method is as follows: human or cynomolgus monkey OX40 was coated on a plate and incubated overnight at 4° C. at a concentration of 2 μg/mL, and then incubated with antibody M-KF at different concentrations for detection. The antibody M-KF was 2-fold diluted in gradient from an initial concentration of 1 μg/mL or 2 μg/mL.

The results show that the antibody M-KF can bind to human and cynomolgus monkey OX40 with EC50 values of about 0.0340 ng/ml and 0.0352 ng/mL, respectively.

Example 9: ADCC Effect and In Vitro Activation Activity of Antibodies

Figure 9:
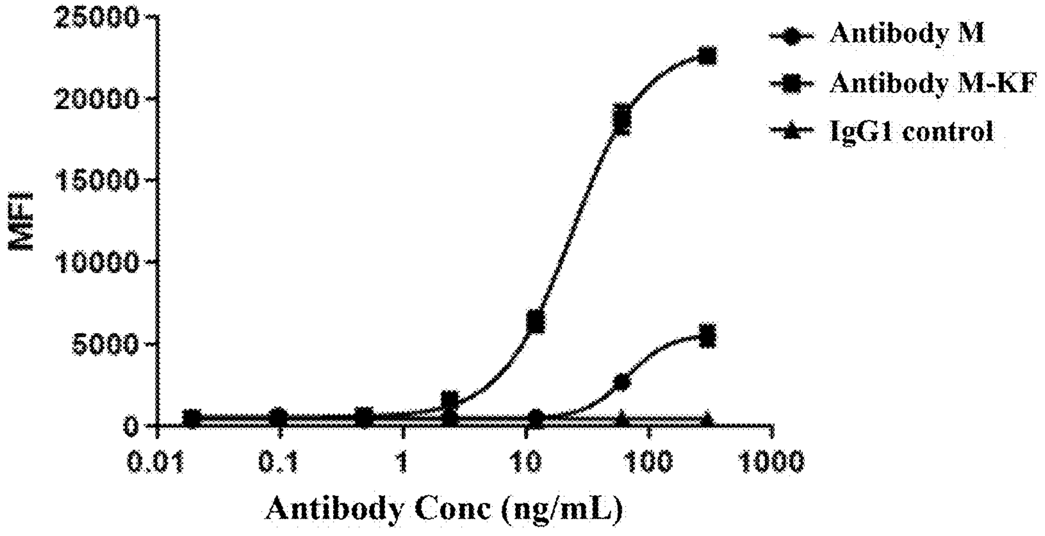
FIG. 9 shows the detection of candidate antibodies for ADCC effects, and the unit of EC50 values in FIG. 9 is μg/mL.
Figure 10:
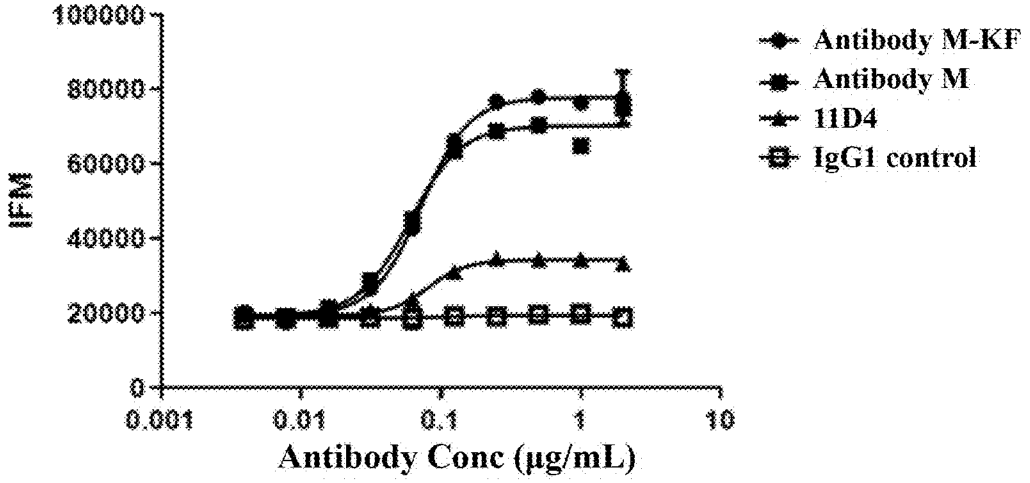
FIG. 10 shows the in vitro activation activities of affinity-matured antibodies in the presence of Raji cells detected by the NFκB reporter gene system.

The content of fucose in the antibody M was about 96%. The content of fucose in the antibody M-KF was about 0%. FC-RIIIA and NF-AT reporter genes were transferred into the Jurkat cells to obtain the Jurkat-ADCC cells. Jurkat-hOX40 cells and Jurkat-ADCC cells were mixed well at a ratio of 1:1, and the mixture was added with the antibody M and the antibody M-KF at corresponding concentration gradients. The results are shown in FIG. 9. Similar to the method described above (Example 5), the in vitro activation activities of candidate antibodies were detected by using the NFκB reporter gene system. Jurkat-hOX40-NFκB-2 cells were thawed, passaged three times, and then plated at $4\times10^4$ cells/well, wherein each well had 60 μL of medium, and the mixture was added with corresponding experimental antibodies and 40,000 Raji cells. The results are shown in FIG. 10. The EC50 values of the antibody M and the antibody M-KF were slightly better than that of 11D4, but the activation peaks of the two antibodies were about 2.5-fold greater than that of 11D4.

Example 10: In Vitro Efficacy Experiment of Antibodies

As describe above, the anti-tumor efficacy of the anti-OX40 antibodies of the present invention was studied in OX40 humanized mouse models (purchased from Biocytogen). MC38 tumor cells were seeded subcutaneously on the right side of B-hOX40 humanized female mice at a concentration of $5\times10^5$ cells/0.1 mL, and the mice were randomly grouped (6 mice per group) by tumor volume when tumors grew to about 119 $mm^3$. A batch of endotoxin-free antibodies, antibody M and antibody M-KF, were obtained by expression and purification, and the antibodies were administrated intraperitoneally at a frequency of Q3D and at three doses of 1 mg/kg, 0.2 mg/kg and 0.04 mg/kg, for a total of 6 administrations.

Figure 11:
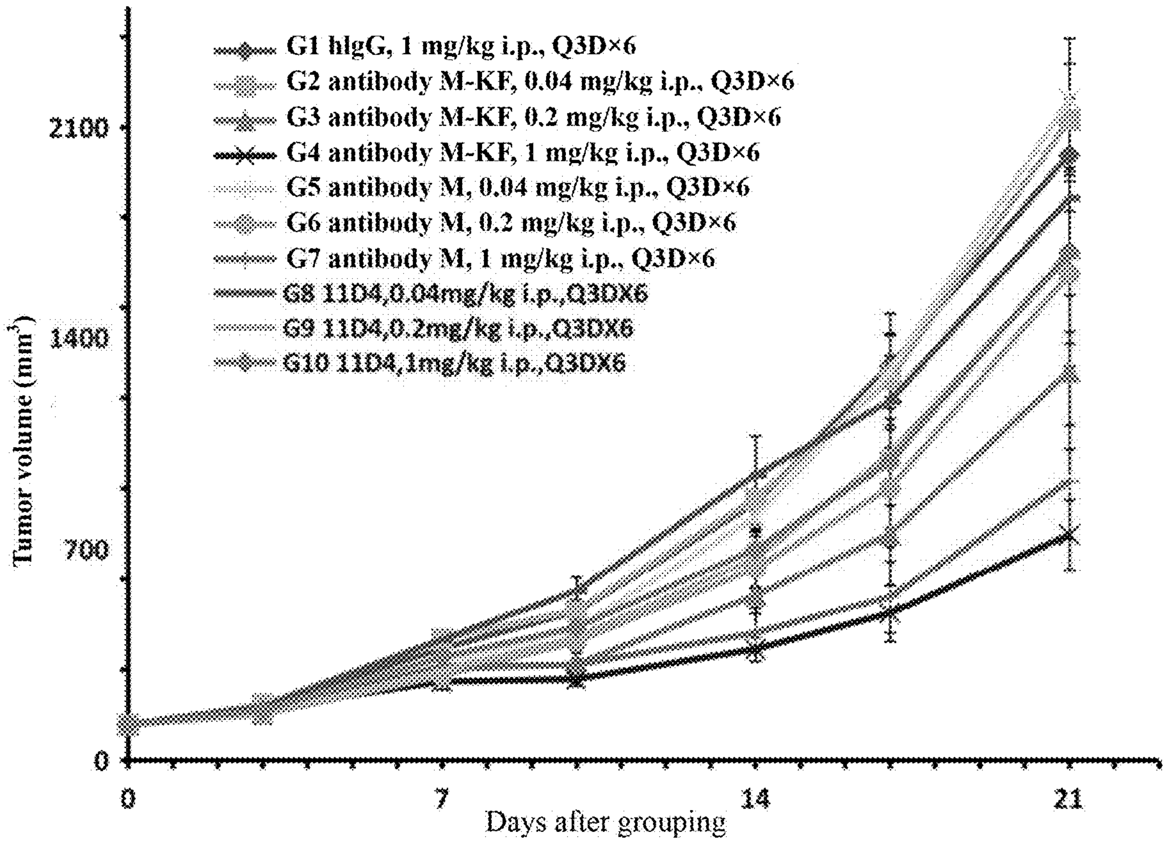
FIG. 11 shows the inhibitory effect of affinity-matured antibodies on tumor (MC38) growth in vivo.
Figure 12:
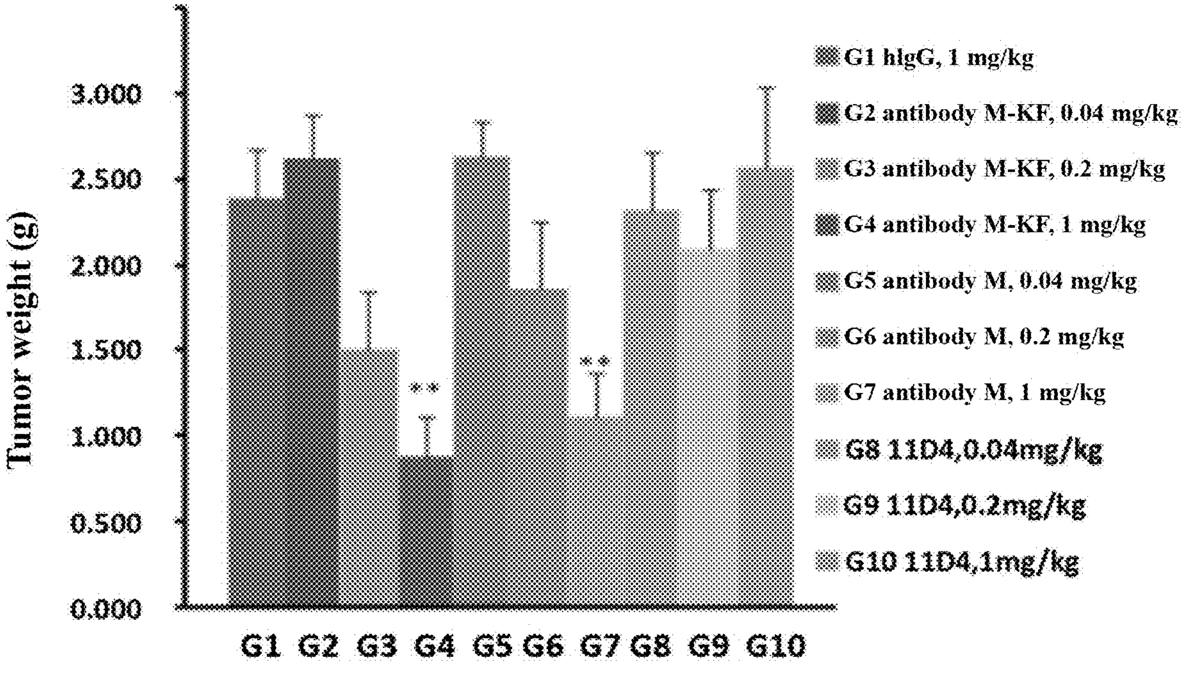
FIG. 12 shows the inhibitory effect of affinity-matured antibodies on tumor (MC38) growth in vivo at day 21.

The tumor volume and body weight were measured twice a week throughout the study, and the mice were euthanized when the tumors reached an endpoint or when the mice had more than 20% of body weight loss. For each group, mean tumor volume was estimated with a digital caliper, and the tumor volume ($mm^3$) was calculated to be about 50 $mm^3$ by using the following formula: $(\text{width})^2\times\text{length}/2$. The results are shown in FIG. 11, and the results at day 21 are shown in FIG. 12. The high-dose group of the antibody M and the antibody M-KF can significantly inhibit tumor growth ($P<0.05$), and the effect is significantly better than that of the high-dose group of 11D4. The medium-dose group of the antibody M-KF can also significantly inhibit tumor growth ($P<0.05$).

Example 11: ADCC Effect of Antibodies (PBMC Method)

Jurkat-hOX40 cells were used as target cells, and PBMCs derived from healthy humans were used as effector cells. PBMCs and Jurkat-OX40 cells were mixed in a quantity ratio of 25:1, and the mixture was added with the antibody M-KF or the antibody M (4-fold diluted in gradient from an initial concentration of 1 μg/mL), and incubated at 37° C. for 4 h. Then the corresponding signals were determined by using a kit CytoTox 96® Non-Radioactive Cytotoxicity Assay (Promega), and the ADCC-mediated killing effect on living cells of the antibody was determined by this system.

Figure 13:
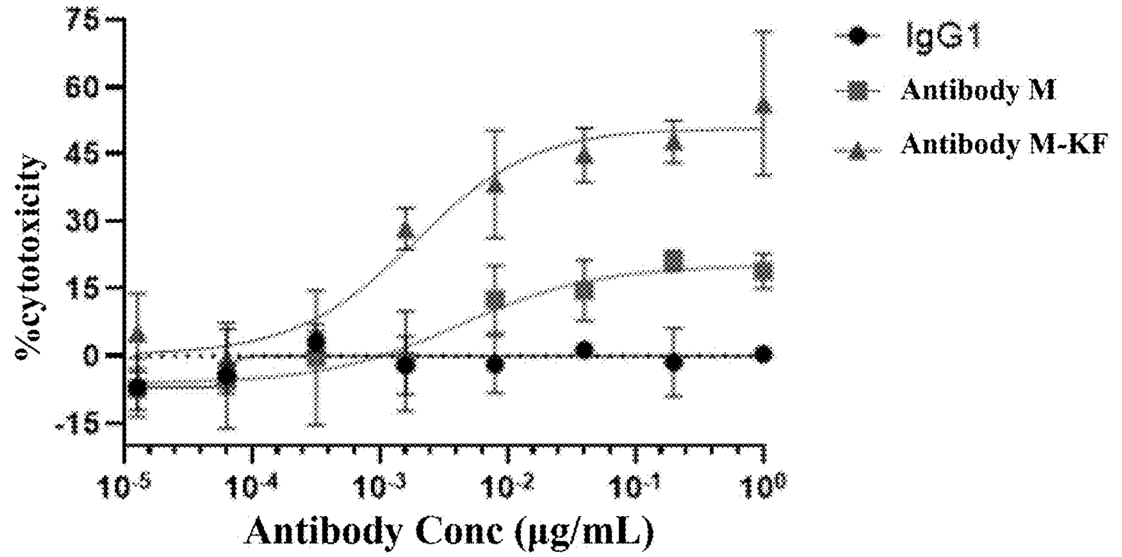
FIG. 13 shows the detection of antibodies for ADCC effects, wherein the abscissa represents concentration and the ordinate represents cytotoxicity.

The results are shown in FIG. 13 and indicate that the antibody M-KF has significant ADCC effect with an EC50 of about 1.891 ng/ml, which is more than 2-fold stronger than that of the antibody M.

Example 12: Detection of Effect of Antibodies on Secretion of IL-2 from Activated PBMCs The activation effect of the antibody M-KF on human peripheral blood mononuclear cells (PBMCs) under exogenous stimulation was detected by detecting the release of IL-2 cytokines using ELISA. PBMCs were stimulated by SEB (*Staphylococcus aureus* enterotoxin B) for 24 h, and the mixture was added with the antibody M-KF or the reference antibody 11D4 at different concentrations, and then incubated for 3 days. Finally, IL-2 secreted by PBMCs was detected by a human IL-2 ELISA development kit (HRP) (Mabtech, Cat. No. 3445-1H-20).

Figure 14:
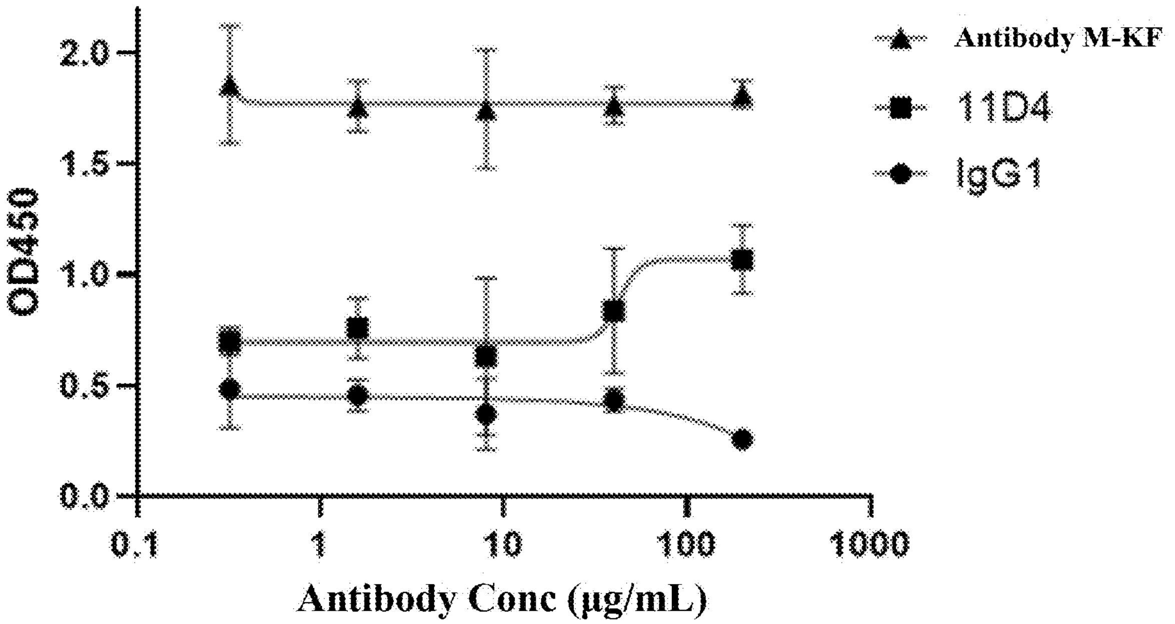
FIG. 14 shows the detection of the effect of antibodies on the secretion of IL-2 from activated PBMCs.

The results are shown in FIG. 14 and indicate that the amount of IL-2 secreted by PBMCs under the stimulation of the antibody M-KF at a concentration of 0.32 μg/mL or higher is about 4 times more than that of the negative control IgG1.

Example 13: Detection of Effect of Antibodies on Release of PBMC Cytokines Under a Non-Activating Condition The activation effect of the antibody M-KF on human PBMCs without exogenous stimulation was detected by detecting the release of IL-2, INF-γ, IL-6 and TNF-α cytokines using ELISA, thereby examining the safety of the antibody. The final purpose of the action mechanism of the antibody M-KF is to activate T cells and thereby stimulate the immune system and enhance the immune function. For safety, this type of antibodies may cause over-activation of the immune system in body, thereby causing a cytokine storm. Since IL-2, INF-γ, IL-6 and TNF-α are all common factors produced in large quantities when a cytokine storm occurs, these factors are selected for detection.

Human PBMCs without activation treatment were incubated with the antibody M-KF or CD28 antibody at different concentrations, and the antibody was 3-fold diluted in gradient from an initial concentration of 200 μg/mL. Finally, IL-2, INF-γ, IL-6 and TNF-α secreted by PBMCs were each detected by using a corresponding cytokine detection kit (Mabtech company).

Figure 15:
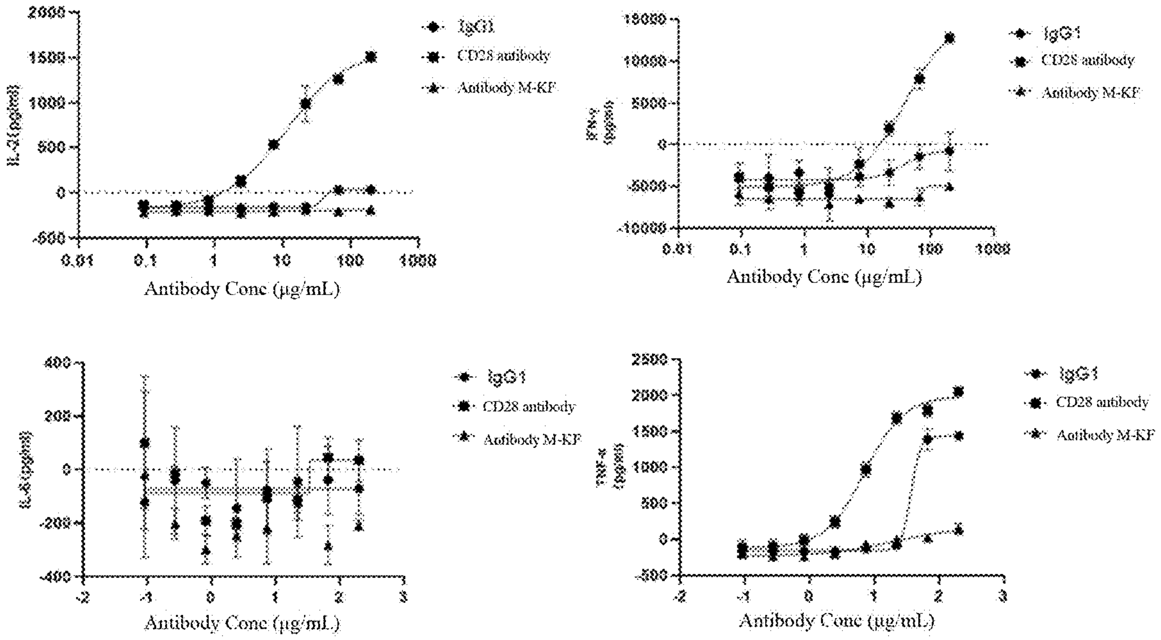
FIG. 15 shows the detection of the effect of antibodies on the release of PBMC cytokines under a non-activating condition.

As shown in FIG. 15, compared to the positive control anti-CD28 antibody, the antibody M-KF cannot enable PBMCs without exogenous stimulation to produce IL-2, INF-γ, IL-6 and TNF-α at a concentration of 200 g/mL or lower, indicating the antibody M-KF is safe to some extent.

All publications and patent documents cited herein are incorporated herein by reference, as if each of the publication and the documents are specifically and individually indicated to be incorporated herein by reference. Citation of publications and patent documents described above is not intended as an admission that any is pertinent prior art, nor does it constitutes any admission as to the contents or date of the same. Now, the present invention has been described in the written description, and it should be understood by those skilled in the art that the present invention may be practiced in various embodiments. The description and embodiments above are intended to be illustrative rather than limiting the claims of the present invention.

The invention claimed is:

1. An antibody or an antigen-binding fragment thereof, wherein the antibody or the fragment thereof specifically binds to OX40, and the antibody or the fragment thereof comprises:

(i) a VH CDR1 comprising SEQ ID NO: 10; a VH CDR2 comprising SEQ ID NO: 26; a VH CDR3 comprising SEQ ID NO: 27; a VL CDR1 comprising SEQ ID NO: 61; a VL CDR2 comprising SEQ ID NO: 25; and a VL CDR3 comprising SEQ ID NO: 34;

(ii) a VH CDR1 comprising SEQ ID NO: 4; a VH CDR2 comprising SEQ ID NO: 5; a VH CDR3 comprising SEQ ID NO: 6; a VL CDR1 comprising SEQ ID NO: 31; a VL CDR2 comprising SEQ ID NO: 32; and a VL CDR3 comprising SEQ ID NO: 33;

(iii) a VH CDR1 comprising SEQ ID NO: 1; a VH CDR2 comprising SEQ ID NO: 8; a VH CDR3 comprising SEQ ID NO: 9; a VL CDR1 comprising SEQ ID NO: 31; a VL CDR2 comprising SEQ ID NO: 35; and a VL CDR3 comprising SEQ ID NO: 36;

(iv) a VH CDR1 comprising SEQ ID NO: 10; a VH CDR2 comprising SEQ ID NO: 11; a VH CDR3 comprising SEQ ID NO: 12; a VL CDR1 comprising SEQ ID NO: 37; a VL CDR2 comprising SEQ ID NO: 38; and a VL CDR3 comprising SEQ ID NO: 39;

(v) a VH CDR1 comprising SEQ ID NO: 10; a VH CDR2 comprising SEQ ID NO: 11; a VH CDR3 comprising SEQ ID NO: 12; a VL CDR1 comprising SEQ ID NO: 40; a VL CDR2 comprising SEQ ID NO: 29; and a VL CDR3 comprising SEQ ID NO: 42;

(vi) a VH CDR1 comprising SEQ ID NO: 10; a VH CDR2 comprising SEQ ID NO: 11; a VH CDR3 comprising SEQ ID NO: 12; a VL CDR1 comprising SEQ ID NO: 61; a VL CDR2 comprising SEQ ID NO: 44; and a VL CDR3 comprising SEQ ID NO: 39;

(vii) a VH CDR1 comprising SEQ ID NO: 104; a VH CDR2 comprising SEQ ID NO: 14; a VH CDR3 comprising SEQ ID NO: 15; a VL CDR1 comprising SEQ ID NO: 46; a VL CDR2 comprising SEQ ID NO: 47; and a VL CDR3 comprising SEQ ID NO: 48;

(viii) a VH CDR1 comprising SEQ ID NO: 16; a VH CDR2 comprising SEQ ID NO: 17; a VH CDR3 comprising SEQ ID NO: 18; a VL CDR1 comprising SEQ ID NO: 49; a VL CDR2 comprising SEQ ID NO: 50; and a VL CDR3 comprising SEQ ID NO: 51;

(ix) a VH CDR1 comprising SEQ ID NO: 16; a VH CDR2 comprising SEQ ID NO: 17; a VH CDR3 comprising SEQ ID NO: 18; a VL CDR1 comprising SEQ ID NO: 52; a VL CDR2 comprising SEQ ID NO: 29; and a VL CDR3 comprising SEQ ID NO: 54;

(x) a VH CDR1 comprising SEQ ID NO: 1; a VH CDR2 comprising SEQ ID NO: 20; a VH CDR3 comprising SEQ ID NO: 21; a VL CDR1 comprising SEQ ID NO: 55; a VL CDR2 comprising SEQ ID NO: 56; and a VL CDR3 comprising SEQ ID NO: 57;

(xi) a VH CDR1 comprising SEQ ID NO: 22; a VH CDR2 comprising SEQ ID NO: 23; a VH CDR3 comprising SEQ ID NO: 24; a VL CDR1 comprising SEQ ID NO: 58; a VL CDR2 comprising SEQ ID NO: 59; and a VL CDR3 comprising SEQ ID NO: 60;

(xii) a VH CDR1 comprising SEQ ID NO: 10; a VH CDR2 comprising SEQ ID NO: 11; a VH CDR3 comprising SEQ ID NO: 27; a VL CDR1 comprising SEQ ID NO: 61; a VL CDR2 comprising SEQ ID NO: 25; and a VL CDR3 comprising SEQ ID NO: 34;

(xiii) a VH CDR1 comprising SEQ ID NO: 10; a VH CDR2 comprising SEQ ID NO: 26; a VH CDR3 comprising SEQ ID NO: 27; a VL CDR1 comprising SEQ ID NO: 61; a VL CDR2 comprising SEQ ID NO: 44; and a VL CDR3 comprising SEQ ID NO: 39;

(xiv) a VH CDR1 comprising SEQ ID NO: 10; a VH CDR2 comprising SEQ ID NO: 11; a VH CDR3 comprising SEQ ID NO: 12; a VL CDR1 comprising SEQ ID NO: 61; a VL CDR2 comprising SEQ ID NO: 25; and a VL CDR3 comprising SEQ ID NO: 34;

(xv) a VH CDR1 comprising SEQ ID NO: 10; a VH CDR2 comprising SEQ ID NO: 26; a VH CDR3 comprising SEQ ID NO: 27; a VL CDR1 comprising SEQ ID NO: 61; a VL CDR2 comprising SEQ ID NO: 25; and a VL CDR3 comprising SEQ ID NO: 39;

(xvi) a VH CDR1 comprising SEQ ID NO: 10; a VH CDR2 comprising SEQ ID NO: 26; a VH CDR3 comprising SEQ ID NO: 27; a VL CDR1 comprising SEQ ID NO: 61; a VL CDR2 comprising SEQ ID NO: 44; and a VL CDR3 comprising SEQ ID NO: 34;

(xvii) a VH CDR1 comprising SEQ ID NO: 10; a VH CDR2 comprising SEQ ID NO: 11; a VH CDR3 comprising SEQ ID NO: 27; a VL CDR1 comprising SEQ ID NO: 61; a VL CDR2 comprising SEQ ID NO: 25; and a VL CDR3 comprising SEQ ID NO: 39; or (xviii) a VH CDR1 comprising SEQ ID NO: 10; a VH CDR2 comprising SEQ ID NO: 11; a VH CDR3 comprising SEQ ID NO: 27; a VL CDR1 comprising SEQ ID NO: 61; a VL CDR2 comprising SEQ ID NO: 44; and a VL CDR3 comprising SEQ ID NO: 34.

2. The antibody or the antigen-binding fragment thereof according to claim 1, comprising a heavy chain variable region comprising any of the amino acid sequences comprising SEQ ID NOs: 65-72 or a peptide having at least 90% sequence homology to any of the amino acid sequences comprising SEQ ID NOs: 65-72; and further comprising a light chain variable region comprising any of the amino acid sequences comprising SEQ ID NOs: 74-84 or a peptide having at least 90% sequence homology to any of the amino acid sequences comprising SEQ ID NOs: 74-84.

3. The antibody or the fragment thereof according to claim 1, comprising a heavy chain constant region comprising SEQ ID NO: 88, 89 or 90 and/or a light chain constant region comprising SEQ ID NO: 91.

4. The antibody or the fragment thereof according to claim 1, wherein the antibody or the fragment thereof has an affinity value $K_D$ of ≤5 nM for OX40.

5. The antibody or the fragment thereof according to claim 1, wherein the content of fucose in the antibody is no more than 10%.

6. The antibody or the fragment thereof according to claim 1, wherein the content of fucose in the antibody is 0%.

7. A method of preparing the antibody or the fragment thereof according to claim 1, comprising transfecting a CHO cell in which a fut8 gene is knocked out.

8. A polynucleotide, encoding the antibody or the fragment thereof according to claim 1.

9. A cell, comprising one or more polynucleotides encoding the antibody or the fragment thereof according to claim 1.

10. A composition, comprising the antibody or the fragment thereof according to claim 1, and a pharmaceutically acceptable carrier.

11. A method for treating cancer or an infection in a patient in need thereof, comprising administering to the patient an effective dose of the antibody or the fragment thereof according to claim 1.

12. The method according to claim 11, wherein the cancer is selected from non-Hodgkin's lymphoma, acute lymphocytic leukemia, acute myelogenous leukemia, chronic lymphocytic leukemia, chronic myelogenous leukemia, multiple myeloma, breast cancer, ovarian cancer, head and neck cancer, bladder cancer, melanoma, colorectal cancer, pancreatic cancer, lung cancer, leiomyoma, leiomyosarcoma, glioma, glioblastoma, prostate cancer, esophageal cancer, liver cancer and renal cancer.

13. The method according to claim 11, further comprising administering to the patient a second cancer therapeutic agent.

14. An antibody or an antigen-binding fragment thereof, comprising a heavy chain variable region comprising SEQ ID NO: 72 and a light chain variable region comprising SEQ ID NO: 84.

15. The antibody or the fragment thereof according to claim 14, comprising a heavy chain constant region comprising SEQ ID NO: 88, 89 or 90 and/or a light chain constant region comprising SEQ ID NO: 91.

16. The antibody or the fragment thereof according to claim 14, wherein the content of fucose in the antibody is no more than 10%.

17. A method of preparing the antibody or the fragment thereof according to claim 14, comprising transfecting a CHO cell in which a fut8 gene is knocked out.

18. An antibody, comprising a heavy chain comprising SEQ ID NO: 86 and a light chain comprising SEQ ID NO: 87.

* * * * *